United States Patent
Deng et al.

(10) Patent No.: US 10,975,092 B2
(45) Date of Patent: Apr. 13, 2021

(54) PYRIMIDINE SEVEN-MEMBERED-RING COMPOUNDS, PREPARATION METHOD THEREFOR, PHARMACEUTICAL COMPOSITION THEREOF, AND USES THEREOF

(71) Applicant: Anhui New Star Pharmaceutical Development Co., Ltd., Hefei (CN)

(72) Inventors: Xianming Deng, Xiamen (CN); Dawang Zhou, Xiamen (CN); Lanfen Chen, Xiamen (CN); Zhixiang He, Xiamen (CN); Fuqin Fan, Xiamen (CN)

(73) Assignee: Anhui New Star Pharmaceutical Development Co., Ltd., Hefei (CN)

( * ) Notice: Subject to any disclaimer, the term of this patent is extended or adjusted under 35 U.S.C. 154(b) by 191 days.

(21) Appl. No.: 16/077,634

(22) PCT Filed: Mar. 2, 2017

(86) PCT No.: PCT/CN2017/075416
§ 371 (c)(1),
(2) Date: Aug. 13, 2018

(87) PCT Pub. No.: WO2017/148406
PCT Pub. Date: Sep. 8, 2017

(65) Prior Publication Data
US 2020/0115386 A1  Apr. 16, 2020

(30) Foreign Application Priority Data
Mar. 4, 2016 (CN) .......................... 201610121108.5

(51) Int. Cl.
| | | |
|---|---|---|
| C07D 495/14 | (2006.01) | |
| C07D 487/04 | (2006.01) | |
| C07D 487/16 | (2006.01) | |
| A61P 1/16 | (2006.01) | |
| A61P 37/06 | (2006.01) | |

(52) U.S. Cl.
CPC .............. *C07D 495/14* (2013.01); *A61P 1/16* (2018.01); *A61P 37/06* (2018.01); *C07D 487/04* (2013.01); *C07D 487/16* (2013.01)

(58) Field of Classification Search
CPC .............. A61K 31/5513; A61K 31/553; A61K 31/554; A61P 1/16; A61P 37/06; C07D 487/04; C07D 487/16; C07D 491/147; C07D 495/14
See application file for complete search history.

(56) References Cited

U.S. PATENT DOCUMENTS

2008/0242608 A1   10/2008  Bonni et al.

FOREIGN PATENT DOCUMENTS

| WO | WO2010080712 A2 | | 7/2010 |
| WO | WO 2014/145909 | * | 9/2014 |
| WO | WO2014145909 A2 | | 9/2014 |

OTHER PUBLICATIONS

Extended European Search Report for European Patent Application No. 17759257.3; dated Jul. 10, 2019.
International Search Report; dated Apr. 28, 2017 for PCT Application No. PCT/CN2017/075416.
Manning, Gerard, et al. "The protein kinase complement of the human genome." Science 298.5600 (2002): 1912-1934.
Lehtinen, Maria K., et al. "A conserved MST-FOXO signaling pathway mediates oxidative-stress responses and extends life span." Cell 125.5 (2006): 987-1001.
Mou, Fan, et al. "The Mst1 and Mst2 kinases control activation of rho family GTPases and thymic egress of mature thymocytes." Journal of Experimental Medicine 209.4 (2012): 741-759.
Zhang, Jianming, Priscilla L. Yang, and Nathanael S. Gray. "Targeting cancer with small molecule kinase inhibitors." Nature Reviews Cancer 9.1 (2009): 28.
Zhao, Bin, Karen Tumaneng, and Kun-Liang Guan. "The Hippo pathway in organ size control, tissue regeneration and stem cell self-renewal." Nature cell biology 13.8 (2011): 877.
Zhou, Dawang, et al. "Mst1 and Mst2 maintain hepatocyte quiescence and suppress hepatocellular carcinoma development through inactivation of the Yap1 oncogene." Cancer cell 16.5 (2009): 425-438.
Zhou, Dawang. "Diversity in function and regulation of the Hippo pathway." Cell & bioscience 3.1 (2013): 34.

\* cited by examiner

*Primary Examiner* — Erich A Leeser
(74) *Attorney, Agent, or Firm* — Law offices of Datan LLC

(57) ABSTRACT

The present invention relates to compounds (I) capable of inhibiting the Mst1/2 protein kinase activity, a preparation method therefor, a pharmaceutical composition comprising the compounds, and uses of the compounds and the pharmaceutical composition comprising the compounds in the preparation of drugs for prompting repair and regeneration of tissues and organs, prompting stem cell proliferation and somatic cell dedifferentiation, immunosuppression, and preventing or treating diseases related to nervous disorders and local ischemia.

19 Claims, 6 Drawing Sheets

PYRIMIDINE SEVEN-MEMBERED-RING COMPOUNDS, PREPARATION METHOD THEREFOR, PHARMACEUTICAL COMPOSITION THEREOF, AND USES THEREOF

TECHNICAL FIELD

The present invention relates to the field of pharmaceutical chemistry, in particular, it relates to a class of compounds capable of inhibiting Mst1/2 protein kinase activity, the method for production thereof, pharmaceutical composition comprising these compounds, the use of these compounds and pharmaceutical composition for manufacturing medicament for promoting tissue or organ regeneration and repair, promoting stem cell proliferation and somatic cell differentiation, promoting immune suppression, preventing or treating neurological disorder related diseases and local ischemia.

BACKGROUND TECHNOLOGY

Phosphorylation of substrates by protein kinase played a key role in cell signaling, involving almost all aspects of cell physiology (Science, 2002, 298, p 1912-1934). Kinase over expression and malfunction are closely associated with cancer, metabolic diseases, neurodegenerative disorders and inflammatory diseases. In 2001, the successful launch of first Bcr-Abl kinase inhibitor Gleevec® for treatment of chronic myelocytic leukemia started the era of targeted anticancer drugs (Nat. Rev. Cancer, 2009, 9, p 28-39). Over the past decade, the kinases have become the second largest drug target class for development of new drugs by pharmaceutical companies. There are more than 32 small-molecule kinase inhibitors that have been approved by the US FDA for clinic use.

Studies have shown that, Hippo signaling pathway plays an important role in regulating differentiation and proliferation of tissue stem cells, controlling organ size and maintaining tissue homeostasis (Cell Biosci, 2013, 3, p 34; Nat Cell Biol. 2011, 13 (8), p 877-83.). Conditional knockout the key kinase in Hippo signaling Mst1/2 protein kinase can promote liver regeneration (Cancer Cell, 2009, 16, p 425-438), and immunosuppression (J. Exp. Med. 2012, 209, p 741-759). Reducing Mst1/2 kinase protein level or enzymatic activity helps reducing neuronal cell death, and thus be useful for prevention and treatment of neurological disorders or neurodegenerative diseases, including Alzheimer's disease, multiple sclerosis, Parkinson's disease, stroke, etc. (Cell 2006, 125, p 987-1001); and oxidizing stress-related myocardial ischemia and peripheral ischemia (US 2008/0242608).

Thus, the development of small molecule inhibitors of Mst1/2 protein kinase will be used for treatment of Mst1/2 kinase associated diseases, including promotion of regeneration and repair of tissues and organs, immunosuppression, preventing or treating neurological disorder related diseases and local ischemia, which have significant economic and social value.

SUMMARY OF INVENTION

In order to find highly selectively Mst kinase inhibitors, after extensive research, the inventors designed and synthesized a series of structurally novel and highly safe plurality substituted pyrimidine seven member ring derivatives that inhibit Mst1/2 kinase, and studied their activity in promoting tissue regeneration and repair.

Accordingly, the present invention provides compounds having the following formula:

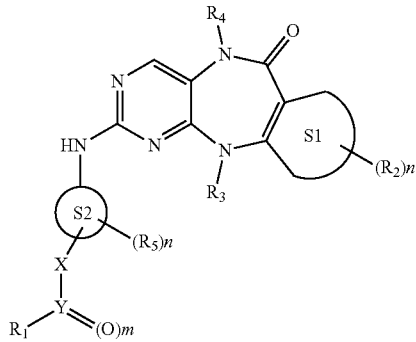

or the stereoisomer of the above compounds, a prodrug thereof, a pharmaceutically acceptable salt thereof, or a pharmaceutically acceptable solvate thereof.

More particularly, the present invention provides compounds of the following formula (I-IV):

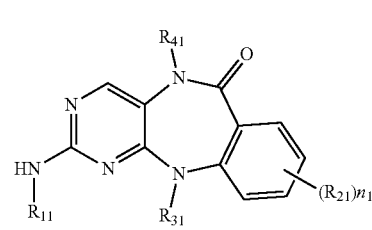

I

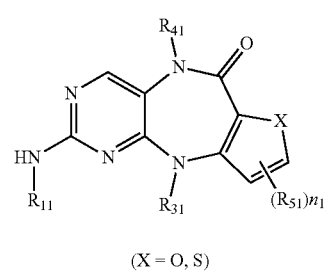

II (X = O, S)

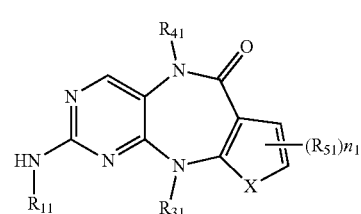

III (X = O, S)

-continued

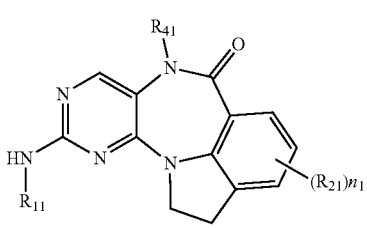

IV or a stereoisomer of the above compounds, a prodrug thereof, a pharmaceutically acceptable salt thereof, or a pharmaceutically acceptable solvate thereof.

Wherein the definition of the substituents and symbols are described in detail below.

An objective of the present invention is to provide a class of compound and stereoisomers thereof, a prodrug thereof, a pharmaceutically acceptable salt thereof, or a pharmaceutically acceptable solvate thereof for inhibiting Mst1/2 kinase activity.

Another objective of the present invention is to provide a method for preparing the above compounds.

Another objective of the present invention is to provide a pharmaceutical composition comprising the above compounds.

Another objective of the present invention is to provide use of such compounds and pharmaceutical compositions comprising said compounds in manufacture medicament for promoting tissue repair and organ regeneration, promoting stem cell proliferation and somatic cell differentiation, immune suppression, prevention or treatment of neurological disorder related diseases and vascular diseases associated with local ischemia.

DETAILED DESCRIPTION

Figure 1:
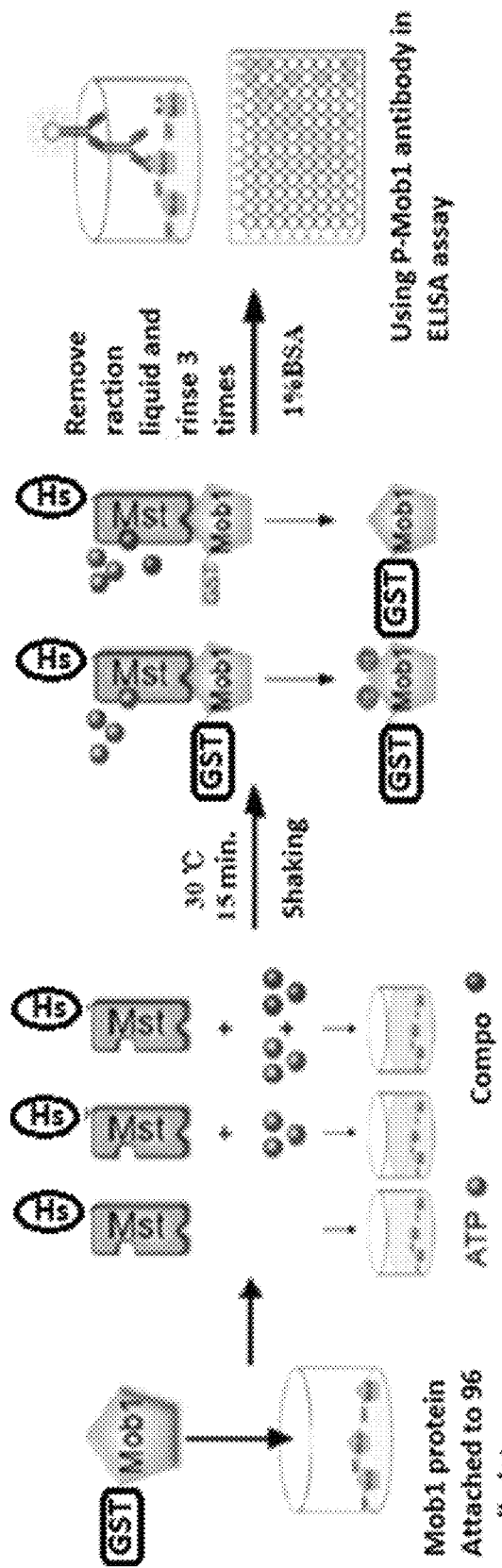
FIG. 1 is a schematic representative the enzyme-linked immunosorbent assay for measuring the Mst1/2 kinase activity.

This paper describes various specific embodiments and examples, including exemplary embodiments and definitions for understanding the present invention. While the following detailed description gives specific preferred embodiments, those skilled in the art will appreciate that these embodiments are merely exemplary, and the present invention may be practiced in other ways. For purposes of determining infringement, the scope of the present invention encompasses any one or more of the appended claims, including equivalents of the substance, elements or limitations as described herein.

The present invention is achieved by the following technical solutions.

A first aspect, the present invention provides a compound represented by the following general formula:

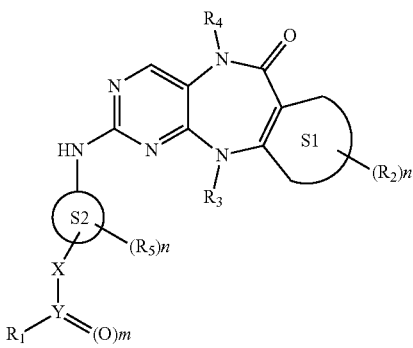

among them, $R_1$ is selected:
1) C1-C6 alkyl, optionally substituted by halogen, nitro, cyano; C1-C6 alkyl group containing oxygen; C3-C7 cycloalkyl, which is optionally substituted by halogen, nitro, cyano; —O—C1-C6 alkyl, optionally substituted by halogen, nitro, amino, cyano; —O—C3-C7 cycloalkyl, which is optionally substituted with halogen, nitro, amino, cyano; C6-C10 aryl, which is optionally substituted by halogen, nitro, amino, cyano; —O—C6-C10 aryl, which is optionally substituted by halogen, nitro, amino, cyano; C2-C6 alkenyl group;
2) 3-N, N-dimethylamino-propenyl, 3-pyrrolidin-propenyl;
3) amino, cyclopropylamino, cyclobutylamino, cyclopentylamino, cyclohexylamino, N, N-dimethylamino, N, N-diethylamino, N, N-diisopropylamino, 2-N, N-dimethyl-ehthylamino, 2-hydroxyethylamino, 2-morpholinyl-ethylamino, 2-thiomorpholinyl ethylamino, 2-(4-N-methyl piperazinyl) ethylamino, 3-N, N-dimethyl-aminopropyl amino, 3-N, N-diethyl aminopropyl amino, 3-N, N-diisopropyl-aminopropyl amino, amino-3-hydroxylpropyl, 3-morpholinyl-propylamino, 3-thiomorpholinyl propylamino, 3-(4-N-methylpiperazinyl) propylamino, N-methylpiperidinyl-4-amino, N-ethylpiperidiny-4-amino, N-isopropyl-piperidinyl-4-amino, N-acetyl-piperidinyl-4-amino;
4) hydroxyl, 2-N,N-dimethylaminoethoxyl, 2-N, N-diethyl-aminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monohalogen-substituted phenylmethoxyl, homodihalogen-substituted phenylmethoxyl, heterodihalogen-substituted phenylmethoxyl;

5) selected from the group of five- or six-membered heterocyclic rings comprising one or a more of N, S and O heteroatoms, said five- or six-membered heterocyclic rings are optionally substituted with C1-C6 alkyl, C1-C6 alkoxy, hydroxy, amino, C1-C6 acyl, cyano, or heterocyclic group, including but not limited to: piperidinyl, 4-N, N-dimethylamino-piperidinyl, 4-N, N-diethylamino-piperidinyl, 4-N, N-diisopropylamino piperidinyl, 4-hydroxypiperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N,N-diethyl-propyl) piperazinyl) piperidinyl, 4-(pyrrolidinyl) piperidinyl, 4-(3-N, N-dimethyl-pyrrolidinyl) piperidinyl;

N-methyl-piperazinyl, N-ethyl-piperazinyl, N-isopropyl-piperazinyl, N-acetyl-piperazinyl, N-tert formyl piperazinyl, N-methylsulfonyl-piperazinyl piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;

morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl;

$R_2$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamino, ethylsulfonamino, propylsulfonamido, isopropylsulfonamido, dimethyl phosphinyl, diethyl phosphinyl, diisopropyl phosphinyl;

$R_3$ is selected from: hydrogen; C1-C6 alkyl, optionally substituted by halogen, nitro, amino, cyano; C3-C7 cycloalkyl, which is optionally substituted with halogen, nitro, amino, cyano; alternatively, $R_3$ may form a five-member ring with its connected N atom and C atom in the Si ring;

$R_4$ is selected from: hydrogen; C1-C6 alkyl, optionally substituted by halogen, nitro, amino, cyano; C3-C7 cycloalkyl, which is optionally substituted with halogen, nitro, amino, cyano;

$R_5$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

X=O, NH or a direct bond;
Y=S, C, P, N, OH, $NH_2$ or $CH_2$;
m=0, 1 or 2;
n=0, 1, 2, 3 or 4;

is aryl or heteroaryl group fused with a seven membered two-nitrogen heterocyclic ring;

is aryl or heteroaryl;
or a stereoisomer of the above compounds, a prodrug thereof, a pharmaceutically acceptable salt thereof, or a pharmaceutically acceptable solvate thereof.

In some embodiments, $R_1$ is selected from:
1) C1-C6 alkyl, optionally substituted by halogen, nitro, cyano; C1-C6 alkyl containing oxygen; C3-C7 cycloalkyl, which is optionally substituted by halogen, nitro, cyano; —O—C1-C6 alkyl, optionally substituted by halogen, nitro, amino, cyano; —O—C3-C7 cycloalkyl, optionally substituted with halogen, nitro, amino, cyano; C6-C10 aryl, optionally substituted by halogen, nitro, amino, cyano; —O—C6-C10 aryl, which is optionally substituted by halogen, nitro, amino, cyano; C2-C6 alkenyl; 3-N, N-dimethylamino-propenyl, 3-pyrrolidinyl-propenyl; amino; hydroxyl;
2) selected from the group of five- or six-membered heterocyclic rings comprising one or a plurality of N, S and O heteroatoms, said five- or six-membered heterocyclic rings are optionally substituted with C1-C6 alkyl, C1-C6 alkoxyl, hydroxyl, amino, C1-C6 acyl, cyano, heterocyclic group, including but not limited to: piperidinyl, 4-N, N-dimethylamino-piperidinyl, 4-N, N-diethylamino-piperidinyl, 4-N, N-diisopropylamino piperidinyl, 4-hydroxypiperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxyethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl; N-methyl-piperazinyl, N-ethyl-piperazinyl, N-isopropyl-piperazinyl, N-acetyl-piperazinyl, N-tert butoxyl formyl piperazinyl, N-methylsulfonyl-piperazinyl piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl.

In some embodiments, $R_2$ is selected from: hydrogen, halo, nitro, amino, cyano; C1-C6 alkyl, optionally substituted by halogen, nitro, amino, cyano; —O—C1-C6 alkyl, optionally substituted by halogen, nitro, amino, cyano; C1-C6 alkyl groups containing oxygen.

In some embodiments, $R_3$ is selected from: hydrogen; C1-C6 alkyl; C3-C7 cycloalkyl.

In some embodiments, $R_4$ is selected from: hydrogen; C1-C6 alkyl; C3-C7 cycloalkyl.

In some embodiments, $R_5$ is selected from: hydrogen, halo, nitro, amino, cyano; C1-C6 alkyl, optionally substituted by halogen, nitro, amino, cyano; C3-C7 cycloalkyl group, which is optionally substituted by halogen, nitro, amino, cyano.

In some embodiments,

is benzene ring, a thiophene ring, a furan ring, a pyridine ring, an oxazole ring, or thiazolyl ring fused with a seven membered two nitrogen heterocyclic ring group.

In some embodiments,

is a benzene ring or a pyrazole ring.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A second aspect, the present invention provides compounds with the following formulas I, II, III, IV:

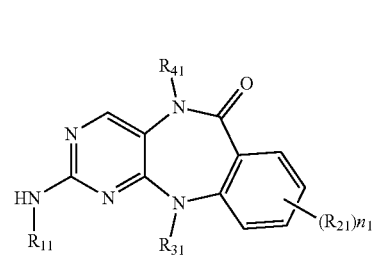

I

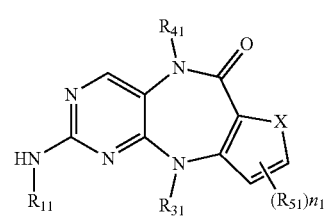

II (X = O, S)

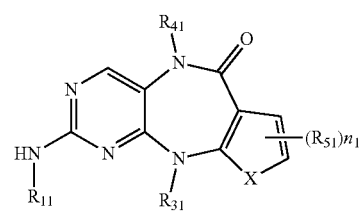

III (X = O, S)

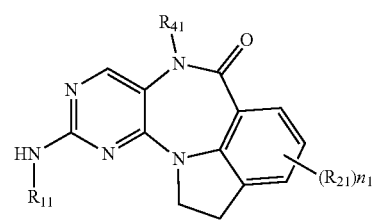

IV wherein: n1 is selected from 0, 1, 2, 3 or 4;

$R_{11}$ is selected from:

1) C1-C6 alkyl, optionally substituted with halogen, amino, nitro, cyano; C1-C6 alkyl containing oxygen; C3-C7 cycloalkyl, which is optionally substituted with halogen, amino, nitro, cyano; C6-C10 aryl, optionally substituted by halogen, nitro, amino, hydroxy, cyano; C3-C6 alkenyl;

2) 2-N, N-dimethylaminoethyl, 2-hydroxyethyl, 2-N, N-diethylaminoethyl, 2-N, N-diisopropylamino ethyl, 2-morpholinyl ethyl, 2-thiomorpholinyl ethyl, 2-(4-N-piperazinylmethyl) ethyl, 3-N, N-dimethylaminopropyl, 3-N, N-diethylaminopropyl, 3-N, N-diisopropyl-aminopropyl, 3-morpholinyl propyl, 3-thiomorpholinyl propyl, 3-(4-N-methylpiperidinyl) propyl, 4-N, N-dimethylamino-cyclohexyl, 4-N, N-diethylamino cyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-tert-butoxyl formyl-4-piperidinyl)-4-pyrazolyl;

3)

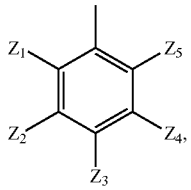

wherein $Z_1$, $Z_2$, $Z_3$, $Z_4$, $Z_5$ are each independently selected from:

(1) hydrogen, halogen, nitro, amino, hydroxy, cyano, (2) C1-C6 alkyl, C1-C6 alkoxy, C1-C6 alkyl containing oxygen, C1-C6 alkyl containing fluorine, C1-C6 alkoxy containing fluorine, 4-piperidinyl, N-methyl yl-4-piperidinyl, (3) N, N-dimethylamino, N, N-diethylamino, N, N-diisopropylamino, 2-N, N-dimethylaminoethylamino, 2-morpholino ethylamino, 2-ethylamino thiomorpholinyl, 2-(4-N-methylpiperazinyl) ethylamino, 3-N, N-dimethylaminopropyl amino, 3-N, N-diethylaminopropyl-amino, 3-N, N-diisopropylamino propylamino, 3-morpholin-propylamino, 3-thiomorpholinyl propylamino, 3-(4 N-methylpiperazinyl) propylamino, N-methylpiperidinyl-4-amino, N-ethylpiperidinyl-4-amino, N-isopropyl-piperidinyl-4-amino, (4) 2-N, N-dimethylaminoethoxyl, 2-N, N-diethyl-aminoethoxy, 2-N, N-diisopropyl-aminoethoxyl, 2-(N-methylpiperazinyl) ethoxyl, 2-(N-acetyl-piperazinyl) ethoxyl, 2-morpholino-ethoxyl, 2-thiomorpholino-ethoxyl, 2-piperidinyl ethoxyl, 3-N, N-dimethylamino-propoxyl, 3-N, N-diethyl-amino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monohalogen-substituted phenylmethoxyl, homodihalogen-substituted phenylmethoxyl, heterodihalogen-substituted phenylmethoxyl, (5) piperidinyl, 4-N, N-dimethylamino-piperidinyl, 4-N, N-diethylamino-piperidinyl, 4-N, N-diisopropylamino piperidinyl, 4-hydroxy piperidinyl, morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl, N-methyl-piperazinyl, N-ethyl-piperazinyl, N-isopropyl-piperazinyl, N-acetyl-piperazinyl, N-tert-butoxyl formyl piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethyl-ethyl) piperazinyl, N-(2-N, N-diethyl-ethyl) piperazinyl, N-(3-N, N-dimethylpropyl) piperazinyl, N-(3-N, N-diethyl-propyl) piperazinyl, 2-oxo-piperazinyl, 2-oxo-piperazin-4-yl, imidazolyl, 4-imidazolyl, (6) 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-t-butoxyl-formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl, N—(N-methyl-4-piperidinyl) piperazinyl, N—(N-ethyl-4-piperidinyl) piperazinyl, (7) hydroxy sulfonyl, aminosulfonyl, sulfonyl methylamino, ethylamino sulfonyl group, a sulfonyl group propylamino, isopropylamino-sulfonyl, aminosulfonyl cyclopropyl, cyclobutyl aminosulfonyl, cyclopentyl aminosulfonyl, piperidinyl-sulfonyl, 4-hydroxyl-piperidinyl-1-sulfonyl, 4-N, N-dimethyl-piperidinyl-1-sulfonyl, 4-N, N-diethyl-piperidinyl-1-sulfonyl, pyrrolidinyl-1-sulfonyl, 3-N, N-dimethyl-pyrrolidinyl-1-sulfonyl, 3-N, N-diethyl-pyrrolidinyl-1-sulfonyl, N-methyl-piperazinyl-sulfonyl, N-ethylpiperazinyl-1-sulfonyl, N-acetyl-piperazinyl-1-sulfonyl, N-tert-butoxylformyl-piperazinyl-1-sulfonyl, N-(2-hydroxylethyl) piperazinyl-1-sulfonyl, N-(2-cyanoethyl) piperazinyl-1-sulfonyl, N-(2-N, N-dimethyl ethyl) piperazinyl-1-sulfonyl, N-(2-N, N-diethyl-ethyl) piperazinyl-1-sulfonyl, N-(3-hydroxylpropyl) piperazinyl-1-sulfonyl, N-(3-N, N-dimethylamino-propyl) piperazinyl-1-sulfonyl, N-(3-N, N-diethylamino-propyl) piperazinyl-1-sulfonyl, morpholinyl-1-sulfonyl, 3,5-dimethyl-morpholinyl-1-sulfonyl, 4-(N-methyl-1-piperazinyl) piperidinyl-1-sulfonyl, 4-(N-ethyl-1-piperazinyl) piperidinyl-1-sulfonyl, 4-(N-acetyl-1-piperazinyl) piperidinyl-sulfonyl, N—(N-methyl-4-piperidinyl) piperazinyl-1-sulfonyl, (8) amino formyl, methylamino formyl, ethylamino formyl, propylamino formyl, isopropylamino formyl, cyclopropylamino formyl, cyclobutylamino formyl, cyclopentylamino formyl, piperidinyl-1-formyl, 4-hydroxy-piperidinyl-1-formyl, 4-N, N-dimethyl-piperidinyl-1-formyl, 4-N, N-two ethylpiperidinyl-1-formyl, tetrahydropyrrolyl-1-formyl, 3-N, N-dimethyl-tetrahydropyrrolyl-1-formyl, 3-N, N-diethyl-tetrahydropyrrolyl-1-formyl, N-methyl-piperazinyl-1-formyl, N-ethyl-piperazinyl-1-formyl, N-acetyl-piperazinyl-1-formyl, N-tert-butoxyl-formyl-piperazinyl-1-formyl, N-(2-hydroxyethyl) piperazinyl-1-formyl, N-(2-cyanoethyl) piperazinyl-1-formyl, N-(2-N, N-dimethyl-ethyl) piperazinyl-1-formyl, N-(2-N, N-diethyl-ethyl) piperazinyl-1-formyl, N-(3-hydroxypropyl) piperazinyl-1-formyl, N-(3-N, N-dimethyl-propyl) piperazinyl-1-formyl, N-(3-N, N-diethyl propyl) piperazinyl-1-formyl, morpholinyl-1-formyl, 3,5-dimethyl-morpholinyl-1-formyl, 4-(N-methyl-1-piperazinyl) piperidinyl-1-formyl, 4-(N-ethyl-1-piperazinyl) piperidinyl-1-formyl, 4-(N-acetyl-1-piperazinyl) piperidinyl-1-formyl, N—(N-methyl-4-piperidinyl) piperazinyl-1-formyl, (9) hydroxyl formyl, methoxyl formyl, ethoxyl formyl, propoxyl formyl, isopropoxyl formyl, n-butoxyl formyl, isobutoxy formyl, t-butoxyl formyl,

(10) amino formamido, methylamino formamido, ethylamino formamido, propylamino formamido, isopropylamino formamido, cyclopropylamino formamido, cyclobutylamino formamido, cyclopentylamino formamido, piperidinyl-1-formamido, 4-hydroxy-piperidinyl-1-formamido, 4-N, N-dimethyl-piperidinyl-1-formamido, 4-N, N-diethyl-piperidinyl-1-formamido, tetrahydropyrrolyl-1-formamido, 3-N, N-dimethyl-tetrahydropyrrolyl-1-formamido, 3-N, N-diethyl-tetrahydropyrrolyl-1-formamido, N-methyl-piperazinyl-1-formamido, N-ethyl-piperazinyl-1-formamido, N-acetyl-piperazinyl-1-formamido, N-tert-butoxyl formyl-piperazinyl-1-formamido, N-(2-hydroxyethyl) piperazinyl-1-formamido, N-(2-cyanoethyl) piperazinyl-1-formamido, N-(2-N, N-dimethyl-ethyl) piperazinyl-1-formamido, N-(2-N, N-diethyl-ethyl) piperazinyl-1-formamido, N-(3-hydroxypropyl) piperazinyl-1-formamido, N-(3-N, N-dimethyl-propyl) piperazinyl-1-formamido, N-(3-N, N-diethyl-aminopropyl) piperazinyl-1-formamido, morpholinyl-1-formamido, 3,5-dimethyl-morpholinyl-1-formamido, 4-(N-methyl-1-piperazinyl) piperidinyl-1-formamido, 4-(N-ethyl-1-piperazinyl) piperidinyl-1-formamido, 4-(N-acetyl-1-piperazinyl) piperidinyl-1-formamido, N—(N-methyl-4-piperidinyl) piperazinyl-1-formamido; or

(11) amino acetamido, N-tert-butoxyl formyl acetamido, N-acetylamino acetamido, acrylamido, cyclopropylamido, chloroacetamido, bromoacetamido, piperidinyl acetamido, 4-hydroxy piperidinyl acetamido, 4-N, N-dimethyl-piperidinyl-acetamido, 4-N, N-diethyl-piperidinyl acetamido, tetrahydropyrrolyl acetamido, 3-N, N-dimethyl-tetrahydropyrrolyl acetamido, 3-N, N-diethyl-tetrahydropyrrolyl-acetamido, N-methyl-piperazinyl acetamido, N-ethyl piperazinyl-acetamido, N-acetyl-piperazinyl acetamido, N-tert-butoxy formyl-piperazinyl acetamido, N-(2-hydroxyethyl) piperazinyl acetamido, N-(2-cyanoethyl) piperazinyl acetamido, N-(2-N, N-dimethylethyl) piperazinyl acetamido, N-(2-N, N-diethyl-ethyl) piperazinyl acetamido, N-(3-hydroxylpropyl) piperazinyl acetamido, N-(3-N, N-dimethyl-propyl) piperazinyl acetamido, N-(3-N, N-diethyl-propyl) piperazinyl acetamido, morpholinyl acetamido, 3,5-dimethyl-morpholinyl-acetamido, 4-(N-methyl-1-piperazinyl) piperidinyl acetamido, 4-(N-ethyl-1-piperazinyl) piperidinyl acetamido, 4-(N-acetyl-1-piperazinyl) piperidinyl acetamido, N—(N-methyl-4-piperidinyl) piperazinyl acetamido, 4-(tetrahydropyrrolyl) piperidinyl acetamido; 2-methylamino acetamido, 2-(1-methylethyl) amino acetamido; N-benzyloxy-formyl-2-methylamino-acetamido;

(12) $Z_2$ and $Z_3$ may form a substituted or unsubstituted oxygen-containing five- or six-membered ring; the substituents may be selected from the same substituents of $Z_1$,

(13) $Z_2$ and $Z_3$ may form a substituted or unsubstituted nitrogen-containing five- or six-membered ring; the substituents may be selected from the same substituents of $Z_1$,

4)

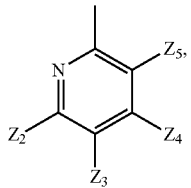

wherein $Z_2$, $Z_3$, $Z_4$, $Z_5$ are the same as the definition 3) above;

5)

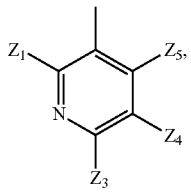

wherein $Z_1$, $Z_3$, $Z_4$, $Z_5$ are the same as the definition 3) above;

$R_{21}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethylsulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formy, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{31}$ is selected from:
Hydrogen; C1-C6 alkyl, optionally substituted by halogen, nitro, amino, cyano; C3-C7 cycloalkyl, which is optionally substituted by halogen, nitro, amino, cyano;

$R_{41}$ is selected from:
hydrogen; C1-C6 alkyl, optionally substituted by halogen, nitro, amino, cyano; C3-C7 cycloalkyl, which is optionally substituted by halogen, nitro, amino, cyano;

$R_{51}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl; or a stereoisomer of the above compounds, a prodrug thereof, a pharmaceutically acceptable salt thereof, or a pharmaceutically acceptable solvate thereof.

In some embodiments, $R_{11}$ is selected from:
1) C1-C6 alkyl, optionally substituted by halogen, nitro, cyano; C1-C6 alkyl group containing oxygen; C3-C7 cycloalkyl, which is optionally substituted by halogen, nitro, cyano; C6-10 aryl, optionally substituted by halogen, nitro, amino, hydroxy, cyano;
2) 2-N, N-dimethylaminoethyl, 2-hydroxyethyl, 2-N, N-diethylaminoethyl, 2-N, N-diisopropylamino ethyl, 2-morpholinyl ethyl, 2-thiomorpholinyl ethyl, 2-(4-N-piperazinyl-methyl) ethyl, 3-N, N-dimethylaminopropyl, 3-N, N-diethylaminopropyl, 3-N, N-diisopropyl-aminopropyl, 3-morpholinyl propyl, 3-thiomorpholinyl propyl, 3-(4-N-methylpiperidine 1) propyl, 4-N, N-dimethylamino-cyclohexyl, 4-N, N-diethylamino cyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-tert-butoxyl formyl-4-piperidinyl)-4-pyrazolyl.

In some embodiments, $Z_3$ of $R_{11}$ is selected from amino, aminosulfonyl, methylamino sulfonyl, cyclopropylamino sulfonyl, piperidinyl-sulfonyl, 4-hydroxypiperidinyl-1-sulfonyl, 4-N, N-dimethyl-piperidinyl-1-sulfonyl, pyrrolidinyl-1-sulfonyl, 3-N, N-dimethyl-pyrrolidinyl-1-sulfonyl, N-methyl-piperazinyl-sulfonyl, N-ethyl-piperazinyl-1-sulfonyl, morpholinyl-1-sulfonyl, methylsulfonamido, ethylsulfonamido, isopropyl sulfonamido, vinylsulfonamido, formic acid group, amino formyl, methylamino formyl, ethylamino formyl, isopropylamino formyl, cyclopropylamino formyl, piperidin-1 formyl, 4-hydroxyl-piperidinyl-1-formyl, 4-N, N-dimethyl-piperidinyl-1-formyl, tetrahydropyrrolyl-1-formyl, 3-N, N-dimethyl-tetrahydropyrrolyl-1-formyl, N-methyl-piperazinyl-1-formylyl, N-ethyl-piperazinyl-1-formyl, N-acetyl-piperazinyl-1-formyl, morpholinyl-1-formyl, 4-(N-methyl-1-piperazinyl) piperidinyl-1-formyl, 4-(N-ethyl-1-piperazinyl) piperidinyl-1-formyl, 4-(N-acetyl-1-piperazinyl) piperidinyl-1-formyl, N—(N-methyl-4-piperidinyl) piperazinyl-1-formyl, chloroacetamido, bromoacetamido, acrylamido.

In some embodiments, $R_{21}$ is selected from: hydrogen, halo, nitro, amino, cyano; C1-C6 alkyl, optionally substituted by halogen, nitro, amino, cyano; —O—C1-C6 alkyl, optionally substituted by halogen, nitro, amino, cyano; C1-C6 alkyl containing oxygen.

In some embodiments, $R_{31}$ is selected from: hydrogen; C1-C6 alkyl; C3-C7 cycloalkyl.

In some embodiments, $R_{41}$ is selected from: hydrogen; C1-C6 alkyl; C3-C7 cycloalkyl.

In some embodiments, $R_{51}$ is selected from: hydrogen, halo, nitro, amino, cyano; C1-C6 alkyl, optionally substituted by halogen, nitro, amino, cyano; —O—C1-C6 alkyl optionally substituted by halogen, nitro, amino, cyano; C1-C6 alkyl containing oxygen.

In some application scenarios, n1 is selected from 0, 1, 2, 3.

In some preferred embodiments, n1 is selected from 0, 1, 2.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A third aspect, the present invention provides a compound represented by the following structural formula:

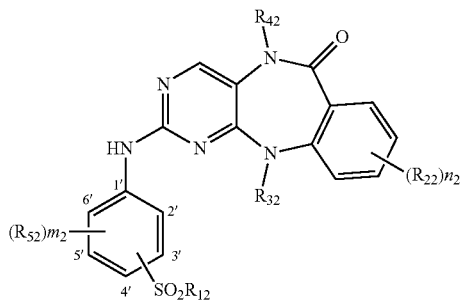

I-1 among them,
m2 is selected from 0, 1, 2, 3 or 4;
n2 is selected from 0, 1, 2, 3 or 4;

$R_{12}$ is selected from:
1) selected from the group of five membered or six-membered heterocyclic rings comprising one or more N, O and S heteroatoms, the five membered or six-membered heterocyclic rings are optionally substituted with C1-C6 alkyl, C1-C6 alkoxy, hydroxy, amino, alkylamino, dialkylamino, C1-C6 acyl, cyano, optionally substituted C1-C6 alkyl, —O—C1-C6 alkyl, hydroxy, hydroxy C1-C6 alkyl, C1-C6 acyl, alkylamino, dialkylamino substituted heterocyclic group, including but not limited to: 4-N, N-dimethylamino-piperidinyl, 4-N, N-diethylamino-piperidinyl, 4-N, N-diisopropylamino-piperidinyl, 4-hydroxy-piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;
2) amino, cyclopropylamino, cyclobutylamino, cyclopentylamino, cyclohexylamino, N, N-dimethylamino, N, N-diethylamino, N, N-diisopropylamino, 2-N, N-dimethylamino-ethylamino, 2-hydroxyethylamino, 2-morpholinyl-ethylamino, 2-(4-N-methylpiperazinyl) ethylamino, 3-N, N-dimethylamino-propylamino, 3-N, N-diethylamino-propylamino, 3-N, N-diisopropylamino-propylamino, 3-hydroxy-propylamino, 3-morpholinyl-propylamino, 3-(4-N-methylpiperazinyl) propylamino, N-methylpiperidinyl-4-amino, N-ethylpiperidinyl-4-amino, N-isopropyl piperidinyl-4-amino, N-acetylpiperidinyl-4-amino; N-methyl-piperazinyl, N-ethyl-piperazinyl, N-isopropyl-piperazinyl, N-acetyl piperazinyl, N-tert-butoxyl formyl-piperazinyl, N-methylsulfonyl-piperazinyl, N-(2-hydroxyl-ethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl aminoethyl) piperazinyl, N-(3-N, N-dimethyl-propyl) piperazinyl, N-(3-N, N-diethyl-propyl) piperazinyl, 2-oxo-piperazin-4-yl, N—(N-Methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl;
3) C1-C6 alkyl, optionally substituted by halogen, nitro, cyano;
4) C3-C7 cycloalkyl, which is optionally substituted by halogen, nitro, cyano;
5) —O—C1-C6 alkyl, optionally substituted by halogen, nitro, amino, cyano;
6) —O—C3-C7 cycloalkyl, which is optionally substituted by halogen, nitro, amino, cyano;
7) C6-C10 aryl, which is optionally substituted by halogen, nitro, amino, cyano; —O—C6-C10 aryl group, which is optionally substituted by halogen, nitro, amino, cyano;
8) C2-C6 alkenyl;
9) hydroxyl, 2-N, N-dimethylaminoethoxyl, 2-N, N-diethylaminoethoxyl, 2-N, N-diisopropyl-aminoethoxyl, 2-(N-methylpiperazine-yl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monohalogen-substituted phenyl-methoxyl, homodihalogen substituted phenyl methoxyl, heterodihalogen-substituted phenylmethoxyl;

$R_{22}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamiso, ethylsulfonamiso, propylsulfonamiso, isopropylsulfonamiso, dimethyl phosphinyl, diethyl phosphinyl, diisopropyl phosphinyl;

$R_{32}$ is selected from: hydrogen; C1-C6 alkyl, optionally substituted by halogen, nitro, amino, cyano; C3-C7 cycloalkyl, which is optionally substituted with halogen, nitro, amino, cyano;

$R_{42}$ is selected from: hydrogen; C1-C6 alkyl, optionally substituted by halogen, nitro, amino, cyano;
C3-C7 cycloalkyl, which is optionally substituted with halogen, nitro, amino, cyano;

$R_{52}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropyl aminosulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl; Or a stereoisomer of the above compounds, a prodrug thereof, a pharmaceutically acceptable salt thereof, or a pharmaceutically acceptable solvate thereof.

In some embodiments, $R_{12}$ is selected from:
1) C1-C6 alkyl, C3-C7 cycloalkyl;
2) amino, cyclopropylamino, cyclopentylamino, cyclohexylamino, N, N-dimethylamino, N, N-diethylamino, N, N-diisopropylamino, 2-N, N-dimethylamino, diethylamino, 2-hydroxyethylamino, 2-morpholinyl-ethylamino, 2-(4-N-piperazinyl-methyl) ethylamino, N-methylpiperidinyl-4-amino, N-ethylpiperidinyl-4-amino, N-isopropyl-piperidinyl-4-amino, N-acetyl-piperidinyl-4-amino;
4) hydroxyl, 2-N, N-dimethylaminoethoxyl, 2-N, N-diethyl-aminoethoxyl, 2-N, N-diisopropyl-aminoethoxyl, 2-(N-methylpiperazine-yl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl methoxyl, 3-pyridyl-methoxyl, 4-pyridyl-methoxyl;
5) piperidinyl, 4-N, N-dimethylamino-piperidinyl, 4-hydroxypiperidinyl, 4-(N-methylpiperazinyl) piperidinyl, 4-(N-ethyl-piperazinyl) piperidinyl, 4-(N-acetyl-piperazinyl) piperidinyl, 4-(N-tert-butyoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(pyrrolidinyl) piperidinyl, 4-(3-N, N-dimethyl-pyrrolidinyl) piperidinyl;
6) N-methyl-piperazinyl, N-ethyl-piperazinyl, N-isopropyl-piperazinyl, N-acetyl-piperazinyl, N-(2-hydroxyethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;
7) morpholinyl, 3,5-dimethyl morpholinyl, thiomorpholinyl, tetrahydropyrrolyl, 3-N, N-dimethyl-tetrahydro pyrrolyl, 3-N, N-diethyl tetrahydro pyrrolyl.

In some preferred embodiments, $R_{12}$ is selected from
1) methyl, ethyl, isopropyl, trifluoromethyl;
2) amino, cyclopropylamino, N, N-dimethylamino, N, N-diethylamino, N, N-diisopropylamino;
4) hydroxyl
5) piperidinyl, 4-N, N-dimethylamino-piperidinyl, 4-hydroxypiperidinyl, 4-(N-methylpiperazinyl) piperidinyl, 4-(tetrahydro-pyrrolyl) piperidinyl, 4-(3-N, N-dimethyl-pyrrolidinyl) piperidinyl;
6) N-methyl-piperazinyl, N-ethyl-piperazinyl, N-isopropyl-piperazinyl, N-acetyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;
7) morpholino, 3,5-dimethyl morpholinyl, thiomorpholinyl, tetrahydro pyrrolyl, 3-N, N-dimethyl-tetrahydropyrrolyl, 3-N, N-diethyl tetrahydropyrrolyl.

In some embodiments, $R_{22}$ is selected from: hydrogen, halo, nitro, amino, cyano, C1-C6 alkyl, said C1-C6 alkyl optionally substituted by halogen, nitro, amino, cyano; —O—C1-C6 alkyl, optionally substituted by halogen, nitro, amino, cyano.

In some preferred embodiments, $R_{22}$ is selected from: hydrogen, halogen, cyano, C1-C6 alkyl, said C1-C6 alkyl optionally substituted by halogen, nitro, amino, cyano.

In some more preferred embodiments, $R_{22}$ is selected from: hydrogen, fluoro, chloro, methyl.

In some embodiments, $R_{32}$ is selected from: hydrogen; C1-C6 alkyl; C3-C7 cycloalkyl.

In some preferred embodiments, $R_{32}$ is selected from: hydrogen, methyl, ethyl, isopropyl, cyclopropyl or cyclopentyl.

In some embodiments, $R_{42}$ is selected from: hydrogen; C1-C6 alkyl; C3-C7 cycloalkyl.

In some preferred embodiments, $R_{42}$ is selected from: hydrogen, methyl, ethyl, isopropyl, cyclopropyl or cyclopentyl.

In some embodiments, $R_{52}$ is selected from: hydrogen, halo, nitro, amino, cyano; C1-C6 alkyl, optionally substituted by halogen, nitro, amino, cyano; C3-C7 cycloalkyl group, which is optionally substituted by halogen, nitro, amino, cyano.

In some preferred embodiments, $R_{52}$ is selected from: hydrogen, fluoro, chloro, amino, methyl, trifluoromethyl.

In some embodiments, m2 is selected from 0, 1, 2, 3.

In some preferred embodiments, m2 is selected from 0, 1, 2.

In some embodiments, n2 is selected from 0, 1, 2, 3.

In some preferred embodiments, n2 is selected from 0, 1, 2.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A fourth aspect, the present invention provides a compound represented by the following structural formula:

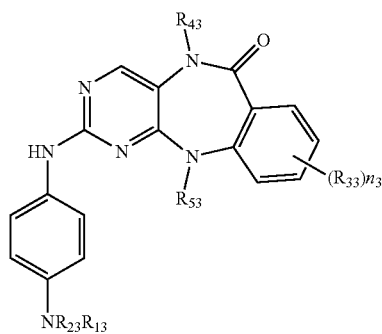

I-2 among them, n3 is selected from 0, 1, 2, 3 or 4;

$R_{23}$ is —$SO_2X$, wherein X is selected from: hydroxy; C1-C6 alkyl, optionally substituted by halogen, nitro, amino, cyano; C3-C7 cycloalkyl, which is optionally substituted with halogen, nitro, amino, cyano;

$R_{13}$ is selected from: hydrogen; C1-C6 alkyl, optionally substituted by halogen, nitro, amino, cyano; C3-C7 cycloalkyl, which is optionally substituted with halogen, nitro, amino, cyano;

$R_{33}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropyl aminoformyl, cyclobutyl aminoformyl, cyclopentylaminoformyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{53}$ is selected from: hydrogen; C1-C6 alkyl, optionally substituted by halogen, nitro, amino, cyano; C3-C7 cycloalkyl, which is optionally substituted with halogen, nitro, amino, cyano;

$R_{43}$ is selected from: hydrogen; C1-C6 alkyl, optionally substituted by halogen, nitro, amino, cyano; C3-C7 cycloalkyl, which is optionally substituted with halogen, nitro, amino, cyano;

Or a stereoisomer of the above compounds, a prodrug thereof, a pharmaceutically acceptable salt thereof, or a pharmaceutically acceptable solvate thereof.

In some embodiments, $R_{23}$ is —$SO_2X$, wherein X is selected from: hydroxy; C1-C6 alkyl, optionally substituted by halogen, nitro, amino, cyano.

In some embodiments, $R_{13}$ is selected from: hydrogen; C1-C6 alkyl, optionally substituted by halogen, nitro, amino, cyano.

In some embodiments, $R_{33}$ is selected from: hydrogen, halo, nitro, amino, cyano, C1-C6 alkyl, optionally substituted by halogen, nitro, amino, cyano; C3-C7 cycloalkyl, which is optionally substituted by halogen, nitro, amino, cyano.

In some preferred embodiments, $R_{33}$ is selected from: hydrogen, halogen, C1-C6 alkyl, optionally substituted by halogen, nitro, amino, cyano.

In some embodiments, $R_{53}$ is selected from: hydrogen; C1-C6 alkyl, C3-C7 cycloalkyl.

In some embodiments, $R_{43}$ is selected from: hydrogen; C1-C6 alkyl, C3-C7 cycloalkyl.

In some embodiments, n3 is selected from 0, 1, 2, 3.

In some preferred embodiments, n3 is selected from 0, 1, 2.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A fifth aspect, the present invention provides a compound represented by the following structural formula:

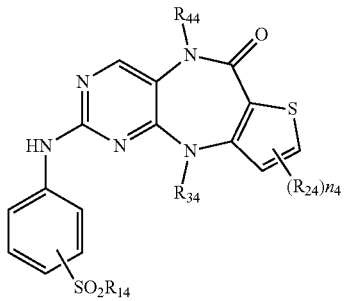

II-1 n4 is selected from 0, 1 or 2;
R$_{14}$ is selected from:
1) selected from the group of five-membered heterocyclic or six-membered heterocyclic rings comprising one or more N, O and S heteroatoms, the five-membered heterocyclic or six-membered heterocyclic rings are optionally substituted with C1-C6 alkyl, C1-C6 alkoxy, hydroxy, amino, alkylamino, dialkylamino, C1-C6 acyl, cyano, optionally substituted C1-C6 alkyl, —O—C1-C6 alkyl, hydroxyl, hydroxyl C1-C6 alkyl, C1-C6 acyl, alkylamino, dialkylamino substituted heterocyclic group,
including but not limited to: 4-N, N-dimethylamino-piperidinyl, 4-N, N-diethylamino-piperidinyl, 4-N, N-diisopropylamino-piperidinyl, 4-hydroxyl-piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxyl propyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tertahydropyrrolyl) piperidinyl, 4-(3-N, N-dimethyl-tetrahydropyrrolyl) piperidinyl;
2) amino, cyclopropylamino, cyclobutylamino, cyclopentylamino, cyclohexylamino, N, N-dimethylamino, N, N-diethylamino, N, N-diisopropylamino, 2-N, N-dimethylamino ethylamino, 2-hydroxylethylamino, 2-morpholinyl-ethylamino, 2-(4-N-methylpiperazinyl) ethylamino, 3-N, N-dimethyl-aminopropyl amino, 3-N, N-diethylamino propylamino, 3-N, N-diisopropylamino-propylamino, 3-hydroxypropyl, 3-morpholinyl-propylamino, 3-(4-N-methylpiperazinyl) propylamino, N-methyl-piperidinyl-4-amino, N-ethylpiperidinyl-4-amino, N-isopropyl piperidinyl-4-amino, N-acetylpiperidinyl-4-amino; N-methylpiperazinyl, N-ethyl-piperazinyl, N-isopropyl-piperazinyl, N-acetyl piperazinyl, N-tert-butoxyl formyl-piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl aminoethyl) piperazinyl, N-(3-N, N-dimethylpropyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl;
3) C1-C6 alkyl, optionally substituted by halogen, nitro, cyano;
4) C3-C7 cycloalkyl, which is optionally substituted by halogen, nitro, cyano;
5) —O—C1-C6 alkyl, optionally substituted by halogen, nitro, amino, cyano;
6) —O—C3-C7 cycloalkyl, which is optionally substituted by halogen, nitro, amino, cyano;
7) C6-C10 aryl, which is optionally substituted by halogen, nitro, amino, cyano; —O—C6-C10 aryl, which is optionally substituted by halogen, nitro, amino, cyano;
8) C2-C6 alkenyl;
9) hydroxyl, 2-N, N-dimethylaminoethoxyl, 2-N, N-diethylaminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monhalogen-substituted phenylmethoxyl, homodihalogen substituted phenylmethoxyl, heterodihalo-substituted phenylmethoxyl;
R$_{24}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl acetamido, propionamido, n-butylamido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;
R$_{34}$ is selected from:
hydrogen; C1-C6 alkyl, optionally substituted by halogen, nitro, amino, cyano; C3-C7 cycloalkyl, which is optionally substituted by halogen, nitro, amino, cyano;
R$_{44}$ is selected from:
hydrogen; C1-C6 alkyl, optionally substituted by halogen, nitro, amino, cyano; C3-C7 cycloalkyl, which is optionally substituted by halogen, nitro, amino, cyano;
Or a stereoisomer of the above compounds, a prodrug thereof, a pharmaceutically acceptable salt thereof, or a pharmaceutically acceptable solvate thereof.
In some embodiments, R 14 is selected from:
1) C1-C6 alkyl, C3-C7 cycloalkyl;
2) amino, cyclopropylamino, cyclopentylamino, cyclohexylamino, N, N-dimethylamino, N, N-diethylamino, N, N-diisopropylamino, 2-N, N-dimethylamino, diethylamino, 2-hydroxyethylamino, 2-morpholino-ethylamino, 2-(4-N-piperazinyl-methyl) ethylamino, N-methylpiperidinyl-4- amino, N-ethylpiperidinyl-4-amino, N-isopropyl-piperidinyl-4-amino, N-acetyl-piperidinyl-4-amino;

3) hydroxyl, 2-N, N-dimethylaminoethoxyl, 2-N, N-diethylaminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl-methoxyl;

4) piperidinyl, 4-N, N-dimethylamino-piperidinyl, 4-hydroxylpiperidinyl, 4-(N-methylpiperazinyl) piperidinyl, 4-(N-ethyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxyethyl) piperazinyl) piperidinyl, 4-(N-(2-cyanoethyl) piperazinyl) piperidinyl, 4-(N-(3-hydroxypropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

5) N-methyl-piperazinyl, N-ethyl-piperazinyl, N-isopropyl-piperazinyl, N-acetyl-piperazinyl, N-(2-hydroxyethyl) piperazinyl, N-(2-cyanoethyl) piperazinyl, N-(3-hydroxypropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;

6) morpholinyl, 3,5-dimethyl morpholinyl, thiomorpholinyl, tetrahydropyrrolyl, 3-N, N-dimethyl-tetrahydropyrrolyl, 3-N, N-diethyl tetrahydropyrrolyl.

In some preferred embodiments, $R_{14}$ is selected from:
1) methyl, ethyl, isopropyl, trifluoromethyl;
2) amino, cyclopropylamino, N, N-dimethylamino, N, N-diethylamino, N, N-diisopropylamino;
3) hydroxy;
4) piperidinyl, 4-N, N-dimethylamino-piperidinyl, 4-hydroxypiperidinyl, 4-(N-methylpiperazinyl) piperidinyl, 4-(tetrahydro-pyrrolyl) piperidinyl, 4-(3-N, N-dimethyl-tetrahydropyrrolyl) piperidinyl;
5) N-methyl-piperazinyl, N-ethyl-piperazinyl, N-isopropyl-piperazinyl, N-acetyl-piperazinyl, N-(2-hydroxyethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;
6) morpholinyl, 3,5-dimethyl morpholinyl, thiomorpholinyl, tetrahydropyrrolyl, 3-N, N-dimethyl-tetrahydropyrrolyl, 3-N, N-diethyl tetrahydropyrrolyl.

In some embodiments, $R_{24}$ is selected from: hydrogen, halo, nitro, amino, cyano, C1-C6 alkyl, said C1-C6 alkyl optionally substituted by halogen, nitro, amino, cyano; —O—C1-C6 alkyl, optionally substituted by halogen, nitro, amino, cyano.

In some preferred embodiments, $R_{24}$ is selected from: hydrogen, halogen, cyano, C1-C6 alkyl, said C1-C6 alkyl optionally substituted by halogen, nitro, amino, cyano.

In some embodiments, $R_{34}$ is selected from: hydrogen; C1-C6 alkyl; C3-C7 cycloalkyl.

In some preferred embodiments, $R_{34}$ is selected from: hydrogen, methyl, ethyl, isopropyl, cyclopropyl or cyclopentyl.

In some embodiments, $R_{44}$ is selected from: hydrogen; C1-C6 alkyl; C3-C7 cycloalkyl.

In some preferred embodiments, $R_{44}$ is selected from: hydrogen, methyl, ethyl, isopropyl, cyclopropyl or cyclopentyl.

In some embodiments, n4 selected from 0, 1, 2, 3

In some preferred embodiments, n4 selected from 0, 1, 2.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A sixth aspect, the present invention provides a compound represented by the following structural formula:

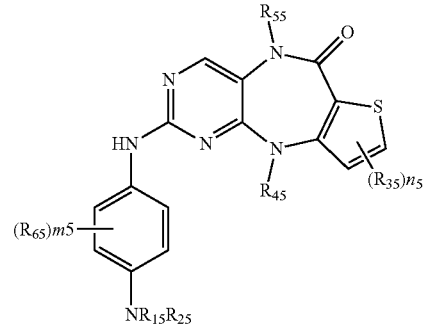

II-2 m5 is selected from 0, 1, 2, 3 or 4;
n5 is selected from 0, 1 or 2;
$R_{15}$, $R_{25}$ are independently selected from:
1) hydrogen; C1-C6 alkyl, optionally substituted by halogen, nitro, amino, cyano; C3-C7 cycloalkyl, which is optionally substituted by halogen, nitro, amino, cyano; a C1-C6 oxygen-containing alkyl;
2) —SO$_2$C1-C6 alkyl, optionally substituted by halogen, nitro, amino, cyano; —SO$_2$C2-C6 alkenyl, which is optionally substituted with halogen, nitro, amino, cyano substituted; —COC1-C6 alkyl, optionally substituted by halogen, nitro, amino, cyano; —COC2-C6 alkenyl, which is optionally substituted by halogen, nitro, amino, cyano;
Or, together with $R_{15}$ and $R_{25}$ and the N atom to which they are attached forming a hexaheterocyclic ring that contains one or more heteroatoms selected from N, O and S, said hexahetrerocyclic ring is optionally substituted with C1-C6 alkyl, hydroxyl, or amino group;
$R_{35}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, nbutoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{45}$ is selected from:

hydrogen; C1-C6 alkyl, optionally substituted by halogen, nitro, amino, cyano; C3-C7 cycloalkyl, which is optionally substituted by halogen, nitro, amino, cyano;

$R_{55}$ is selected from:

hydrogen; C1-C6 alkyl, optionally substituted by halogen, nitro, amino, cyano; C3-C7 cycloalkyl, which is optionally substituted by halogen, nitro, amino, cyano;

$R_{65}$ is selected from:

1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methaylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl foramido, cyclopentyl foramido, methylsulfonamido, ethylsulfonamido, propylsulfonamido, isopropylsulfonamido, dimethyl phosphinyl, diethyl phosphinyl, diisopropyl phosphinyl;

Or a stereoisomer of the above compounds, a prodrug thereof, a pharmaceutically acceptable salt thereof, or a pharmaceutically acceptable solvate thereof.

In some embodiments, $R_{15}$ is selected from: hydrogen; C1-C6 alkyl, optionally substituted by halogen, nitro, amino, cyano; —SO$_2$C1-C6 alkyl, optionally substituted with halogen, nitro, amino, cyano; —SO$_2$C2-C6 alkenyl, which is optionally substituted by halogen, nitro, amino, cyano; —COC1-C6 alkyl, optionally substituted with halogen, nitro group, an amino group, a cyano-substituted; —COC2-C6 alkenyl, which is optionally substituted by halogen, nitro, amino, cyano.

In some embodiments, $R_{25}$ is selected from: hydrogen; C1-C6 alkyl, optionally substituted by halogen, nitro, amino, cyano.

In some preferred embodiments, $R_{25}$ is hydrogen.

In some embodiments, $R_{15}$ and $R_{25}$ together with the N atom to which they are attached form a hexaheterocyclic ring contain one or more heteroatoms selected from N, O and S, the hexaheterocyclic ring is optionally substituted with C1-C6 alkyl, hydroxy, amino.

In some preferred embodiments, $R_{15}$ and $R_{25}$ together with the N atom to which they are attached form a piperidine ring, a piperazine ring, a piperidine ring, or a piperazine ring, which is optionally substituted with a C1-C6 alkyl, or hydroxyl.

In some embodiments, the, $R_{35}$ is selected from: hydrogen, halo, nitro, amino, cyano, C1-C6 alkyl, optionally substituted by halogen, nitro, amino, cyano; C3-C7 cycloalkyl alkyl optionally substituted by halogen, nitro, amino, cyano.

In some preferred embodiments, $R_{35}$ is selected from: hydrogen, halo, nitro, amino, cyano, C1-C6 alkyl.

In some embodiments, $R_{45}$ is selected from: hydrogen; C1-C6 alkyl; C3-C7 cycloalkyl.

In some preferred embodiments, $R_{45}$ is selected from: hydrogen, methyl, ethyl, isopropyl, cyclopropyl or cyclopentyl.

In some embodiments, $R_{55}$ is selected from: hydrogen; C1-C6 alkyl; C3-C7 cycloalkyl.

In some preferred embodiments, $R_{55}$ is selected from: hydrogen, methyl, ethyl, isopropyl, cyclopropyl or cyclopentyl.

In some embodiments, $R_{65}$ is selected from: hydrogen, halo, nitro, amino, cyano, C1-C6 alkyl, optionally substituted by halogen, nitro, amino, cyano; C3-C7 cycloalkyl, which is optionally substituted by halogen, nitro, amino, cyano.

In some preferred embodiments, $R_{65}$ is selected from: hydrogen, halo, nitro, amino, cyano, C1-C6 alkyl.

In some embodiments, m5 selected from 0, 1, 2, 3.

In some preferred embodiments, m5 selected from 0, 1, 2.

In some embodiments, n5 is selected from 0, 1.

In some preferred embodiments, n5 is zero.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A seventh aspect, the present invention provides a compound represented by the following structural formula:

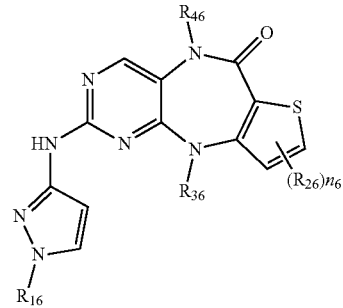

II-3 n6 is selected from 0, 1 or 2;

$R_{16}$ is selected from:

1) hydrogen; C1-C6 alkyl, optionally substituted by halogen, nitro, amino, cyano; C3-C7 cycloalkyl, which is optionally substituted by halogen, nitro, amino, cyano; a C1-C6 oxygen-containing alkyl;

2) —SO$_2$C1-C6 alkyl, optionally substituted by halogen, nitro, amino, cyano; —SO$_2$C2-C6 alkenyl, which is optionally substituted with halogen, nitro, amino, cyano substituted; —COC1-C6 alkyl, optionally substituted by halogen, nitro, amino, cyano; —COC2-C6 alkenyl, which is optionally substituted by halogen, nitro, amino, cyano;

3) piperidinyl, 4-N, N-dimethylamino-piperidinyl, 4-N, N-diethylamino-piperidinyl, 4-N, N-diisopropylamino-piperidinyl, 4-hydroxyl piperidinyl, 4-(N-methylpiperazinyl) piperidinyl, 4-(N-ethyl-piperazinyl) piperidinyl, 4-(N-isopropyl-piperazinyl) piperidine, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

$R_{26}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylesulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{36}$ is selected from: hydrogen; C1-C6 alkyl, optionally substituted by halogen, nitro, amino, cyano; C3-C7 cycloalkyl, which is optionally substituted with halogen, nitro, amino, cyano;

$R_{46}$ is selected from: hydrogen; C1-C6 alkyl, optionally substituted by halogen, nitro, amino, cyano; C3-C7 cycloalkyl, which is optionally substituted with halogen, nitro, amino, cyano;

Or a stereoisomer of the above compounds, a prodrug thereof, a pharmaceutically acceptable salt thereof, or a pharmaceutically acceptable solvate thereof.

In some embodiments, $R_{16}$ is selected from: hydrogen; C1-C6 alkyl; C3-C7 cycloalkyl; —SO₂C1-C6 alkyl; —SO₂C2-C6 alkenyl group; —COC1-C6 alkyl, which is optionally substituted by halogen, nitro, amino, cyano; —COC2-C6 alkenyl, which is optionally substituted by halogen, nitro, amino, cyano.

In some embodiments, $R_{26}$ is selected from hydrogen; hydrogen; methyl, ethyl, isopropyl, cyclopropyl; methylsulfonyl, ethylsulfonyl, isopropylsulfonyl, vinylsulfonyl; acetyl, chloroacetyl, bromoacetyl, acryloyl, 4-N, N-dimethylamino-2-butenoyl, 4-tetrahydro-pyrrolyl-2-butenoyl.

In some embodiments, $R_{26}$ is selected from: hydrogen, halo, nitro, amino, cyano, C1-C6 alkyl, optionally substituted by halogen, nitro, amino, cyano; C3-C7 cycloalkyl, which is optionally substituted by halogen, nitro, amino, cyano.

In some preferred embodiments, $R_{26}$ is selected from: hydrogen, halo, nitro, amino, cyano, C1-C6 alkyl.

In some embodiments, $R_{36}$ is selected from: hydrogen; C1-C6 alkyl; C3-C7 cycloalkyl.

In some embodiments, $R_{46}$ is selected from: hydrogen; C1-C6 alkyl; C3-C7 cycloalkyl.

In some embodiments, n6 is selected from 0, 1.

In some preferred embodiments, n6 is 0.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

An eighth aspect, the present invention provides a compound represented by the following structural formula:

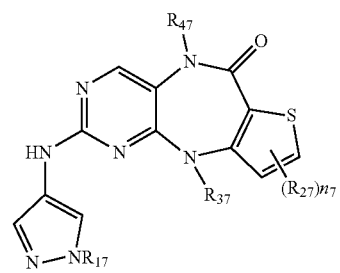

II-4 n7 is selected from 0, 1 or 2;

$R_{17}$ is selected from:

1) hydrogen; C1-C6 alkyl, optionally substituted by halogen, nitro, amino, cyano; C3-C7 cycloalkyl, which is optionally substituted by halogen, nitro, amino, cyano; a C1-C6 oxygen-containing alkyl;

2) —SO₂C1-C6 alkyl, optionally substituted by halogen, nitro, amino, cyano; —SO₂C2-C6 alkenyl, which is optionally substituted with halogen, nitro, amino, cyano substituted; —COC1-C6 alkyl, optionally substituted by halogen, nitro, amino, cyano; —COC2-C6 alkenyl, which is optionally substituted by halogen, nitro, amino, cyano;

3) piperidinyl, 4-N, N-dimethylamino-piperidinyl, 4-N, N-diethylamino-piperidinyl, 4-N, N-diisopropylamino-piperidinyl, 4-hydroxyl piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

$R_{27}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;
$R_{37}$ is selected from:
Hydrogen; C1-C6 alkyl, optionally substituted by halogen, nitro, amino, cyano; C3-C7 cycloalkyl, which is optionally substituted by halogen, nitro, amino, cyano;
$R_{47}$ is selected from:
Hydrogen; C1-C6 alkyl, optionally substituted by halogen, nitro, amino, cyano; C3-C7 cycloalkyl, which is optionally substituted by halogen, nitro, amino, cyano;
Or a stereoisomer of the above compounds, a prodrug thereof, a pharmaceutically acceptable salt thereof, or a pharmaceutically acceptable solvate thereof.

In some embodiments, $R_{17}$ is selected from hydrogen; hydrogen; C1-C6 alkyl; C3-C7 cycloalkyl; —SO$_2$C1-C6 alkyl; —SO$_2$C2-C6 alkenyl; —COC1-C6 alkyl, which is optionally substituted by halogen, nitro, amino, cyano; —COC2-C6 alkenyl, which is optionally substituted by halogen, nitro, amino, cyano.

In some preferred embodiments, $R_{14}$ is selected from hydrogen; hydrogen; methyl, ethyl, isopropyl, cyclopropyl; methylsulfonyl, ethylsulfonyl, isopropylsulfonyl, vinylsulfonyl; acetyl, chloroacetyl, bromoacetyl, acryloyl, 4-N, N-dimethylamino-2-butenoyl, 4-tetrahydro-pyrrolidin-2-butenoyl.

In some embodiments, $R_{27}$ is selected from: hydrogen, halo, nitro, amino, cyano, C1-C6 alkyl, optionally substituted by halogen, nitro, amino, cyano; C3-C7 cycloalkyl, which is optionally substituted by halogen, nitro, amino, cyano.

In some preferred embodiments, $R_{27}$ is selected from: hydrogen, halo, nitro, amino, cyano, C1-C6 alkyl.

In some embodiments, $R_{37}$ is selected from: hydrogen; C1-C6 alkyl; C3-C7 cycloalkyl.

In some embodiments, $R_{47}$ is selected from: hydrogen; C1-C6 alkyl; C3-C7 cycloalkyl.

In some embodiments, n7 is selected from 0, 1.

In some preferred embodiments, n7 is zero.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A ninth aspect, the present invention provides a compound represented by the following structural formula:

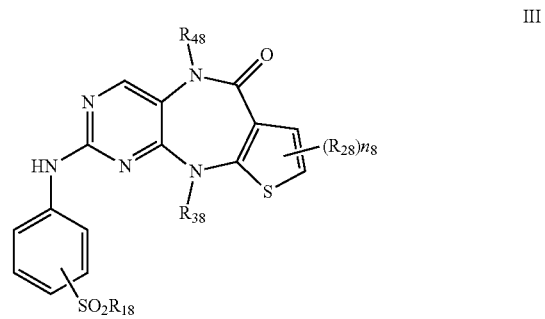

III n8 is selected from 0, 1 or 2;
$R_{18}$ is selected from:
1) selected from the group of five-membered heterocyclic or six-membered heterocyclic rings comprising one or more heteroatoms selected from N, O and S, the five-membered heterocyclic or six-membered heterocyclic rings are optionally substituted with C1-C6 alkyl, C1-C6 alkoxy, hydroxy, amino, C1-C6 acyl, a cyano, a substituted heterocyclic group,
including but not limited to: 4-N, N-dimethylamino-piperidinyl, 4-N, N-diethylamino-piperidinyl, 4-N, N-diisopropylamino-piperidinyl, 4-hydroxyl-piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxyethyl) piperazinyl) piperidinyl, 4-(N-(2-cyanoethyl) piperazinyl) piperidinyl, 4-(N-(3-hydroxyl propyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;
2) amino, cyclopropylamino, cyclobutylamino, cyclopentylamino, cyclohexylamino, N, N-dimethylamino, N, N-diethylamino, N, N-diisopropylamino, 2-N, N-dimethylethylamino, 2-hydroxyethylamino, 2-morpholinyl-ethylamino, 2-(4-N-methylpiperazinyl) ethylamino, 3-N, N-dimethylaminopropyl amino, 3-N, N-diethylamino propylamino, 3-N, N-diisopropylpropylamino, 3-hydroxypropyl amino, 3-morpholinyl-propylamino, 3-(4-N-methylpiperazinyl) propylamino, N-methylpiperidiny-4-amino, N-ethylpiperidinyl-4-amino, N-isopropyl piperidinyl-4-amino, N-acetylpiperidinyl-4-amino; N-methyl-piperazinyl, N-ethyl-piperazinyl, N-isopropyl-piperazinyl, N-acetyl piperazinyl, N-tert-butoxyl formyl-piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl aminoethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl;

3) C1-C6 alkyl, optionally substituted by halogen, nitro, cyano;
4) C3-C7 cycloalkyl, which is optionally substituted by halogen, nitro, cyano;
5) —O—C1-C6 alkyl, optionally substituted by halogen, nitro, amino, cyano;
6) —O—C3-C7 cycloalkyl, which is optionally substituted by halogen, nitro, amino, cyano;
7) C6-C10 aryl, which is optionally substituted by halogen, nitro, amino, cyano; —O—C6-C10 aryl, which is optionally substituted by halogen, nitro, amino, cyano;
8) C2-C6 alkenyl;
9) hydroxyl, 2-N, N-dimethylaminoethoxyl, 2-N, N-diethylaminoethoxyl, 2-N, N-diisopropyl-aminoethoxyl, 2-(N-methylpiperazine-yl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monohalogen-substituted phenylmethoxyl, homodihalogen-substituted phenylmethoxyl, heterodihalogen-substituted phenylmethoxyl;

$R_{28}$ is selected from:
1) a hydrogen, halo, nitro, amino, cyano;
2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;
3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{38}$ is selected from: hydrogen; C1-C6 alkyl, optionally substituted by halogen, nitro, amino, cyano; C3-C7 cycloalkyl, which is optionally substituted with halogen, nitro, amino, cyano;

$R_{48}$ is selected from: hydrogen; C1-C6 alkyl, optionally substituted by halogen, nitro, amino, cyano; C3-C7 cycloalkyl, which is optionally substituted with halogen, nitro, amino, cyano;

Or a stereoisomer of the above compounds, a prodrug thereof, a pharmaceutically acceptable salt thereof, or a pharmaceutically acceptable solvate thereof.

In some embodiments, $R_{18}$ is selected from:
1) C1-C6 alkyl, C3-C7 cycloalkyl;
2) amino, cyclopropylamino, cyclopentylamino, cyclohexylamino, N, N-dimethylamino, N, N-diethylamino, N, N-diisopropylamino, 2-N, N-dimethylamino, diethylamino, 2-hydroxylethylamino, 2-morpholinyl-ethylamino, 2-(4-N-piperazinyl-methyl) ethylamino, N-methylpiperidinyl-4-amino, N-ethylpiperidinyl-4-amino, N-isopropyl-piperidinyl-4-amino, N-acetyl-piperidinyl-4-amino;
3) hydroxyl, 2-N, N-dimethylaminoethoxyl, 2-N, N-diethyl-aminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl methoxyl, 3-pyridyl-methoxy, 4-pyridyl methoxyl;
4) piperidinyl, 4-N, N-dimethylamino-piperidinyl, 4-hydroxypiperidinyl, 4-(N-methylpiperazinyl) piperidinyl, 4-(N-ethyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxyethyl) piperazinyl) piperidinyl, 4-(N-(2-cyanoethyl) piperazinyl) piperidinyl, 4-(N-(3-hydroxypropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;
5) N-methyl-piperazinyl, N-ethyl-piperazinyl, N-isopropyl-piperazinyl, N-acetyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;
6) morpholinyl, 3,5-dimethyl morpholinyl, thiomorpholinyl, tetrahydropyrrolyl, 3-N, N-dimethyl-tetrahydropyrrolyl, 3-N, N-diethyl tetrahydropyrrolyl.

In some preferred embodiments, $R_{18}$ is selected from:
1) methyl, ethyl, isopropyl, trifluoromethyl;
2) amino, cyclopropylamino, N, N-dimethylamino, N, N-diethylamino, N, N-diisopropylamino;
3) hydroxy;
4) piperidinyl, 4-N, N-dimethylamino-piperidinyl, 4-hydroxypiperidinyl, 4-(N-methylpiperazinyl) piperidinyl, 4-(tetrahydro-pyrrolyl) piperidinyl, 4-(3-N, N-dimethyl-tetrahydropyrrolyl) piperidinyl;
5) N-methyl-piperazinyl, N-ethyl-piperazinyl, N-isopropyl-piperazinyl, N-acetyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl;
6) morpholinyl, 3,5-dimethyl morpholinyl, thiomorpholinyl, tetrahydropyrrolyl, 3-N, N-dimethyl-tetrahydropyrrolyl, 3-N, N-diethyl tetrahydropyrrolyl.

In some embodiments, $R_{28}$ is selected from: hydrogen, halo, nitro, amino, cyano, C1-C6 alkyl, optionally substituted by halogen, nitro, amino, cyano; C3-C7 cycloalkyl, which is optionally substituted by halogen, nitro, amino, cyano.

In some preferred embodiments, $R_{28}$ is selected from: hydrogen, halo, nitro, amino, cyano, C1-C6 alkyl.

In some embodiments, $R_{38}$ is selected from: hydrogen; C1-C6 alkyl; C3-C7 cycloalkyl.

In some embodiments, $R_{48}$ is selected from: hydrogen; C1-C6 alkyl; C3-C7 cycloalkyl.

In some embodiments, n8 is selected from 0, 1.

In some preferred embodiments, n8 is 0.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

A tenth aspect, the present invention provides a compound represented by the following structural formula:

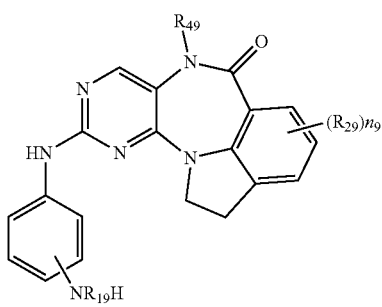

IV-1 n9 is selected from 0, 1, 2 or 3;

$R_{19}$ is selected from:

1) hydrogen; C1-C6 alkyl, optionally substituted by halogen, nitro, amino, cyano; C3-C7 cycloalkyl, which is optionally substituted by halogen, nitro, amino, cyano; a C1-C6 oxygen-containing alkyl;

2) —$SO_2$C1-C6 alkyl, optionally substituted by halogen, nitro, amino, cyano; —$SO_2$C2-C6 alkenyl, which is optionally substituted with halogen, nitro, amino, cyano substituted; —COC1-C6 alkyl, optionally substituted by halogen, nitro, amino, cyano; —COC2-C6 alkenyl, which is optionally substituted by halogen, nitro, amino, cyano;

$R_{29}$ is selected from:

1) a hydrogen, halo, nitro, amino, cyano;

2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;

3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylaminoformyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{49}$ is selected from: hydrogen; C1-C6 alkyl, optionally substituted by halogen, nitro, amino, cyano; C3-C7 cycloalkyl, which is optionally substituted with halogen, nitro, amino, cyano;

Or a stereoisomer of the above compounds, a prodrug thereof, a pharmaceutically acceptable salt thereof, or a pharmaceutically acceptable solvate thereof.

In some embodiments, $R_{19}$ is selected from hydrogen; C1-C6 alkyl; C3-C7 cycloalkyl; —$SO_2$C1-C6 alkyl; —$SO_2$C2-C6 alkenyl group; —COC1-C6 alkyl, which is optionally substituted by halogen, nitro, amino, cyano; —COC2-C6 alkenyl, which is optionally substituted by halogen, nitro, amino, cyano.

In some preferred embodiments, $R_{19}$ is selected from methyl, ethyl, isopropyl, cyclopropyl; methylsulfonyl, ethylsulfonyl, isopropylsulfonyl, vinylsulfonyl; acetyl, chloroacetyl, bromoacetyl, acryloyl, 4-N, N-dimethylamino-2-butenoyl, 4-tetrahydro-pyrrolyl-2-butenoyl.

In some embodiments, $R_{29}$ is selected from: hydrogen, halo, nitro, amino, cyano, C1-C6 alkyl.

In some preferred embodiments, $R_{29}$ is selected from: hydrogen, fluorine, chlorine, bromine, nitro, amino, cyano, methyl.

In some embodiments, $R_{49}$ is selected from: hydrogen; C1-C6 alkyl; C3-C7 cycloalkyl.

In some embodiments, n9 is selected from 0, 1, 2.

In some preferred embodiments, n9 is selected from 0, 1.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

An eleventh aspect, the present invention provides a compound represented by the following structural formula:

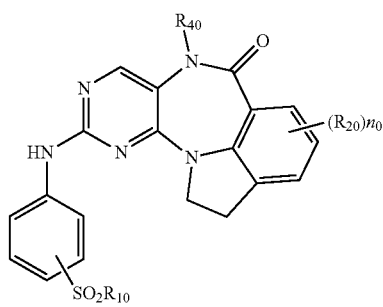

IV-2 n0 is selected from 0, 1, 2 or 3;

$R_{10}$ is selected from:

1) selected from the group of five-membered heterocyclic or six-membered heterocyclic rings comprising one or more heteroatoms selected from N, O and S, the five-membered heterocyclic or six-membered heterocyclic rings are optionally substituted with C1-C6 alkyl, C1-C6 alkoxy, hydroxy, amino, alkylamino, dialkylamino, C1-C6 acyl, cyano, optionally substituted C1-C6 alkyl, —O—C1-C6 alkyl, hydroxy, hydroxy C1-C6 alkyl, C1-C6 acyl, alkylamino, dialkylamino substituted heterocyclic group, including but not limited to: 4-N, N-dimethylamino-piperidinyl, 4-N, N-diethylamino-piperidinyl, 4-N, N-diisopropylamino-piperidinyl, 4-hydroxyl-piperidinyl, 4-(N-methylpiperazinyl) piperidinyl, 4-(N-ethyl-piperazinyl) piperidinyl, 4-(N-isopropyl-piperazinyl) piperidinyl, 4-(N- acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxyl propyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

2) amino, cyclopropylamino, cyclobutylamino, cyclopentylamino, cyclohexylamino, N, N-dimethylamino, N, N-diethylamino, N, N-diisopropylamino, 2-N, N-dimethylamino-ethyl, 2-hydroxylethylamino, 2-morpholinyl-ethylamino, 2-(4-N-methylpiperazinyl) ethylamino, 3-N, N-dimethyl-aminopropyl amino, 3-N, N-diethylaminopropyl amino, 3-N, N-diisopropylamino-propyl amino, 3-hydroxylpropyl amino, 3-morpholinyl-propylamino, 3-(4-N-methylpiperazinyl) propylamino, N-methyl-piperidinyl-4-amino, N-ethylpiperidinyl-4-amino, N-isopropyl piperidinyl-4-amino, N-acetylpiperidinyl-4-amino; N-methyl-piperazinyl, N-ethyl-piperazinyl, N-isopropyl-piperazinyl, N-acetyl piperazinyl, N-tert-butoxyl formyl-piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl aminoethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl;

3) C1-C6 alkyl, optionally substituted by halogen, nitro, cyano;

4) C3-C7 cycloalkyl, which is optionally substituted by halogen, nitro, cyano;

5) —O—C1-C6 alkyl, optionally substituted by halogen, nitro, amino, cyano;

6) —O—C3-C7 cycloalkyl, which is optionally substituted by halogen, nitro, amino, cyano;

7) C6-C10 aryl group, which is optionally substituted by halogen, nitro, amino, cyano; —O—C6-C10 aryl, which is optionally substituted by halogen, nitro, amino, cyano;

8) C2-C6 alkenyl group;

9) hydroxyl, 2-N, N-dimethylaminoethoxyl, 2-N, N-diethylaminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethylamino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl methoxyl, 3-pyridyl-methoxyl, 4-pyridyl methoxyl, phenyl-methoxyl, monohalogen-substituted phenylmethoxyl, homodihalogen-substituted phenyl methoxyl, heterodihalo-substituted phenylmethoxyl;

$R_{20}$ is selected from:

1) a hydrogen, halo, nitro, amino, cyano;

2) C1-C6 alkyl, optionally substituted by halogen, nitro, amino, cyano; —O—C1-C6 alkyl, optionally substituted by halogen, nitro, amino, cyano; a C1-C6 oxygen-containing alkyl;

3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino-sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{40}$ is selected from: hydrogen; C1-C6 alkyl, optionally substituted by halogen, nitro, amino, cyano; C3-C7 cycloalkyl, which is optionally substituted with halogen, nitro, amino, cyano;

Or a stereoisomer of the above compounds, a prodrug thereof, a pharmaceutically acceptable salt thereof, or a pharmaceutically acceptable solvate thereof.

In some embodiments, $R_{10}$ is selected from —SO$_2$C1-C6 alkyl, optionally substituted by halogen, nitro, amino, cyano; —SO$_2$NH$_2$.

In some preferred embodiments, $R_{10}$ is —SO$_2$NH$_2$.

In some embodiments, $R_{20}$ is selected from: hydrogen, halo, nitro, amino, cyano, C1-C6 alkyl.

In some preferred embodiments, $R_{20}$ is selected from: hydrogen, fluorine, chlorine, bromine, nitro, amino, cyano, methyl.

In some embodiments, $R_{40}$ is selected from: hydrogen; C1-C6 alkyl; C3-C7 cycloalkyl.

In some embodiments, n0 is selected from 0, 1, 2.

In some preferred embodiments, n0 is selected from 0, 1.

In some embodiments, the pharmaceutically acceptable salt is an inorganic or organic acid salts, wherein the inorganic salt is a hydrochloride, hydrobromide, hydroiodide, nitrate, bicarbonate, and salts of carbonates, sulfates or phosphates, the organic acid salt is a formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is methylsulfonate or ethylsulfonate; arylsulfonates as the benzylsulfonate or p-toluenylsulfonate.

Unless otherwise stated, the above groups and substituents have the ordinary meaning in the field of medicinal chemistry.

Incidentally, the oxygen-containing C1-C6 alkyl refers to the backbone of C1-C6 alkyl being substituted with one or more C1-C6 alkoxy group such as methoxyl ethyl, methoxyl ethoxyl methyl and the like.

The term "a C6-10 aryl" refers to mono-, di- or more carbocyclic hydrocarbon that has optionally further fused or linked to each other through a single bond to form 1-2 ring system, said carbocyclic ring comprises at least one "aromatic", wherein the term "aromatic" refers to an electronic key system π-completely conjugated. Aryl ring may be optionally further fused or linked to the carbocyclic and heterocyclic aromatic and non-aromatic rings. Non-limiting examples of the aryl group are phenyl, α- or β-naphthyl.

The term "heteroaryl" refers to an aromatic heterocycle, typically a 5- to 8-membered heterocyclic ring having from 1 to 3 heteroatoms selected from N, O or S; heteroaryl ring may optionally be further fused or linked to the carbocyclic and heterocyclic aromatic and non-aromatic. Non-limiting examples of the heteroaryl group, for example, pyridyl, pyrazinyl, pyrimidinyl, pyridazinyl, indolyl, imidazolyl, thiazolyl, isothiazolyl, thiazolyl, oxazolyl, pyrrolyl, phenyl group-pyrrolyl, furanyl, phenyl-furanyl, oxazolyl, isoxazolyl, pyrazolyl, thienyl, benzothienyl, iso indolinyl, benzimidazolyl, indazolyl, quinolinyl, isoquinolinyl, 1,2,3-triazolyl, 1-phenyl-1,2,3-triazole, 2,3-dihydro-indolyl, 2,3-hydrogen benzofuranyl, 2,3-dihydro-benzothienyl, benzopyranyl, 2,3-dihydro-benzoxazin-yl, 2,3-dihydro-quinoxalinyl and the like.

The term "heterocyclyl" (also referred to as "heterocycloalkyl") refers to a 3-, 4-, 5-, 6- and 7-membered saturated or partially unsaturated carbocyclic ring, wherein one or more carbon atoms are replaced by the heteroatoms such as nitrogen, oxygen and sulfur. Non-limiting examples of heterocyclyl groups are, for example pyran, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine, morpholine group, a pyrrolidine group, thiomorpholinyl group and the like.

The term "$C_1$-$C_6$ alkyl" refers to any straight or branched chain groups containing 1 to 6 carbon atoms, e.g., methyl, ethyl, n-propyl, isopropyl, n-butyl, isobutyl, tert-butyl, sec-butyl, n-pentyl, tert-pentyl, n-hexyl and the like.

Unless otherwise provided, the term "$C_3$-$C_7$ cycloalkyl" refers to a 3- to 7-membered whole-carbon monocyclic ring, which may contain one or more double bonds, but does not have a completely conjugated π-electronic system. Examples of cycloalkyl groups are, but are not limited to, cyclopropane, cyclobutane, cyclopentane, cyclopentene, cyclohexane, cyclohexene, cyclohexadiene, cycloheptane, cycloheptene, cycloheptadiene.

The term "$C_2$-$C_6$ alkenyl" refers to any group with 2 to 6 carbon atoms and containing a straight chain or branched chain and at least one alkenyl group such as vinyl, allyl, 1-propenyl group, isopropenyl, 1-butenyl, 2-butenyl, 3-butenyl, 2-pentenyl, 1-hexenyl and the like.

The term "C2-C6 alkynyl group" refers group with 2 to 6 carbon atoms and containing a straight chain or branched chain and at least one alkynyl group, for example ethynyl, 2-propynyl, 4-alkynyl group and the like.

The term "$C_1$-$C_6$ acyl" refers to a —C(=O)—H and —C(=O)—C1-C5 alkyl groups, such as formyl, acetyl, propionyl, butyryl and the like.

Wherein the term "$C_1$-$C_5$ alkyl" refers to any straight or branched chain group containing 1-5 carbon atoms, e.g., methyl, ethyl, n-propyl, isopropyl, n-butyl, isobutyl, tert-butyl, sec-butyl, n-pentyl, tert-pentyl and the like.

According to the present invention and unless otherwise provided, any of the above groups may be optionally substituted at any of its free positions with one or more substituent groups, for example substituted by 1-6 groups, independently selected from the group: a halogen atom, nitro, oxo (=O), cyano, $C_1$-$C_6$ alkyl, polyfluorinated alkyl, polyfluorinated alkoxy, alkenyl, alkynyl, hydroxyalkyl, hydroxyalkyl an amino group, a hydroxyl heterocyclic group, an aryl group, aryl-alkyl, heteroaryl, heteroaryl-alkyl, heterocyclyl, heterocyclyl-alkyl, $C_3$-$C_7$ cycloalkyl, cycloalkyl-alkyl, alkyl-aryl, alkyl-heteroaryl, alkyl-heterocyclyl, alkyl-cycloalkyl, alkyl-aryl-alkyl, alkyl-heteroaryl-alkyl, alkyl-heterocyclyl-alkyl, alkyl-cycloalkyl-alkyl, alkyl-heterocyclyl-heterocyclyl, heterocyclyl-heterocyclyl, heterocyclyl-alkyl-heterocyclyl, heterocyclyl-alkylamino, alkyl-heterocyclyl-alkyl-amino, hydroxyl, alkoxyl, aryloxyl, heterocyclic oxyl group, alkyl-heterocyclyloxyl, methylenedioxyl, alkylcarbonyloxyl, arylcarbonyloxyl, cycloalkenyloxyl, heterocyclic carbonyloxyl, alkylene alkylamino oxyl, carboxyl, alkoxycarbonyl, aryloxycarbonyl, cycloalkyl, carbonyl, heterocyclic oxycarbonyl, amino, ureido, alkylamino, amino-alkylamino, di-alkylamino, dialkylamino-heterocyclyl, di-alkylamino-alkylamino, arylamino, arylalkyl, diarylamino, heterocyclic, alkyl-heterocyclyl amino, alkyl-heterocyclylcarbonyl, formylamino, alkylcarbonylamino, arylcarbonyl, heterocyclic carbonyl, alkyl-eterocyclyl carbonyl amino, aminocarbonyl, alkylaminocarbonyl, dialkylaminocarbonyl, aryl aminocarbonyl, heteroaryl cyclic aminocarbonyl, alkoxycarbonyl, alkoxycarbonyl-alkylamino, alkoxycarbonyl heterocyclyl-alkylamino, alkoxy-aryl-alkyl, hydroxy amino-carbonyl, alkoxy imino, alkylsulfonylamino, arylsulfonylamino, heterocyclic sulfonylamino, formyl, alkylcarbonyl, arylcarbonyl, cycloalkylcarbonyl, heterocyclylcarbonyl, alkylsulfonyl, aryl sulfonyl, aminosulfonyl, alkylaminosulfonyl, dialkylaminosulfonyl, aminosulfonyl, heterocyclic aminosulfonyl, arylthio, alkylthio, phosphonate and alkylphosphonate.

Furthermore, if appropriate, each of the above substituents may be further substituted by one or more of the above mentioned groups.

In this regard, the term "halogen atom" refers to fluorine, chlorine, bromine or iodine atom.

The term "cyano" means a-CN residue.

The term "nitro" means a-$NO_2$ group.

The term "alkoxy", "cycloalkyl group", "aryl group", "heterocyclic group" and its derivatives refer to any of the above $C_1$-$C_6$ alkyl, $C_3$-$C_7$ a cycloalkyl group, an aryl group or a heterocyclic group, which is connected to the rest of the molecule through an oxygen atom (—O—).

From all of the above description, it will be apparent to the skilled person that the name is any group of composite such as "aryl group", which is referred to the moiety conventionally derived therefrom such as substituted from an aryl group, wherein aryl is as defined above.

Likewise, any terms such as alkylthio, alkylamino, dialkylamino, alkoxycarbonyl group, an alkoxycarbonyl group, a heterocyclic carbonyl group, a heterocyclic carbonyl group, oxycarbonyl group and the like cycloalkyl groups include, wherein the alkyl, alkoxy, aryl, $C_3$-$C_7$ cycloalkyl and heterocyclyl portions are as defined above.

As used herein, unless otherwise indicated, the term "prodrug" refers to a derivative can be hydrolyzed, oxidized, or otherwise reacted under biological conditions (in vitro or in vivo) to provide the compound of the present invention. Only after the reaction under biological conditions the prodrug becomes active compounds, or they are active in the form of their non-reaction. well-known methods may generally be used to prepare prodrugs, e.g. the methods described in Burger's Medicinal Chemistry and Drug Discovery (1995) 172-178, 949-982 (Manfred E. Wolff ed., 5th ed).

As used herein, examples of the term "pharmaceutically acceptable salts of the compounds Formula (I)" are organic acid salts formed by forming a pharmaceutically acceptable organic acid anions, including but not limited to formate, acetate, propionate, benzoate, maleate, fumarate, succinate, tartrate, citrate, ascorbate, alpha-ketoglutarate, alpha-glycerophosphate, alkyl sulfonate or aryl sulfonate; preferably, the alkyl sulfonate is a methylsulfonate or ethylsulfonate; arylsulfonates as the benzylsulfonate or p-toluene sulfonate. Suitable inorganic salts may also be formed, including but not limited to, hydrochloride, hydrobromide, hydroiodide, nitrate, bicarbonate and carbonate, sulfate or phosphate and the like.

Pharmaceutically acceptable salts using standard procedures known in the art to obtain, for example, by adding a sufficient amount of the basic compound and to provide a pharmaceutically acceptable anion of a suitable acid.

As used herein, the term "treating" generally refers to obtaining desired pharmacological and/or physiological effect. The effect of the completely or partially preventing a disease or symptom thereof, may be prophylactic; and/or partial or complete stabilization or cure for a disease and/or disease produced side effects, may be therapeutic. As used herein, "treatment" encompasses any treatment of a disease in a patient, comprising: (a) preventing the disease or condition susceptible but not yet diagnosed the disease or symptoms of the disease occurred; (b) inhibiting the disease symptom, ie, arresting its development; or (c) to alleviate symptoms of the disease, that is, causing the symptoms of the disease or degeneration.

According to one particular aspect of the present invention, a compound, a stereoisomer, a prodrug, or a pharmaceutically acceptable salt or a pharmaceutically acceptable solvate thereof, wherein the compound is the following Examples in one of the compounds.

Another aspect, the present invention provides a pharmaceutical composition comprising a compound according to any preceding aspect, a stereoisomer, a prodrug, or a pharmaceutically acceptable salt or a pharmaceutically acceptable solvate thereof, and a pharmaceutically acceptable carrier, diluent or excipient.

The method of preparing pharmaceutical compositions having a certain amount of the various active ingredients is known, or apparent to the skilled person in accordance with the present disclosure. For example, Remington's Pharmaceutical Sciences, Martin, E W, ed., Mack Publishing Company, 19th ed. (1995), the method of preparing the pharmaceutical composition comprising addition of a suitable pharmaceutical excipient incorporated, carriers, diluents and the like.

The known method of manufacturing pharmaceutical formulations of the present invention includes conventional mixing, dissolving or lyophilizing processes. Compounds of the invention may be formulated into pharmaceutical compositions, and patients with various routes of administration suitable for the selected mode of administration, e.g., oral or parenteral (by intravenous, intramuscular, topical or subcutaneous routes).

Accordingly, the compounds of the present invention bounded with acceptable carrier (such as an inert diluent or an assimilable edible carrier) may be pharmaceutically administered to any part of the body, e.g., orally. They may be enclosed in hard or soft shell gelatin capsules, may be pressed into tablets. For oral therapeutic administration, the active compound may be combined with one or more excipients and used in swallowable tablet, buccal tablet, troches, capsules, elixirs, suspensions, syrups, wafers, and the like use. Such compositions and preparations should contain at least 0.1% of active compound. Proportion of such compositions and preparations can, of course, change, may comprise from about 1% by weight of a given unit dosage form to about 99%. In such therapeutically useful compositions, such that the amount of active compound an effective dosage level will be obtained.

Tablets, troches, pills, capsules and the like may also contain: a binder such as gum tragacanth, acacia, corn starch or gelatin; excipients, such as dicalcium phosphate; a disintegrating agent such as corn starch, potato starch, alginic acid and the like; lubricants, such as magnesium stearate; and a sweetening agent such as sucrose, fructose, lactose or aspartame; or a flavoring agent such as peppermint, oil of wintergreen, or cherry flavoring. When the dosage unit form is a capsule, in addition to materials of the above type, it may contain a liquid carrier, such as a vegetable oil or polyethylene glycol. Various other materials may be present as coatings or modify the physical form of the solid unit dosage form in other ways. For instance, tablets, pills, or capsules may be coated with gelatin, wax, shellac or sugar-coated. A syrup or elixir may contain the active compound, sucrose or fructose as a sweetening agent, methyl paraben or propyl paraben as preservatives, a dye and a flavoring (flavor such as cherry or orange flavor). Of course, any material used in preparing any unit dosage form should be pharmaceutically acceptable and substantially non-toxic in the volume application. In addition, the active compound may be incorporated into sustained-release preparations and sustained release devices.

The active compounds can also be administered intravenously or intraperitoneally by infusion or by injection. It may be prepared in an aqueous solution of the active compound or a salt thereof, optionally mixed nontoxic surfactant. It can also be prepared in glycerol, liquid polyethylene glycols, triacetin oils, and mixtures thereof and a dispersing agent. Under ordinary conditions of storage and use, these preparations contain a preservative to prevent the growth of microorganisms.

Suitable for injection or infusion dosage forms may comprise a pharmaceutical active ingredient comprising a solution or dispersion suitable for sterile injectable or infusible formulation of the instant (optionally encapsulated in liposomes) in sterile aqueous solutions or dispersions or sterile powders. In all cases, the ultimate dosage form under the conditions of manufacture and storage must be sterile, liquid, and stable. The liquid carrier can be a solvent or liquid dispersion medium comprising, for example, vegetable oils, nontoxic glyceryl esters, and suitable mixtures thereof, water, ethanol, polyol (e.g., glycerol, propylene glycol, liquid polyethylene glycol, etc.). Proper fluidity can be maintained, for example, by the formation of liposomes, by the maintenance of the required particle size in the case of dispersions, or by using surfactants. It may be (e.g., parabens, chlorobutanol, phenol, sorbic acid, thimerosal, and the like) prevention of the action of microorganisms by various antibacterial and antifungal agents. In many cases, it is preferable to include isotonic agents, such as sugars, buffers or sodium chloride. By using the compositions of agents delaying absorption (for example, aluminum monostearate and gelatin) may produce prolonged absorption of the injectable compositions.

The above various binding the active compound with a suitable solvent required in the required amount of other ingredients enumerated, and then sterilized by filtration, the preparation of sterile injectable solutions. In the case of sterile powders for the preparation of sterile injectable solutions, the preferred methods of preparation are vacuum drying and freeze-drying techniques, which produces a powder of the active ingredient plus any additional desired previously sterile-filtered solution in the presence of a component.

Useful solid carriers include finely divided solid (such as talc, clay, microcrystalline cellulose, silica, alumina, etc.). Useful liquid carriers include water, ethanol or ethylene glycol or water-ethanol/glycol mixture, compounds of the invention can optionally with the aid of a surfactant effective content nontoxic dissolved or dispersed therein. Adjuvants may be added (e.g., flavoring) and additional antimicrobial agents to optimize the properties for a given use.

Thickening agents (such as synthetic polymers, fatty acids, fatty acid salts and esters, fatty alcohols, modified celluloses or modified mineral materials) and liquid carriers may also be used to form spreadable pastes, gels, ointments and soap, was used directly on the skin of the user.

The therapeutically required amount of compound or a therapeutically active salt or derivative thereof depends not only on the particular salt selected but also on the mode of administration, the age and the nature and state of the disease to be treated, ultimately depends on the attendant physician or clinician decision.

Above formulations may be presented in unit dosage form, which unit dosage form is a physically discrete unit containing a unit dose, suitable for administration to humans and other mammalian body. The unit dosage form can be a capsule or tablet, or a lot of capsules or tablets. According to the particular treatment involved, the amount of active ingredient in a unit dose may be varied or adjusted from between about 0.1 to about 1000 milligrams or more.

Also included are various applications of new dosage forms such as liposomes, microspheres and nanospheres, such as using fine particle dispersion comprising polymeric micelles (polymeric micelles), nanoemulsion (nanoemulsion), submicron emulsion (submicroemuls micro capsule (microcapsule), microspheres (microsphere), liposomes (liposomes) and lipid vesicles (niosomes) (also known as non-ionic surfactant vesicles) in the manufacture of a medicament and the like.

Another aspect, the present invention also provides a method for preparing the compound of any preceding aspect, comprising the steps of:

In the following synthesis method, symbol Z in the formula $R_{41}Z$ or $R_{31}Z$ represents a leaving group, such as halogen, mesylate, triflate.

Reaction conditions: (a) basic conditions (such as diisopropylethylamine, triethylamine, potassium carbonate, etc.) or acidic conditions (trifluoroacetic acid, hydrochloric acid, etc.) substitution reaction; (b) reducing the nitro group and the amide cyclization (e.g., iron/acetic acid, etc.); (c) a basic condition (e.g., sodium hydroxide, etc.); (d) acidic conditions (trifluoroacetic acid, hydrochloric acid, etc.) or palladium-catalyzed amination reaction; or

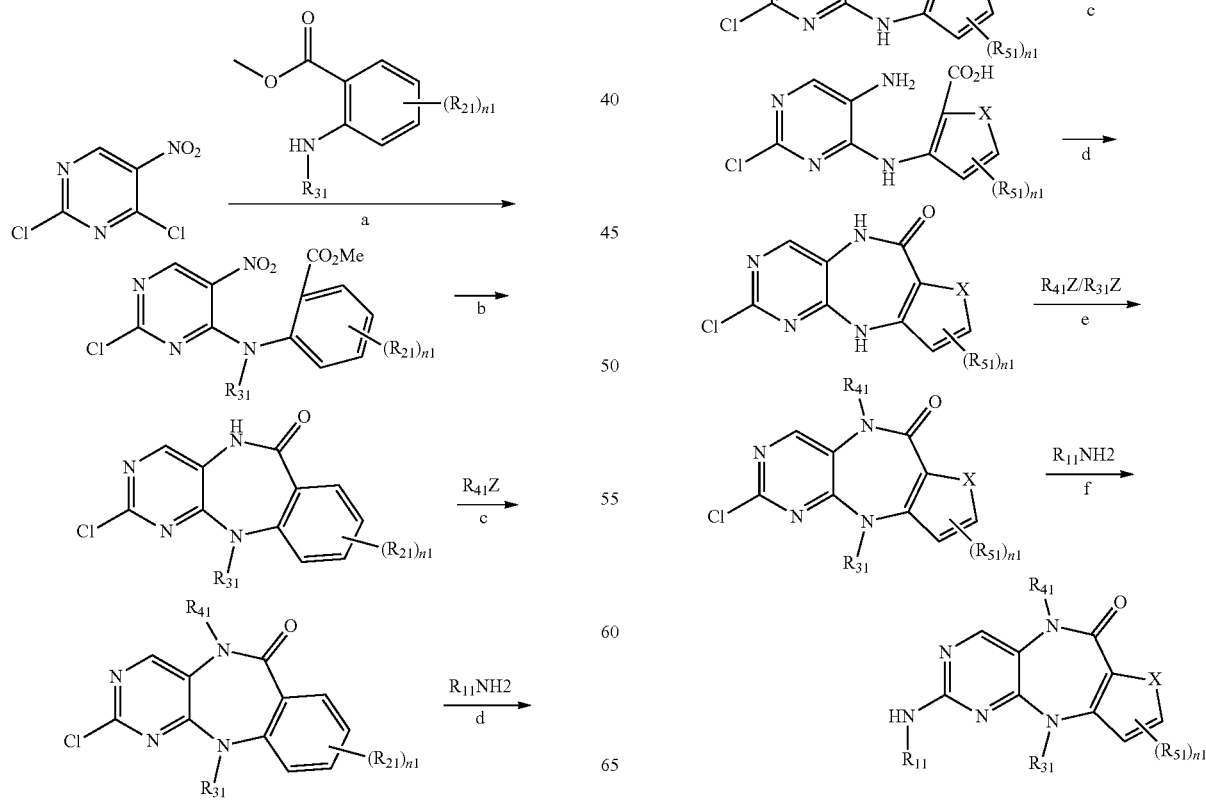

Reaction conditions: (a) basic conditions (such as diisopropylethylamine, triethylamine, potassium carbonate, etc.) in the substitution reaction; (b) nitro reduction (e.g., iron/acetic acid, etc.); (c) ester hydrolysis basic conditions (such as lithium hydroxide, etc.); (d) cyclizing the amide condensation (e.g., 2-(7-azo-benzotriazole)-N, N, N ', N'-tetramethylurea hexafluorophosphate condensing agent, etc.); (e) a basic condition (e.g., sodium hydroxide, etc.); (f) acidic conditions (trifluoroacetic acid, hydrochloric acid, etc.) or palladium-catalyzed amination reaction; or

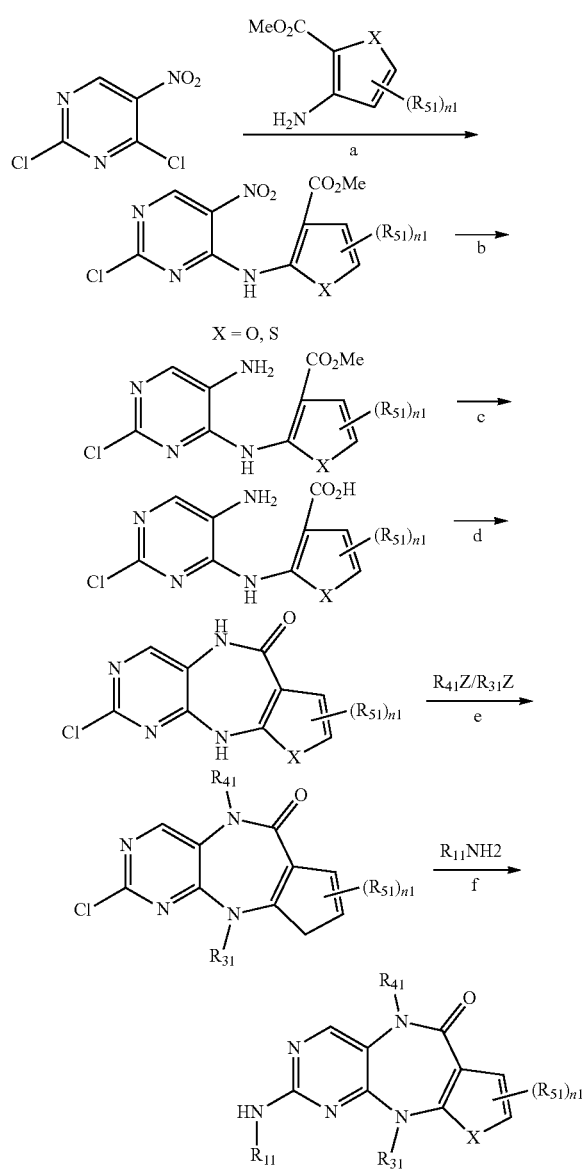

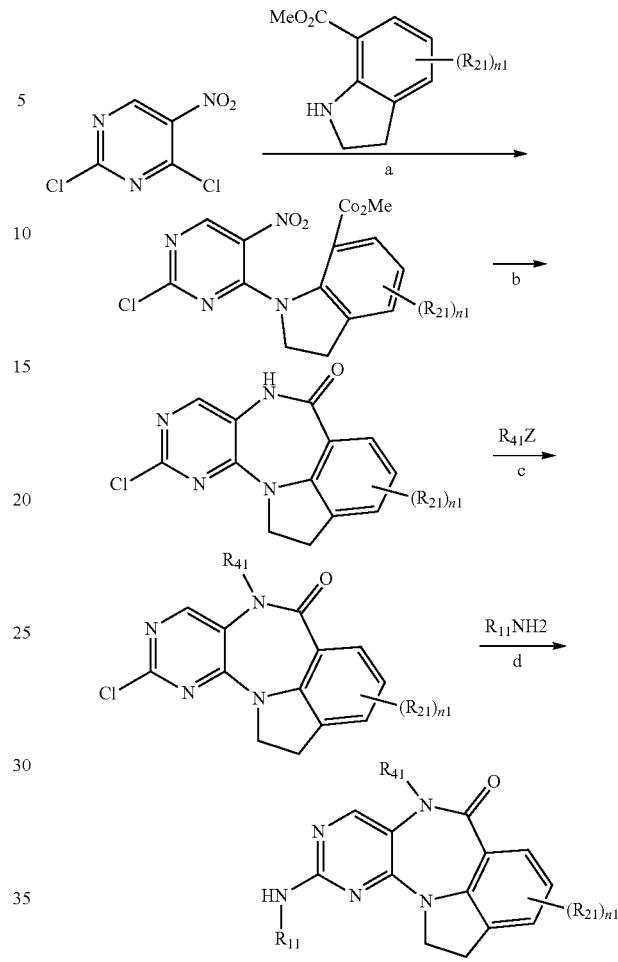

Reaction conditions: (a) basic conditions (such as diisopropylethylamine, triethylamine, potassium carbonate, etc.) in the substitution reaction; (b) nitro reduction (e.g., iron/ acetic acid, etc.); (c) ester hydrolysis basic conditions (such as lithium hydroxide, etc.); (d) cyclizing the amide condensation (e.g., 2-(7-azo-benzotriazole)-N, N, N N'-tetramethylurea hexafluorophosphate condensing agent, etc.); (e) a basic condition (e.g., sodium hydroxide, etc.); (f) acidic conditions (trifluoroacetic acid, hydrochloric acid, etc.) or palladium-catalyzed amination reaction; or Reaction conditions: (a) a basic condition (e.g., diisopropylethyl amine and the like); (b) nitro reduction and cyclization reaction of an amide (e.g., iron/acetic acid, etc.); (c) basic conditions (e.g. sodium hydrogen, etc.); amination reaction (d) acidic conditions (trifluoroacetic acid, hydrochloric acid, etc.) or palladium catalysis.

Another aspect, the present invention further provides any of the above aspect of the compound, a stereoisomer, a prodrug, or a pharmaceutically acceptable salt or a pharmaceutically acceptable solvate thereof and use of the pharmaceutical composition containing the compound of the present invention in the manufacture medicament for promoting tissue regeneration and repair of organs, to promote stem cell proliferation and somatic cell dedifferentiation, immunosuppression, preventing or treating a biological neurological disorders associated diseases and vascular diseases associated with local ischemia. Preferably, wherein said promoting organ and tissue regeneration, repair and regeneration is regeneration and repair of liver, regeneration and repair of intestine, repair and regeneration of heart, regeneration and repair of skin; wherein said prevention or treatment of neurological disorders associated disease is Alzheimer's disease, multiple sclerosis, Parkinson's disease, stroke.

EXAMPLES

Relates to the following examples, the compounds of the present invention using the methods described herein or other methods known in the art of synthesis.

General Purification and Analytical Methods

Thin layer chromatography on precoated silica gel plates GF254 (Qingdao Ocean Chemical Plant). In the medium pressure over silica gel (300-400 mesh, silica gel developed Yantai Chi Huangwu Reagent Factory) was subjected to column chromatography or column chromatography using silica gel pre cartridge (ISCO or Welch) by using an ISCO Combiflash Rf200 rapid purification system. Component by UV light (λ: 254 nm) and by iodine vapor development. When necessary, the compound was prepared by preparative HPLC Waters Symmetry C18 (19×50 mm, 5 μm) column or by Waters×Terra RP 18 (30×150 mm, 5 μm) was purified by column, equipped with an 996Waters PDA detector Waters preparative HPLC 600 and Micromass mod.ZMD single quadrupole mass (electrospray ionization, positive ion mode). Method 1: Phase A: 0.1% TFA/MeOH 95/5; phase B: MeOH/H2 O 95/5. Gradient: 10 to 90% B for 8 mM, 2 min maintaining 90% B; flow rate of 20 mL/min. Method 2: Phase A: 0.05% NH 4 OH/MeOH 95/5; phase B: MeOH/H2 O 95/5. Gradient: 10 to 100% B for 8 mM, held 100% B 2 min. Flow rate 20 mL/min.

The $^1$H-NMR spectrum in DMSO-$d_6$ in CDCl$_3$ or the Bruker Avance 600 spectrometer via 600 MHz operation (for $^1$H concerned) recorded. The residual solvent signal used as reference (δ=2.50 or 7.27 ppm). Chemical shifts ([delta]) are reported in parts per million performed (ppm) and coupling constants (J) in Hz. The following abbreviations are used for splitting of peaks: s=singlet; br.s.=broad signal; d=double; t=three; m=multiple; dd=both.

Electrospray Ionization (ESI) Mass Spectrum Obtained by Finnigan LCQ Ion Trap.

Unless otherwise stated, all the final compounds were homogeneous (purity not less than 95%), as determined by high performance liquid chromatography (HPLC). HPLC-UV-MS analysis used to evaluate the purity of a compound HPLC system SSP4000 (Thermo Separation Products) is performed by a combination of the ion trap MS apparatus, the HPLC system equipped with an autosampler LC Pal (CTC Analytics) and a diode array UV6000LP detector (UV detection at 215-400 nm). Device control, data acquisition and processing using Xcalibur 1.2 software (Finnigan). HPLC chromatography is carried out at room temperature/min flow rate 1 mL, using a Waters×Terra RP 18 column (4.6×50 mm; 3.5 μm). Mobile phase A was ammonium acetate 5 mM buffer solution (using acetic acid to give pH 5.5): acetonitrile 90:10, and Mobile phase B 5 mM ammonium acetate buffer solution (using acetic acid to give pH 5.5): acetonitrile ten ninety; gradient of 0 to 100% B for 7 min, then hold 100% B for 2 minutes before re-Ping Heng.

Purification Reagent Reference Purification of Laboratory Chemicals (Perrin, D D, Armarego, W L F and Perrins Eds, D R; Pergamon Press: Oxford, 1980) for a book. Fraction is 60-90 deg.] C petroleum ether, ethyl acetate, methanol, methylene chloride were of analytical grade.

In the context of the following examples and embodiments of the present disclosure, the following abbreviations have the following meanings. If not defined, any terms should have their generally accepted meanings.

| Abbreviations | Full names |
| --- | --- |
| DMSO | Dimethyl sulfoxide |
| HCl | Hydrogen Chloride |
| MeOH | Methol |
| NaHCO$_3$ | Sodium Bicarbonate |
| NaOH | Sodium Hydroxide |
| TEA | Trifluoroacetate |

SPECIFIC EMBODIMENTS

The following description of the embodiments of the present invention in detail by way of specific embodiments, but in any case they are not to be construed as limiting the present invention.

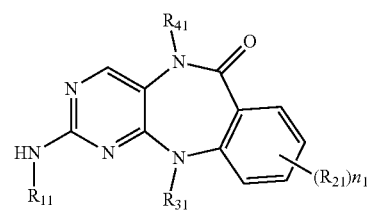

I

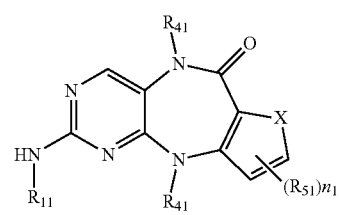

II (X = O,S)

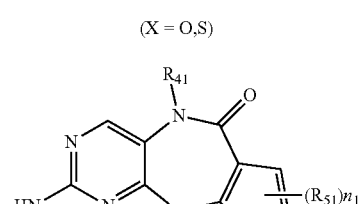

III (X = O,S)

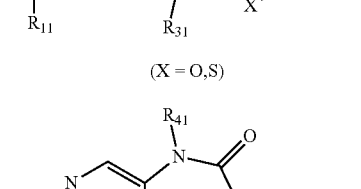

IV

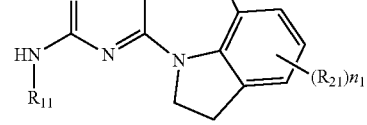

These compounds may be prepared using several synthetic routes.

Compounds of General Formula I

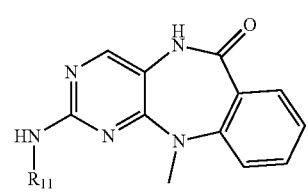

IA

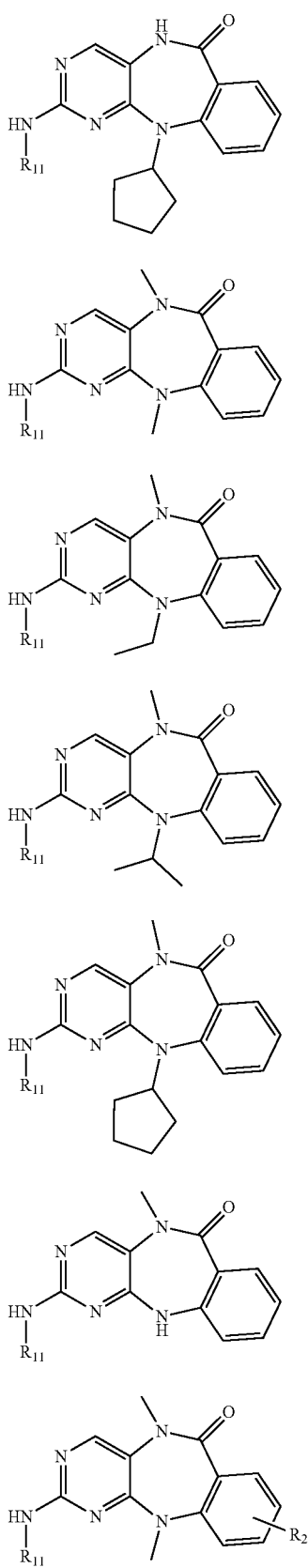

among them, synthesis of compounds of formula IA is

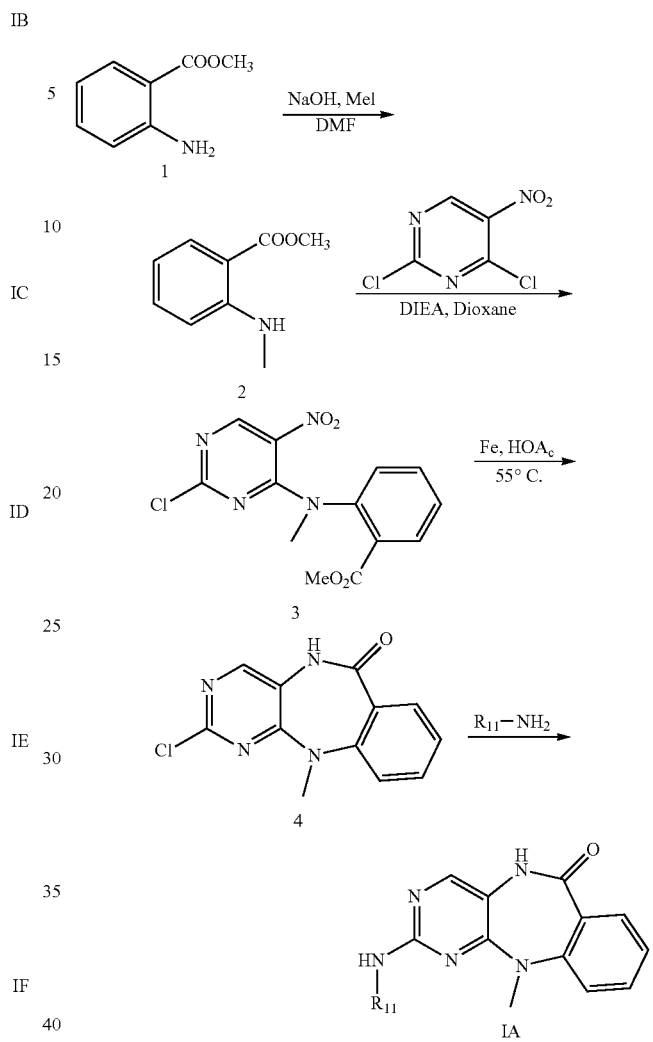

Preparation of Compound 2

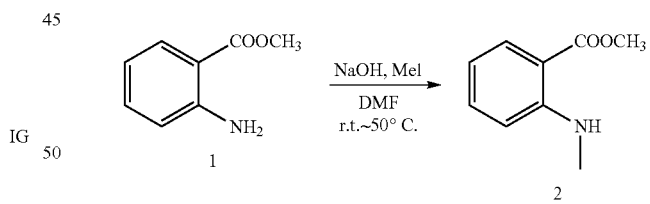

Compound 1 (4 g, 26.5 mmol), sodium hydroxide (1.4 g, 34.5 mmol) was dissolved in 20 mL of N, N-dimethylformamide was stirred at room temperature for 5 min, the system again iodomethane (1.65 mL, 26.5 mmol), stirred at room temperature 1 h, and finally placed in a preheated oil bath to 50 deg. C. and heated with stirring to complete the reaction of compound 1 (LC-MS and TLC track). The reaction was stopped, cooled to room temperature, the system was poured into a separatory funnel, ethyl acetate and water (1:1) fraction was extracted several times with ethyl acetate layer was washed with water, then brine, and finally dried over anhydrous sodium sulfate, and concentrated silica gel column chromatography (petroleum ether/ ethyl acetate=98/2) to give compound 2 (oily liquid, 2.4 g of, 57.0% yield), it was used directly in the next reaction. MS (ESI) m/z: 291 [M+H]+.

Preparation of Compound 3

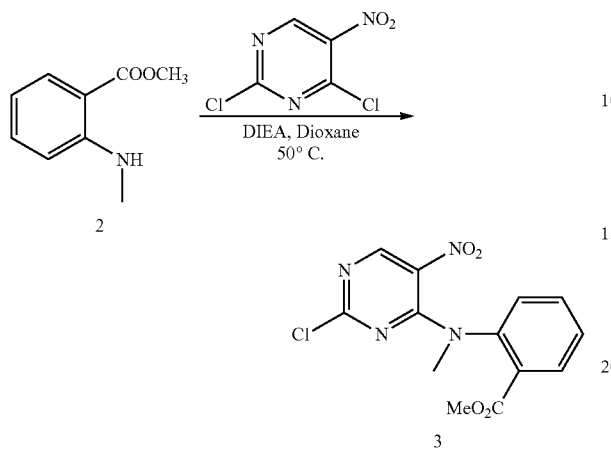

Compound 2 (2.4 g, 14.5 mmol), 2,4-dichloro-5-nitropyrimidine (2.8 g, 14.5 mmol) was dissolved in 30 mL 1,4-dioxane, was added N, N-two the reaction was stirred diisopropylethylamine (4.8 mL, 29.0 mmol), the resulting system is placed in a preheated oil bath to 50 deg. C., the reaction was complete to compound 2 (LC-MS and TLC track). The reaction was stopped, rotary evaporation, and concentrated by silica gel column chromatography (petroleum ether/ethyl acetate=10/1) to give compound 3 (3.9 g, yield 84.3%).

1H NMR (600 MHz, Methanol-d 4) δ8.54 (s, 1H), 8.02 (dd, J=7.8, 1.6 Hz, 1H), 7.66 (t, J=6 Hz, 1H), 7.49 (t, J=6 Hz, 1H), 7.38 (dd, J=7.9, 1.2 Hz, 1H), 3.79 (s, 3H), 3.55 (s, 3H). MS (ESI) m/z: 323 [m+H]+

Preparation of Compound 4

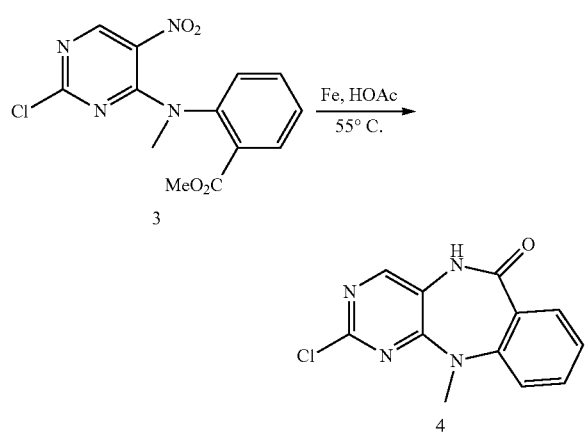

Compound 3 (3.7 g, 11.6 mmol) was dissolved in 30 mL of acetic acid, was added iron powder (6.5 g, 116 mmol), the system was placed under the reaction was heated with stirring to 55° C. had been preheated oil bath overnight (LC-MS and TLC detecting completion of the reaction), the reaction is stopped, the system was poured into ice water, and the precipitated solid was filtered with a Buchner funnel, the filter cake was washed several times with ice water and acetic acid salts, drained and finally the solid was collected to give compound 4 (1.5 g, 49.6% yield).

1H NMR (600 MHz, DMSO-d 6) δ0.46 (s, 1H), 8.15 (s, 1H), 7.73 (dd, J=7.8, 1.8 Hz, 1H), 7.59 (ddd, J=8.9, 7.2, 1.8 Hz, 1H), 7.28 (dd, J=8.3, 1.0 Hz, 1H), 7.22 (td, J=7.5, 1.0 Hz, 1H), 3.35 (s, 3H). MS (ESI) m/z: 261 [M$^+$H]+

Preparation of Compound IA

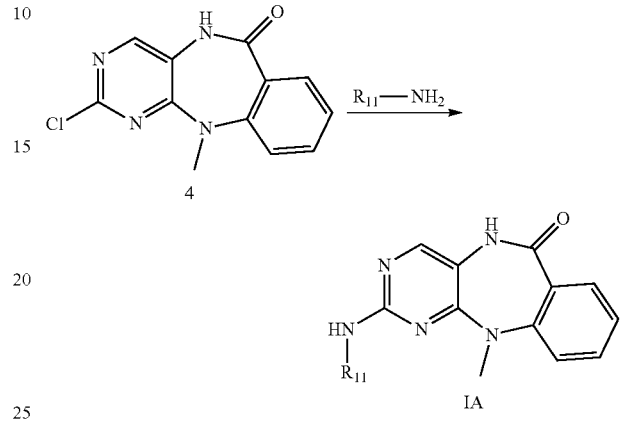

Method A:

Compound 4 (26 mg, 0.1 mmol) and aromatic amines (0.1 mmol) was dissolved in 1 mL sec-butanol, was added a 4N HCl solution (50 μL, 0.2 mmol), and finally placed in a closed system has been preheated to 110 deg.] C. oil bath heated with stirring until the reaction was complete (LC-MS and TLC monitoring). The reaction was stopped, the reaction solution was transferred to a centrifuge tube 2 mL of adding a certain amount of petroleum ether, shaking, centrifugation, supernatant liquid was discarded, a small amount of methanol was added, along with petroleum ether, the above operation is repeated until the supernatant liquid became clear until the solid was collected, spin-dried and weighed as compound IA.

Method B:

Compound 4 (26 mg, 0.1 mmol) and aromatic amines (0.1 mmol) was dissolved in 1 mL sec-butanol, was added a 4N HCl solution (50 μL, 0.2 mmol), and finally placed in a closed system has been preheated to 110 deg.] C. oil bath heated with stirring until the reaction was complete (LC-MS and TLC monitoring). The reaction was stopped, concentrated and purified by reverse phase preparative HPLC (containing 0.35% aqueous trifluoroacetic acid and methanol as mobile phase), dried and concentrated in vacuo to yield compound IA.

Method C:

Compound 4 (26 mg, 0.1 mmol), aromatic amines (0.1 mmol) was dissolved in 1 ml tert-butanol, was added tris (dibenzylideneacetone) dipalladium (5.5 mg, 0.006 mmol), 2-dicyclohexyl phosphate 2,4,6-triisopropyl-biphenyl (4.3 mg, 0.009 mmol) and potassium carbonate (55.3 mg, 0.4 mmol), drainage systems nitrogen and placed in an oil bath preheated to 100° C. heated with stirring after 5 h the reaction was stopped. System filtered through a fritted funnel off the solid, the liquid was collected and concentrated by silica gel column chromatography to obtain compound IA.

Compound IB, IC, ID, IE, IF, IG, IH can be synthesized using similar methods.

The following table 1 lists specific compounds and their properties.

TABLE 1

Structure and characterization of compound IA-IH

| No. | Structure | Data of NMR and/or Mass Spectro. |
| --- | --- | --- |
| IA-1 | (structure shown; TFA salt) | $^1$H NMR (600 MHz, DMSO-d$_6$) δ 10.14 (s, 1H), 9.96 (s, 1H), 8.38 (s, 1H), 8.06 (s, 1H), 7.92 (d, J = 8.5 Hz, 1H), 7.72 (d, J = 7.7 Hz, 1H), 7.65 (d, J = 8.5 Hz, 1H), 7.54 (t, J = 7.7 Hz, 1H), 7.24 (d, J = 8.3 Hz, 1H), 7.17 (t, J = 7.4 Hz, 1H), 3.90 (s, 2H), 3.54 (s, 2H), 3.39 (s, 3H), 3.17 (d, J = 7.1 Hz, 4H), 2.71 (s, 2H), 2.54 (s, 2H), 1.21 (t, J = 7.2 Hz, 3H), $^{13}$C NMR (151 MHz, DMSO-d$_6$) δ 167.6, 160.9, 155.5, 149.3, 148.4, 140.8, 133.3, 132.2, 131.5, 126.1, 125.3, 123.7, 121.5, 118.9, 116.6, 115.2, 114.7, 56.3, 50.7, 49.8, 49.1, 36.3, 8.9, MS (ESI) m/z: 512 [M + H]$^+$. |
| IA-2 | (structure shown) | $^1$H NMR (600 MHz, DMSO-d$_6$) δ 10.15 (s, 1H), 10.06 (s, 1H), 8.08 (s, 1H), 7.99 (d, J = 8.9 Hz, 2H), 7.72 (dd, J = 7.8, 1.7 Hz, 1H), 7.63 (d, J = 8.9 Hz, 2H), 7.56 (t, 1H), 7.28 (d, J = 8.2 Hz, 1H), 7.19 (t, J = 7.5 Hz, 1H), 3.41 (s, 3H), 2.86 (s, 4H), 2.35 (s, 4H), 2.13 (s, 3H). MS (ESI) m/z: 480 [M + H]$^+$. |
| IA-3 | (structure shown) | $^1$H NMR (600 MHz, DMSO) δ 10.15 (s, 1H), 10.05 (s, 1H), 8.08 (s, 1H), 7.98 (d, J = 8.9 Hz, 2H), 7.72 (dd, J = 7.7, 1.7 Hz, 1H), 7.63 (d, J = 8.9 Hz, 2H), 7.57-7.53 (m, 1H), 7.28 (J = 8.2 Hz, 1H), 7.18 (t, J = 7.4 Hz, 1H), 3.53-3.49 (m, 1H), 3.41 (s, 3H), 3.14 (s, 2H), 2.68 (t, J = 8.4 Hz, 2H), 1.76-1.71 (m, 2H), 1.46-1.39 (m, 2H), MS (ESI) m/z: 481 [M + H]$^+$. |

TABLE 1-continued

Structure and characterization of compound IA-IH

| No. | Structure | Data of NMR and/or Mass Spectro. |
|---|---|---|
| IA-4 | 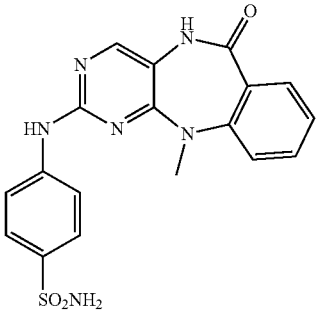 [SMILES: CN1c2ccccc2C(=O)Nc2cnc(Nc3ccc(S(N)(=O)=O)cc3)nc21]<br>TFA salt | ¹H NMR (600 MHz, DMSO) δ 9.91 (s, 1H), 8.07 (s, 1H), 7.89 (d, J = 8.9 Hz, 2H), 7.74-7.69 (m, 3H), 7.57-7.52 (m, 1H), 7.28 (d, J = 8.2 Hz, 1H), 7.18 (dd, J = 11.0, 4.0 Hz, 2H), 3.39 (s, 3H), ¹³C NMR (151 MHz, DMSO) δ 167.5, 160.8, 155.4, 149.3, 148.5, 143.7, 135.8, 133.2, 131.4, 126.6, 126.0, 123.6, 119.0, 117.5, 116.7, 36.4. MS (ESI) m/z: 397 [M + H]⁺. |
| IA-5 | 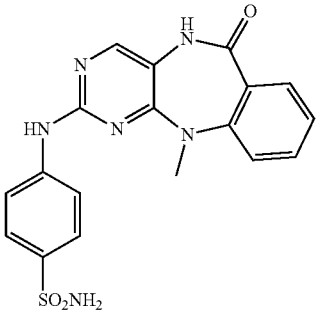 [SMILES: CN1c2ccccc2C(=O)Nc2cnc(Nc3ccc(S(N)(=O)=O)cc3)nc21]<br>HCl salt | ¹H NMR (600 MHz, DMSO-d₆) δ 10.18 (s, 1H), 10.02 (s, 1H), 8.07 (s, 1H), 7.89 (s, 1H), 7.88 (s, 1H), 7.76-7.70 (m, 3H), 7.59-7.54 (m, 1H), 7.29 (d, J = 8.3 Hz, 1H), 7.19 (t, J = 7.5 Hz, 1H), 3.40 (s, 3H). ¹³C NMR (151 MHz, DMSO-d₆) δ 167.9, 161.5, 155.4, 148.7, 148.6, 143.9, 136.6, 133.7, 131.8, 127.0. 126.4, 124.2, 119.6, 118.2, 117.1, 37.0. MS (ESI) m/z: 397 [M + H]⁺. |
| IA-6 | 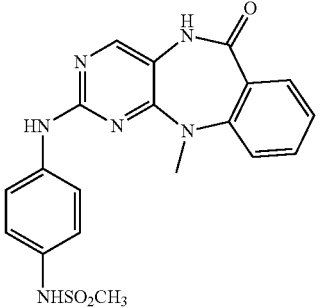<br>HCl salt | ¹H NMH (600 MHz, DMSO-d₆) δ 10.16 (s, 1H), 9.89 (s, 1H), 9.54 (s, 1H), 8.00 (s, 1H), 7.73 (dd, J = 7.8, 1.7 Hz, 1H), 7.66 (d, J = 8.9 Hz, 2H), 7.56 (t, 1H), 7.30 (d, J = 8.4 Hz, 1H), 7.23-7.17 (m, 3H), 3.39 (s, 3H), 2.94 (s, 3H). ¹³C NMR (151 MHz, DMSO-d₆) δ 167.7, 162.3, 154.6, 148.0, 146.2, 136.7, 133.7, 132.9, 131.8, 126.3, 124.4, 122.1, 120.6, 119.8, 116.0, 49.1, 37.2, MS (ESI) m/z: 411 [M + H]⁺. |
| IA-7 | 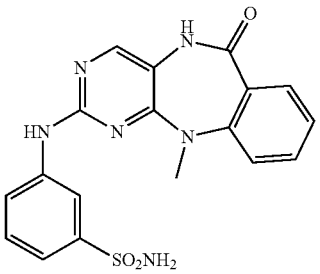 [SMILES: CN1c2ccccc2C(=O)Nc2cnc(Nc3cccc(S(N)(=O)=O)c3)nc21]<br>HCl salt | ¹H NMR (600 MHz, DMSO-d₆) δ 10.16 (s, 1H), 9.98 (s, 1H), 8.53 (t, J = 2.1 Hz, 1H), 8.05 (s, 1H), 7.73 (ddd, J = 7.8, 5.9, 1.8 Hz, 2H), 7.57 (ddd, J = 8.8, 7.2, 1.8 Hz, 1H), 7.47 (t, J = 7.9 Hz, 1H), 7.41 (dt, J = 7.7, 1.4 Hz, 1H), 7.25 (d, J = 8.3 Hz, 1H), 7.19 (t, J = 7.5 Hz, 1H), 3.42 (s, 3H). ¹³C NMR (151 MHz, DMSO-d₆) δ 167.9, 161.6, 155.5, 148.7, 148.6, 145.0, 141.1, 133.7, 131.8, 129.6, 126.4, 124.1, 121.9, 119.5, 118.8, 116.7, 115.8, 37.1. MS (ESI) m/z: 397 [M + H]⁺. |

TABLE 1-continued

Structure and characterization of compound IA-IH

| No. | Structure | Data of NMR and/or Mass Spectro. |
|---|---|---|
| IB-1 | 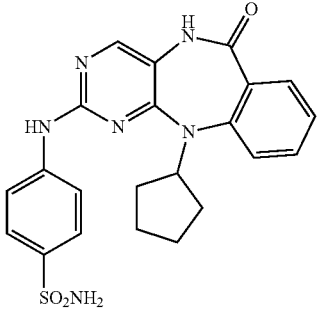 [SMILES: NS(=O)(=O)c1ccc(Nc2ncc3c(n2)N(C2CCCC2)c2ccccc2C(=O)N3)cc1]<br>TFA salt | $^1$H NMR (600 MHz, DMSO-d$_6$) δ 10.20 (s, 1H), 9.93 (s, 1H), 8.12 (s, 1H), 7.90 (d, J = 8.9 Hz, 2H), J = 7.74 -7.70 (m, 2H), 7.61 (dd, J = 7.7, 1.7 Hz, 1H), 7.52 (ddd, J = 8.8, 7.3, 1.7 Hz, 1H), 7.35 (dd, J = 8.4, 1.0 Hz, 1H), 7.20 (td, J = 7.5, 1.0 Hz, 1H), 7.16 (s, 2H), 4.82-4.71 (m, 1H), 2.34 (s, 1H), 2.11 (s, 1H), 1.65-1.54 (m, 4H), 1.41 (s, 2H). MS (ESI) m/z: 451 [M + H]$^+$. |
| IB-2 | 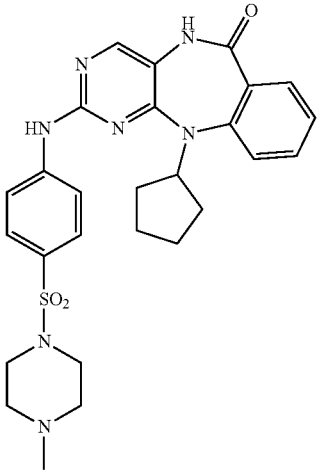 [SMILES: CN1CCN(S(=O)(=O)c2ccc(Nc3ncc4c(n3)N(C3CCCC3)c3ccccc3C(=O)N4)cc2)CC1]<br>TFA salt | $^1$H NMR (600 MHz, DMSO-d$_6$) δ 10.23 (s, 1H), 10.10 (s, 1H), 8.14 (s, 1H), 8.01 (d, J = 8.9 Hz, 2H), 7.65 (d, J = 8.9 Hz, 2H), 7.61 (dd, J = 7.7, 1.6 Hz, 1H), 7.55-7.50 (m, 1H), 7.34 (d, J = 8.2 Hz, 1H), 7.20 (t, J = 7.5 Hz, 1H), 4.82-4.74 (m, 1H), 2.89 (s, 4H), 2.33 (s, 3H), 2.12 (s, 1H), 1.60 (s, 4H), 1.42 (s, 2H), 1.33 (s, 1H), 1.23 (d, J = 5.3 Hz, 2H), 1.04 (d, J = 6.1 Hz, 2H). MS (ESI) m/z: 534 [M + H]$^+$. |
| IB-3 | 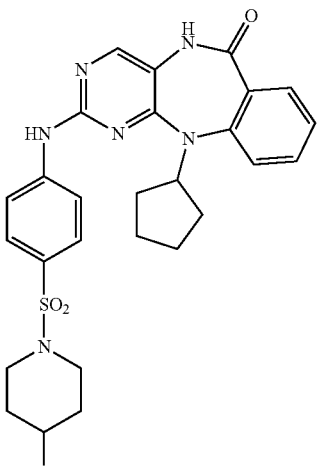<br>TFA salt | $^1$H NMR (600 MHz, DMSO) δ 10.22 (s, 1H), 10.06 (s, 1H), 8.13 (s, 1H), 7.99 (d, J = 9.0 Hz, 2H), 7.65-7.59 (m, 3H), 7.54-7.50 (m, 1H), 7.35 (d, J = 8.1 Hz, 1H), 7.20 (dd, J = 11.6, 4.3 Hz, 1H), 4.81-4.75 (m, 1H), 3.55-3.47 (m, 1H), 3.14 (s, 2H), 2.68 (t, J = 8.7 Hz, 2H), 2.34 (s, 1H), 2.12 (s, 1H), 1.77-1.69 (m, 2H), 1.59 (s, 4H), 1.47-1.37 (m, 4H). MS (ESI) m/z: 535 [M + H]$^+$. |

TABLE 1-continued

Structure and characterization of compound IA-IH

| No. | Structure | Data of NMR and/or Mass Spectro. |
| --- | --- | --- |
| IB-4 | 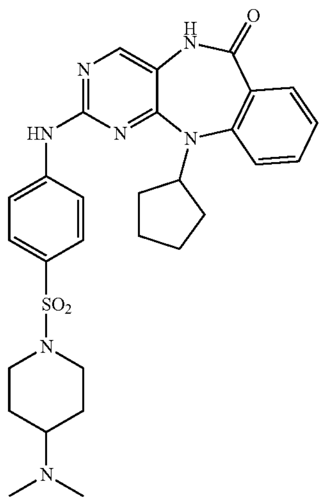 [SMILES: CN(C)C1CCN(S(=O)(=O)c2ccc(Nc3ncc4c(n3)N(C3CCCC3)c3ccccc3C(=O)N4)cc2)CC1] | MS (ESI) m/z: 562 [M + H]+ |
| IB-5 | 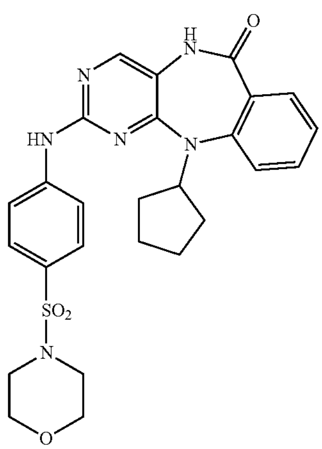 [SMILES: O=C1Nc2cnc(Nc3ccc(S(=O)(=O)N4CCOCC4)cc3)nc2N(C2CCCC2)c2ccccc21] | MS (ESI) m/z: 521 [M + H]+ |
| IB-6 | 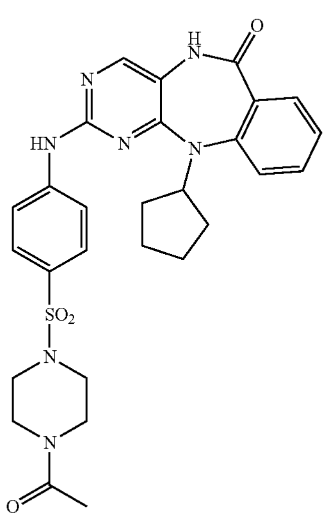 [SMILES: CC(=O)N1CCN(S(=O)(=O)c2ccc(Nc3ncc4c(n3)N(C3CCCC3)c3ccccc3C(=O)N4)cc2)CC1] | MS (ESI) m/z: 562 [M + H]+ |

TABLE 1-continued

Structure and characterization of compound IA-IH

| No. | Structure | Data of NMR and/or Mass Spectro. |
|---|---|---|
| IB-7 | (structure) | MS (ESI) m/z: 620 [M + H]+ |
| IC-1 | (structure) | $^1$H NMR (600 MHz, MeOD) δ 8.35 (s, 1H), 7.91-7.88 (m, 2H), 7.84-7.81 (m, 2H), 7.75 (dd, J = 7.8, 1.7 Hz, 1H), 7.54-7.50 (m, 1H), 7.25 (d, J = 7.7 Hz, 1H), 7.18 (t, J = 7.5 Hz, 1H), 3.50 (s, 3H), 3.45 (s, 3H). MS (ESI) m/z: 411 [M + H]+. |
| IC-2 | (structure) TFA salt | $^1$H NMR (600 MHz, DMSO) δ 10.27 (s, 1H), 8.50 (s, 1H), 8.05 (d, J = 8.8 Hz, 2H), 7.71 (d, J = 9.0 Hz, 3H), 7.52 (t, J = 7.1 Hz, 1H), 7.28 (d, J = 8.0 Hz, 1H), 7.19 (t, J = 7.5 Hz, 1H), 3.74 (s, 2H), 3.46 (s, 3H), 3.42 (s, 3H), 3.41 (s, 3H), 3.15 (s, 2H), 2.78 (s, 4H). MS (ESI) m/z: 494 [M + H]+. |

TABLE 1-continued

Structure and characterization of compound IA-IH

| No. | Structure | Data of NMR and/or Mass Spectro. |
|---|---|---|
| IC-3 | 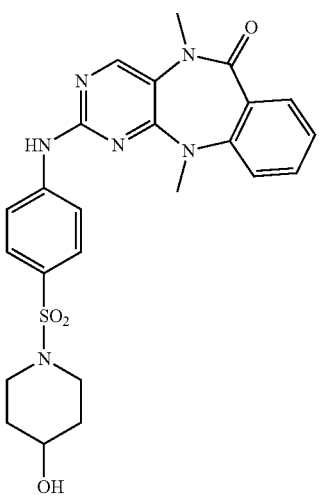 [SMILES: CN1C(=O)c2ccccc2N(C)c2nc(Nc3ccc(S(=O)(=O)N4CCC(O)CC4)cc3)ncc21]<br>TFA salt | $^1$H NMR (600 MHz, DMSO-d$_6$) δ 10.19 (s, 1H), 8.49 (s, 1H), 8.01 (d, J = 8.9 Hz, 2H), 7.71 (dd, J = 7.7, 1.8 Hz, 1H), 7.66 (d, J = 8.9 Hz, 2H), 7.53 (ddd, J = 8.8, 7.3, 1.8 Hz, 1H), 7.29 (dd, J = 8.5, 1.0 Hz, 1H), 7.20 (td, J = 7.5, 1.0 Hz, 1H), 3.56-3.50 (m, 1H), 3.43 (s, 3H), 3.41 (s, 3H), 3.16 (d, J = 21.7 Hz, 2H), 2.70 (t, J = 8.6 Hz, 2H), 1.79-1.71 (m, 2H), 1.49-1.39 (m, 2H). MS (ESI) m/z: 495 [M + H]$^+$. |
| IC-4 | 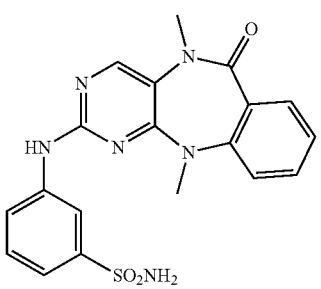 [SMILES: CN1C(=O)c2ccccc2N(C)c2nc(Nc3cccc(S(N)(=O)=O)c3)ncc21]<br>TFA salt | $^1$H NMS (600 MHz, DMSO-d$_6$) δ 9.99 (s, 1H), 8.55 (t, J = 2.0 Hz, 1H), 8.45 (s, 1H), 7.76 (dd, J = 8.4, 2.2 Hz, 1H), 7.70 (dd, J = 7.8, 1.7 Hz, 1H), 7.53 (ddd, J = 8.6, 7.2, 1.8 Hz, 1H), 7.48 (t, J = 7.9 Hz, 1H), 7.42 (d, J = 7.7, 1.4 Hz, 1H), 7.31 (s, 2H), 7.25 (d, J = 8.3 Hz, 1H), 7.19 (t, J = 7.7 Hz, 1H), 3.42 (s, 3H), 3.40 (s, 3H). MS (ESI) m/z: 411 [M + H]$^+$. |
| IC-5 | 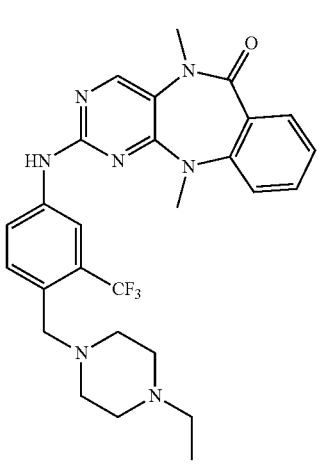 [SMILES: CCN1CCN(Cc2ccc(Nc3ncc4c(n3)N(C)c3ccccc3C(=O)N4C)cc2C(F)(F)F)CC1]<br>TFA salt | $^1$H NHR (600 MHz, DMSO) δ 10.05 (s, 1H), 8.46 (s, 1H), 8.38 (s, 1H), 7.91 (d, J = 8.5 Hz, 1H), 7.69 (dd, J = 7.7, 1.3 Hz, 1H), 7.65 (d, J = 8.6 Hz, 1H), 7.51 (t, J = 7.7 Hz, 1H), 7.25 (d, J = 8.3 Hz, 1H), 7.18 (t, J = 7.5 Hz, 1H), 3.78 (s, 2H), 3.50 (s, 2H), 3.41 (s, 3H), 3.38 (s, 3H), 3.16 (q, J = 7.2 Hz, 2H), 3.04 (s, 4H), 2.55 (t, J = 5.6 Hz, 2H), 1.21 (t, J = 7.3 Hz, 3H). MS (ESI) m/z: 526 [M + H]$^+$. |

TABLE 1-continued

Structure and characterization of compound IA-IH

| No. | Structure | Data of NMR and/or Mass Spectro. |
|---|---|---|
| IC-6 | 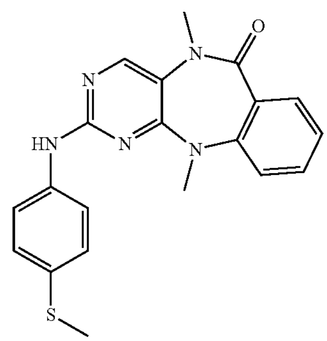 [SMILES: CSc1ccc(Nc2ncc3c(n2)N(C)c2ccccc2C(=O)N3C)cc1] | $^1$H NMR (600 MHz, DMSO-d$_6$) δ 9.65 (s, 1H), 8.39 (s, 1H), 7.72 (d, J = 8.7 Hz, 2H), 7.68 (d, J = 7.7, 1.6 Hz, 1H), 7.49 (t, 1H), 7.24 (dd, J = 8.8, 2.4 Hz, 3H), 7.16 (t, J = 7.5 Hz, 1H), 3.40 (s, 3H), 3.34 (s, 3H), 2.44 (s, 3H). MS (ESI) m/z: 378 [M + H]$^+$. |
| IC-7 | 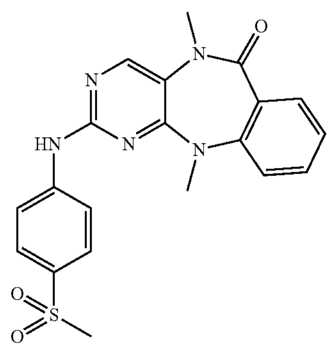 [SMILES: CN1C(=O)c2ccccc2N(C)c2nc(Nc3ccc(S(C)(=O)=O)cc3)ncc21] | $^1$H NMR (600 MHz, DMSO-d$_6$) δ 10.26 (s, 1H), 8.49 (s, 1H), 7.99 (d, J = 8.9 Hz, 2H), 7.83 (d, J = 8.9 Hz, 2H), 7.69 (dd, J = 7.8, 1.7 Hz, 1H), 7.52 (t, J = 8.6, 7.3, 1.7 Hz, 1H), 7.27 (d, J = 8.1 Hz, 1H), 7.18 (t, 1H), 3.41 (s, 3H), 3.40 (s, 3H), 3.18 (s, 3H). MS (ESI) m/z: 410 [M + H]$^+$. |
| IC-8 | 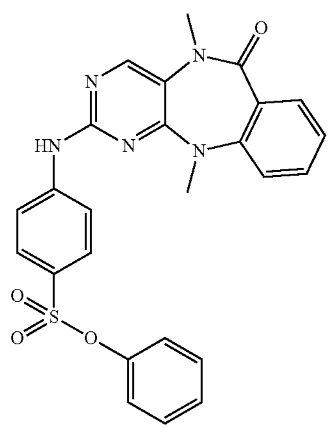 [SMILES: CN1C(=O)c2ccccc2N(C)c2nc(Nc3ccc(S(=O)(=O)Oc4ccccc4)cc3)ncc21] | $^1$H NMR (600 MHz, DMSO) δ 10.33 (s, 1H), 8.50 (s, 1H), 8.00 (d, J = 9.0 Hz, 2H), 7.75 (d, J = 9.0 Hz, 2H), 7.70 (dd, J = 7.8, 1.7 Hz, 1H), 7.54-7.50 (m, 1H), 7.38 (dd, J = 11.1, 4.6 Hz, 2H), 7.30 (t, J = 7.4 Hz, 1H), 7.27 (d, J = 8.1 Hz, 1H), 7.19 (t, J = 7.5 Hz, 1H), 7.04-7.01 (m, 2H), 3.42 (s, 3H), 3.39 (s, 3H). MS (ESI) m/z: 488 [M + H]$^+$. |
| IC-9 | 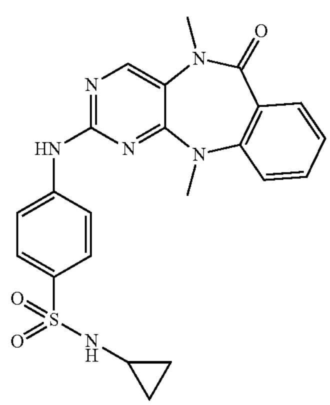 [SMILES: CN1C(=O)c2ccccc2N(C)c2nc(Nc3ccc(S(=O)(=O)NC4CC4)cc3)ncc21] | $^1$H NMR (600 MHz, DMSO-d$_6$) δ 10.19 (s, 1H), 8.46 (s, 1H), 7.95 (d, J = 8.8 Hz, 2H), 7.73 (d, J = 8.8 Hz, 2H), 7.69 (d, 1H), 7.51 (t, 1H), 7.28 (d, J = 8.3 Hz, 1H), 7.18 (t, J = 7.5 Hz, 1H), 3.41 (s, 3H), 3.40 (s, 3H), 2.13-2.06 (m, 1H), 0.50-0.43 (m, 2H), 0.40-0.32 (m, 2H). MS (ESI) m/z: 451 [M + H]$^+$. |

TABLE 1-continued

Structure and characterization of compound IA-IH

| No. | Structure | Data of NMR and/or Mass Spectro. |
|---|---|---|
| IC-10 | 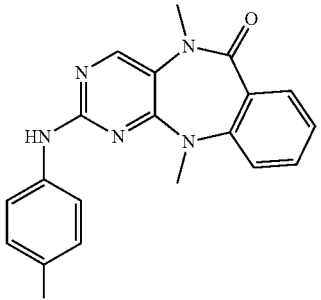<br>HCl salt | $^1$H NMR (600 MHz, DMSO-d$_6$) δ 9.83 (s, 1H), 9.52 (s, 1H), 8.39 (s, 1H), 7.71-7.66 (m, 3H), 7.51 (ddd, J = 8.7, 7.2, 1.7 Hz, 1H), 7.28 (dd, J = 8.4, 1.0 Hz, 1H), 7.21-7.16 (m, 3H), 3.40 (s, 3H), 3.37 (s, 3H), 2.94 (s, 3H). $^{13}$C NMR (151 MHz, DMSO-d$_6$) δ 167.5, 163.9, 155.2, 150.9, 149.1, 137.0, 133.1, 132.7, 132.1, 126.5, 124.2, 122.2, 120.7, 120.4, 118.5, 39.3, 38.1, 36.3. MS (ESI) m/z: 425 [M + H]$^+$. |
| IC-11 | 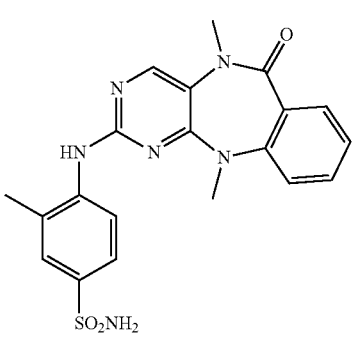 [SMILES: Cc1cc(S(N)(=O)=O)ccc1Nc1ncc2c(n1)N(C)c1ccccc1C(=O)N2C]<br>TFA salt | $^1$H NMR (600 MHz, DMSO-d$_6$) δ 11.25 (s, 1H), 8.38 (s, 1H), 7.66 (dd, J = 7.8, 1.7 Hz, 1H), 7.54 (s, 1H), 7.51 (dd, J = 6.7, 4.3 Hz, 2H), 7.23-7.14 (m, 2H), 6.63 (d, J = 8.5 Hz, 1H), 5.77 (d, J = 12.6 Hz, 2H), 3.34 (s, 3H), 3.23 (s, 3H), 2.08 (s, 3H). $^{13}$C NMR (151 MHz, DMSO-d$_6$) δ 167.3, 153.2, 151.7, 149.4, 133.1, 132.3, 130.4, 127.7, 126.3, 124.1, 120.2, 118.1, 112.7, 37.8, 36.2, 17.7. MS (ESI) m/z: 425 [M + H]$^+$. |
| ID-1 | 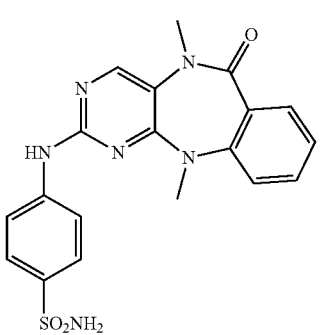<br>HCl salt | $^1$H NMR (600 MHz, DMSO-d$_6$) δ 10.12 (s, 1H), 8.50 (s, 1H), 7.90 (s, 1H), 7.89 (s, 1H), 7.76 (s, 1H), 7.75 (s, 1H), 7.66 (dd, J = 7.8. 1.7 Hz, 1H), 7.51 (ddd, J = 8.6, 7.3, 1.7 Hz, 1H), 7.27 (d, J = 8.4 Hz, 1H), 7.19 (t, J = 7.5 Hz, 1H), 3.97 (s, 2H), 3.44 (s, 3H), 1.25 (t, J = 7.0 Hz, 3H). $^{13}$C NMR (151 MHz, DMSO-d$_6$) δ 167.6, 163.3, 155.7, 152.5, 148.9, 143.8, 136.7, 132.8, 131.9, 127.7, 127.1, 124.3, 122.7, 119.5, 118.1, 41.8, 37.7, 13.5. MS (ESI) m/z: 425 [M + H]$^+$. |
| ID-2 | 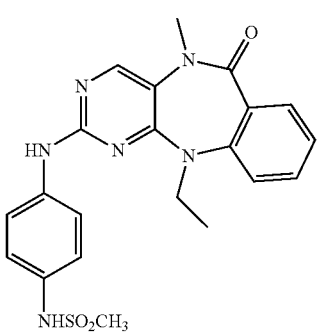<br>HCl salt | $^1$H NMR (600 MHz, DMSO-d$_6$) δ 9.81 (s, 1H), 9.52 (s, 1H), 8.42 (s, 1H), 7.69-7.64 (m, 3H), 7.50 (ddd, J = 8.6, 7.3, 1.7 Hz, 1H), 7.27 (d, J = 8.2 Hz, 1H), 7.20-7.16 (m, 3H), 3.94 (s, 2H), 3.42 (s, 3H), 2.94 (s, 3H), 1.24 (t, J = 7.0 Hz, 3H). $^{13}$C NMR (151 MHz, DMSO-d$_6$) δ 167.5, 163.8, 155.6, 151.4, 148.7, 137.2, 132.8, 132.6, 131.9, 127.8, 124.3, 122.2, 121.7, 120.2, 119.6, 41.8, 39.4, 37.7, 13.5. MS (ESI) m/z: 439 [M + H]$^+$. |

TABLE 1-continued

Structure and characterization of compound IA-IH

| No. | Structure | Data of NMR and/or Mass Spectro. |
|---|---|---|
| ID-3 | HCl salt | $^1$H NMR (600 MHz, DMSO-d$_6$) δ 10.05 (s, 1H), 8.50 (d, J = 2.1 Hz, 1H), 8.47 (s, 1H), 7.76 (dd, J = 8.1, 2.2 Hz, 1H), 7.66 (dd, J = 7.7, 1.6 Hz, 1H), 7.53-7.46 (m, 2H), 7.43 (d, J = 8.0 Hz, 1H), 7.23 (d, J = 8.3 Hz, 1H), 7.18 (t, J = 7.5 Hz, 1H), 3.97 (s, 2H), 3.43 (s, 3H), 1.24 (t, J = 7.0 Hz, 3H). $^{13}$C NMR (151 MHz, DMSO-d$_6$) δ 167.6, 163.4, 155.9, 152.5, 148.9, 145.0, 141.1, 132.8, 131.9, 129.8, 127.7, 124.3, 122.4, 121.9, 119.5, 119.0, 115.8, 41.8, 37.7, 13.5. MS (ESI) m/z: 425 [M + H]$^+$. |
| IE-1 | HCl salt | $^1$H NMR (600 MHz, DMSO-d$_6$) δ 10.11 (s, 1H), 8.53 (s, 1H), 7.91 (d, J = 2.0 Hz, 1H), 7.90 (s, 1H), 7.76 (s, 1H), 7.75 (s, 1H), 7.58 (dd, J = 7.8, 1.7 Hz, 1H), 7.48 (ddd, J = 8.8, 7.3, 1.7 Hz, 1H), 7.33 (dd, J = 8.3, 1.1 Hz, 1H), 7.18 (t, J = 7.5, 1.0 Hz, 1H), 4.51 (p, J = 6.0 Hz, 1H), 3.45 (s, 3H), 1.41 (d, J = 5.9 Hz, 3H), 1.28 (d, J = 6.1 Hz, 3H). $^{13}$C NMR (151 MHz, DMSO-d$_6$) δ 167.7, 163.5, 155.8, 152.7, 148.7, 143.8, 136.7, 132.2, 131.1, 129.2, 127.1, 124.8, 124.3, 122.2, 118.1, 47.1, 37.1, 22.5, 22.3. MS (ESI) m/z: 501 [M + H]$^+$. |
| IE-2 | TFA salt | $^1$H NMR (600 MHz, DMSO-d$_6$) δ 9.99 (s, 1H), 8.50 (s, 1H), 8.46 (t, J = 2.0 Hz, 1H), 7.82 (ddd, J = 8.1, 2.3, 1.1 Hz, 1H), 7.58 (dd, J = 7.8, 1.7 Hz, 1H), 7.48 (td, J = 7.7, 1.8 Hz, 2H), 7.43 (dt, J = 7.8, 1.3 Hz, 1H), 7.32 (s, 2H), 7.28 (dd, J = 8.4, 1.0 Hz, 1H), 7.18 (td, J = 7.5, 1.0 Hz, 1H), 4.54 (p, J = 6.0 Hz, 1H), 3.46 (s, 3H), 1.41 (d, J = 5.9 Hz, 3H), 1.26 (d, J = 6.1 Hz, 3H). $^{13}$C NMR (151 MHz, DMSO-d$_6$) δ 167.7, 163.4, 156.2, 153.0, 148.9, 145.0, 141.2, 132.1, 131.1, 129.6, 129.3, 124.7, 124.1, 122.1, 121.8, 118.9, 115.7, 62.5, 37.0, 25.9. MS (ESI) m/z: 439 [M + H]$^+$. |
| IE-3 | TFA salt | $^1$H NMR (600 MHz, DMSO-d$_6$) δ 9.65 (s, 1H), 9.45 (s, 1H), 8.43 (s, 1H), 7.70 (s, 1H), 7.68 (s, 1H), 7.57 (dd, J = 7.8, 1.6 Hz, 1H), 7.46 (td, J = 7.8, 1.7 Hz, 1H), 7.30 (d, J = 8.2 Hz, 1H), 7.17 (dd, J = 8.3, 6.8 Hz, 3H), 4.47 (p, J = 6.0 Hz, 1H), 3.43 (s, 3H), 2.93 (s, 3H), 1.40 (d, J = 5.9 Hz, 3H), 1.25 (d, J = 6.1 Hz, 3H). $^{13}$C NMR (151 MHz, DMSO-d$_6$) δ 167.7, 163.6, 156.4, 152.7, 148.8, 137.5, 132.3, 132.1, 131.1, 129.3, 124.7, 123.4, 122.3, 122.1, 120.0, 47.0, 37.0, 22.5, 22.3. MS (ESI) m/z: 453 [M + H]$^+$. |

TABLE 1-continued

Structure and characterization of compound IA-IH

| No. | Structure | Data of NMR and/or Mass Spectro. |
|---|---|---|
| IF-1 | 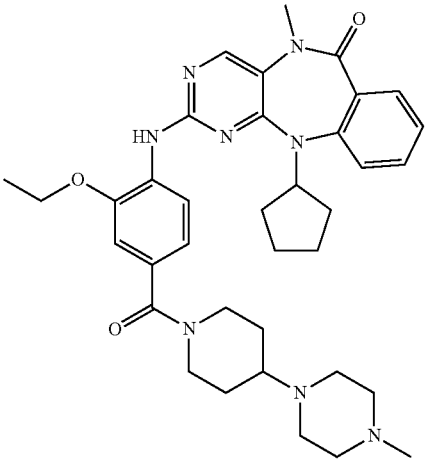 [SMILES: CCOc1cc(C(=O)N2CCC(N3CCN(C)CC3)CC2)ccc1Nc1ncc2c(n1)N(C1CCCC1)c1ccccc1C(=O)N2C] | MS (ESI) m/z: 639 [M + H]+. |
| IF-2 | 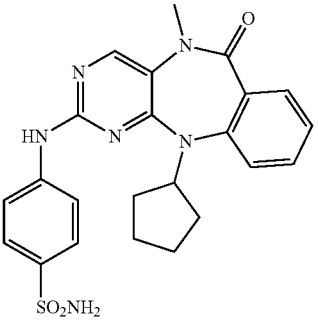 [SMILES: CN1C(=O)c2ccccc2N(C2CCCC2)c2nc(Nc3ccc(S(N)(=O)=O)cc3)ncc21]<br>HCl salt | $^1$H NMR (600 MHz, DMSO-d$_6$) δ 10.06 (s, 1H), 8.51 (s, 1H), 7.91 (d, J = 8.9 Hz, 2H), 7.74 (d, J = 8.9 Hz, 2H), 7.58 (dd, J = 7.8, 1.6 Hz, 1H), 7.47 (t, J = 8.8, 7.2, 1.7 Hz, 1H), 7.33 (d, J = 8.0 Hz, 1H), 7.17 (t, 1H), 4.79-4.69 (m, 1H), 3.44 (s, 3H), 2.37-2.30 (m, 1H), 2.15-2.09 (m, 1H), 1.65-1.57 (m, 4H), 1.55-1.47 (m, 1H), 1.45-1.37 (m, 1H). $^{13}$C NMR (151 MHz, DMSO-d$_6$) δ 167.7, 164.0, 156.1, 152.8, 149.6, 144.0, 136.6, 132.2, 131.1, 128.8, 127.1, 124.6, 124.0, 121.7, 117.9, 57.0, 37.1, 24.7, 24.5. MS (ESI) m/z: 465 [M + H]+. |
| IF-3 | 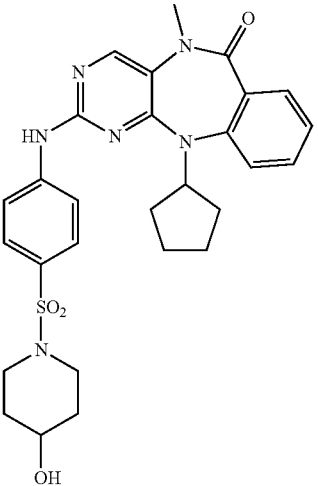 [SMILES: CN1C(=O)c2ccccc2N(C2CCCC2)c2nc(Nc3ccc(S(=O)(=O)N4CCC(O)CC4)cc3)ncc21] | $^1$H NMR (600 MHz, Acetone) δ 9.18 (s, 1H), 8.46 (s, 1H), 8.11 (d, J = 8.6 Hz, 2H), 7.72 (d, J = 8.7 Hz, 2H), 7.66 (d, J = 7.6 Hz, 1H), 7.46 (t, J = 7.4 Hz, 1H), 7.32 (d, J = 8.2 Hz, 1H), 7.17 (t, J = 7.5 Hz, 1H), 4.88-4.83 (m, 1H), 3.67 (s, 1H), 3.53 (s, 3H), 3.29 (s, 2H), 2.81 (s, 4H), 2.40 (d, J = 5.9 Hz, 1H), 2.17 (dd, J = 12.9, 6.3 Hz, 1H), 1.89-1.81 (m, 2H), 1.70-1.61 (m, 4H), 1.61-1.51 (m, 2H). MS (ESI) m/z: 549 [M + H]+. |

TABLE 1-continued

Structure and characterization of compound IA-IH

| No. | Structure | Data of NMR and/or Mass Spectro. |
|---|---|---|
| IF-4 | 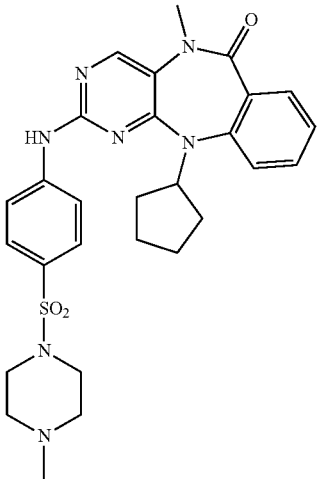 [SMILES: CN1CCN(S(=O)(=O)c2ccc(Nc3ncc4c(n3)N(C3CCCC3)c3ccccc3C(=O)N4C)cc2)CC1]<br>TFA salt | $^1$H NMR (600 MHz, DMSO) δ 10.27 (s, 1H), 8.53 (s, 1H), 8.05 (d, J = 9.0 Hz, 2H), 7.72 (d, J = 9.0 Hz, 2H), 7.59 (dd, J = 7.7, 1.7 Hz, 1H), 7.50-7.46 (m, 1H), 7.31 (d, J = 8.0 Hz, 1H), 7.18 (dd, J = 8.7, 5.4 Hz, 1H), 4.80-4.74 (m, 1H), 3.74 (s, 3H), 3.46 (s, 5H), 3.17 (s, 3H), 2.79 (s, 3H), 2.39-2.31 (m, 1H), 2.12 (dd, J = 12.3, 6.7 Hz, 1H), 1.62 (d, J = 6.9 Hz, 4H), 1.55-1.47 (m, 1H), 1.43 (dd, J = 13.2, 6.1 Hz, 1H). MS (ESI) m/z: 548 [M + H]$^+$. |
| IF-5 | 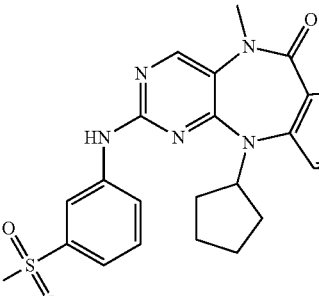<br>TFA salt | $^1$H NMR (600 MHz, DMSO-d$_6$) δ 9.99 (s, 1H), 8.54 (s, 1H), 8.48 (s, 1H), 7.78 (d, 1H), 7.58 (dd, J = 7.7, 1.6 Hz, 1H), 7.49-7.48 (m, 2H), 7.41 (d, J = 7.8 Hz, 1H), 7.31-7.27 (m, 3H), 7.17 (t, 1H), 4.85-4.71 (m, 1H), 3.44 (s, 3H), 2.43-2.36 (m, 1H), 2.13-2.08 (m, 1H), 1.64-1.56 (m, 4H), 1.50-1.46 (m, 1H), 1.43-1.37 (m, 1H). MS (ESI) m/z: 465 [M + H]$^+$. |
| IF-6 | 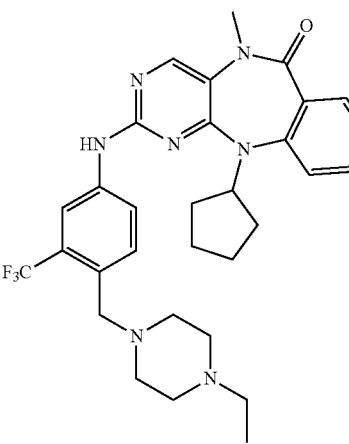 | $^1$H NMR (600 MHz, DMSO-d$_6$) δ 9.96 (s, 1H), 8.49 (s, 1H), 8.37 (s, 1H), 7.84 (d, J = 8.5 Hz, 1H), 7.61 (d, J = 8.6 Hz, 1H), 7.57 (dd, J = 7.7, 1.6 Hz, 1H), 7.49-7.44 (m, 1H), 7.27 (d, J = 8.2 Hz, 1H), 7.16 (t, J = 7.5 Hz, 1H), 4.73-4.67 (m, 1H), 3.53 (s, 2H), 3.44 (s, 3H), 2.46-2.30 (m, 8H), 1.66-1.55 (m, 4H), 1.53-1.44 (m, 1H), 1.43-1.38 (m, 1H), 1.35-1.28 (m, 1H), 1.22 (s, 1H), 0.98 (t, J = 7.2 Hz, 3H). MS (ESI) m/z: 580 [M + H]$^+$. |

TABLE 1-continued

Structure and characterization of compound IA-IH

| No. | Structure | Data of NMR and/or Mass Spectro. |
|---|---|---|
| IG-1 | 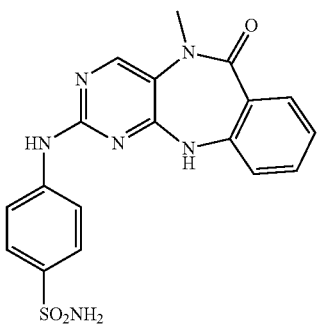 [SMILES: CN1C(=O)c2ccccc2Nc2nc(Nc3ccc(S(N)(=O)=O)cc3)ncc21]<br>HCl salt | $^1$H NMR (600 MHz, DMSO-d$_6$) δ 9.99 (s, 1H), 9.18 (s, 1H), 8.38 (s, 1H), 7.97 (s, 1H), 7.95 (s, 1H), 7.76 (dd, J = 8.0, 1.6 Hz, 1H), 7.73 (d, J = 8.6 Hz, 2H), 7.45-7.40 (m, 1H), 7.24 (d, J = 8.1 Hz, 1H), 7.07 (t, J = 7.5 Hz, 1H), 3.38 (s, 3H). $^{13}$C NMR (151 MHz, DMSO-d$_6$) δ 167.2, 161.1, 155.3, 151.5, 146.0, 143.8, 136.7, 133.4, 133.0, 127.0, 123.4, 123.0, 120.2, 119.8, 118.4, 38.4. MS (ESI) m/z: 397 [M + H]$^+$. |
| IG-2 | 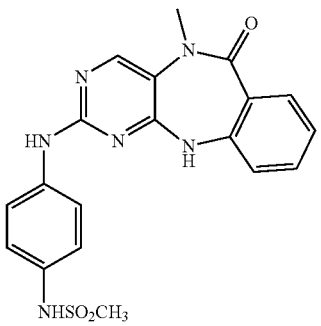<br>HCl salt | $^1$H NMR (600 MHz, DMSO-d$_6$) δ 9.44 (s, 1H), 9.41 (s, 1H), 8.85 (s, 1H), 8.31 (s, 1H), 7.78-7.72 (s, 3H), 7.41 (ddd, J = 8.6, 7.2, 1.7 Hz, 1H), 7.21 (dd, J = 8.2, 1.1 Hz, 1H), 7.15 (d, J = 8.9 Hz, 2H), 7.06-7.03 (m, 1H), 3.37 (s, 3H), 2.92 (s, 3H). $^{13}$C NMR (151 MHz, DMSO-d$_6$) δ 167.3, 160.9, 156.4, 152.8, 146.7, 137.9, 133.2, 132.9, 132.0, 123.6, 122.7, 122.3, 120.1, 120.0, 119.0, 39.2, 25.9. MS (ESI) m/z: 411 [M + H]$^+$. |
| IG-3 | 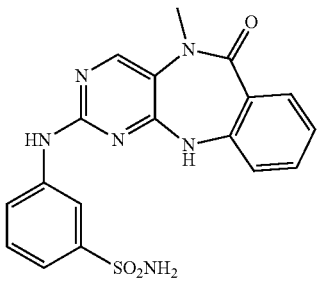 [SMILES: CN1C(=O)c2ccccc2Nc2nc(Nc3cccc(S(N)(=O)=O)c3)ncc21] | $^1$H NMR (600 MHz, DMSO-d$_6$) δ 9.78 (s, 1H), 8.89 (s, 1H), 8.38 (s, 1H), 8.25 (t, J = 2.0 Hz, 1H), 8.06 (d, J = 8.3, 2.3, 1.1 Hz, 1H), 7.76 (d, J = 7.9, 1.6 Hz, 1H), 7.47 (t, J = 8.0 Hz, 1H), 7.45-7.38 (m, 2H), 7.37 (s, 2H), 7.20 (d, J = 8.2, 1.1 Hz, 1H), 7.06 (t, 1H), 3.39 (s, 3H). $^{13}$C NMR (151 MHz, DMSO-d$_6$) δ 167.2, 160.9, 156.2, 152.7, 146.5, 144.9, 141.4, 133.3, 133.0, 129.6, 123.6, 122.8, 121.9, 120.1, 119.8, 118.6, 118.8, 38.3. MS (ESI) m/z: 397 [M + H]$^+$. |
| IH-1 | 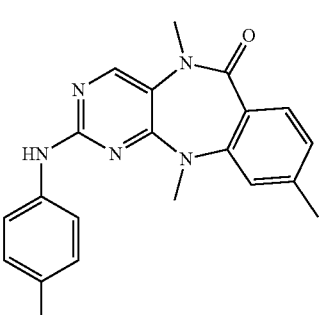 | $^1$H NMR (600 MHz, DMSO-d$_6$) δ 10.13 (s, 1H), 8.43 (s, 1H), 7.96 (d, J = 8.9 Hz, 2H), 7.79 (d, J = 8.9 Hz, 2H), 7.55 (d, J = 7.9 Hz, 1H), 7.05 (s, 1H), 6.96 (d, J = 7.9 Hz, 1H), 3.37 (s, 3H), 3.35 (s, 3H), 3.12 (s, 3H), 2.29 (s, 3H). $^{13}$C NMR (151 MHz, DMSO-d$_6$) δ 167.5, 163.3, 155.6, 152.5, 149.5, 145.6, 143.4, 132.8, 132.2, 128.4, 124.7, 123.8, 122.2, 118.7, 118.4, 44.5, 37.8, 36.2, 21.5. MS (ESI) m/z: 424 [M + H]$^+$. |

TABLE 1-continued

Structure and characterization of compound IA-IH

| No. | Structure | Data of NMR and/or Mass Spectro. |
|---|---|---|
| IH-2 | 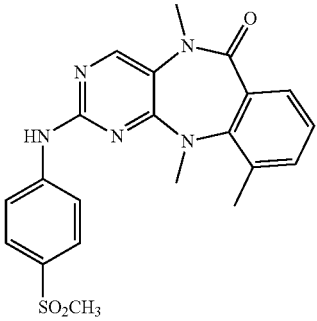 [SMILES: Cc1cccc2c1N(C)c1nc(Nc3ccc(S(N)(=O)=O)cc3)ncc1N(C)C2=O]<br>TFA salt | $^1$H NMR (600 MHz, DMSO-d$_6$) δ 10.15 (s, 1H), 8.44 (d, J = 1.0 Hz, 1H), 7.98 (d, J = 8.6 Hz, 2H), 7.79 (d, J = 8.6 Hz, 2H), 7.40 (d, J = 7.6 Hz, 1H), 7.30 (d, J = 7.1 Hz, 1H), 7.12 (t, J = 7.5 Hz, 1H), 3.47 (s, 3H), 3.39 (s, 3H), 3.12 (s, 3H), 2.35 (s, 3H). $^{13}$C NMR (151 MHz, DMSO-d$_6$) δ 168.0, 163.4, 155.7, 152.4, 146.7, 145.7, 135.9, 133.4, 132.6, 131.0, 328.9, 128.5, 125.8, 123.5, 118.1, 44.5, 38.4, 38.1, 20.7. MS (ESI) m/z: 424 [M + H]$^+$. |
| IH-3 | 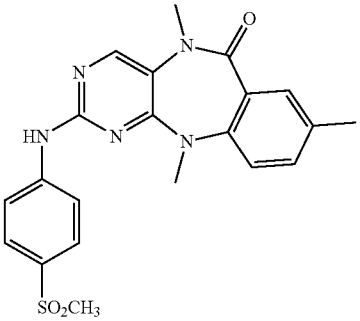 [SMILES: Cc1ccc2c(c1)C(=O)N(C)c1cnc(Nc3ccc(S(N)(=O)=O)cc3)nc1N2C]<br>TFA salt | $^1$H NMR (600 MHz, DMSO-d$_6$) δ 10.18 (s, 1H), 8.46 (s, 1H), 7.99 (d, J = 8.9 Hz, 2H), 7.82 (d, J = 8.9 Hz, 2H), 7.49 (s, 1H), 7.32 (d, J = 10.7 Hz, 1H), 7.16 (d, J = 8.4 Hz, 1H), 3.40 (s, 3H), 3.36 (s, 3H), 3.15 (s, 3H), 2.27 (s, 3H). $^{13}$C NMR (151 MHz, DMSO-d$_6$) δ 167.5, 163.5, 155.6, 152.6, 147.2, 145.6, 133.6, 133.3, 132.7, 132.2, 128.5, 126.3, 122.1, 318.3, 44.5, 38.0, 36.2, 20.4. MS (ESI) m/z: 424 [M + H]$^+$. |
| IH-4 | 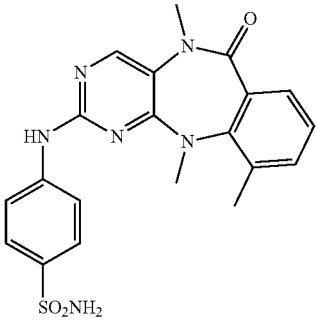<br>TFA salt | $^1$H NMR (600 MHz, DMSO-d$_6$) δ 10.06 (s, 1H), 8.45 (s, 1H), 7.92 (d, J = 8.9 Hz, 2H), 7.74 (d, J = 8.8 Hz, 2H), 7.44 (d, J = 9.3 Hz, 1H), 7.33 (d, J = 6.5 Hz, 1H), 7.16 (s, 1H), 7.15 (s, 1H), 7.14 (d, J = 5.3 Hz, 1H), 3.49 (s, 3H), 3.42 (s, 3H), 2.38 (s, 3H). $^{13}$C NMR (151 MHz, DMSO-d$_6$) δ 168.0, 163.5, 155.8, 152.3, 146.7, 144.1, 136.5, 135.9, 133.4, 131.0, 128.9, 127.0, 125.7, 123.2, 118.0, 38.4, 38.1, 20.6. MS (ESI) m/z: 425 [M + H]$^+$. |
| IH-5 | 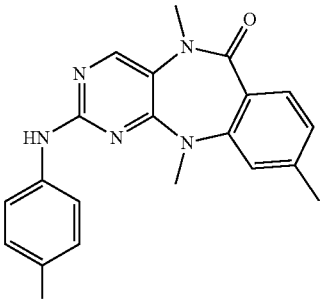<br>TFA salt | $^1$H NMR (600 MHz, DMSO-d$_6$) δ 10.03 (s, 1H), 8.44 (s, 1H), 7.90 (d, J = 8.9 Hz, 2H), 7.74 (d, J = 8.9 Hz, 2H), 7.58 (d, J = 7.9 Hz, 1H), 7.18 (s, 2H), 7.09 (s, 1H), 6.99 (d, J = 8.6 Hz, 1H), 3.39 (s, 3H), 3.38 (s, 3H), 2.33 (s, 3H). $^{13}$C NMR (151 MHz, DMSO-d$_6$) δ 167.5, 163.3, 155.8, 152.6, 149.5, 144.0, 143.4, 136.6, 132.1, 127.0, 124.8, 123.8, 121.9, 118.7, 118.2, 37.8, 36.2, 21.5. MS (ESI) m/z: 425 [M + H]$^+$. |

TABLE 1-continued

Structure and characterization of compound IA-IH

| No. | Structure | Data of NMR and/or Mass Spectro. |
|---|---|---|
| IH-6 | (structure shown) HCl salt | $^1$H NMR (600 MHz, DMSO-$d_6$) δ 10.10 (s, 1H), 8.44 (s, 1H), 7.89 (d, J = 8.9 Hz, 2H), 7.74 (d, J = 8.9 Hz, 2H), 7.48 (d, J = 1.4 Hz, 1H), 7.32 (d, J = 9.0 Hz, 1H), 7.16 (d, J = 8.4 Hz, 1H), 3.40 (s, 3H), 3.35 (s, 3H), 2.26 (s, 3H). $^{13}$C NMR (151 MHz, DMSO-$d_6$) δ 167.5, 163.6, 155.4, 152.0, 147.1, 143.8, 136.8, 133.6, 133.3, 132.2, 127.0, 126.3, 121.7, 118.3, 118.3, 38.0, 36.2, 20.4. MS (ESI) m/z: 425 [M + H]$^+$. |
| IH-7 | (structure shown) HCl salt | $^1$H NMR (600 MHz, DMSO-$d_6$) δ 10.06 (s, 1H), 8.49 (s, 1H), 7.90 (d, J = 8.9 Hz, 2H), 7.75 (d, J = 8.9 Hz, 2H), 7.17 (s, 3H), 3.41 (s, 3H), 3.38 (s, 3H). MS (ESI) m/z: 429 [M + H]$^+$. |
| IH-8 | (structure shown) | $^1$H NMR (600 MHz, DMSO-$d_6$) δ 10.21 (s, 1H), 8.51 (s, 1H), 8.00 (d, J = 8.8 Hz, 2H), 7.83 (d, J = 8.8 Hz, 2H), 7.77 (t, J = 8.7, 6.9 Hz, 1H), 7.15 (dd, J = 11.2, 2.4 Hz, 1H), 7.03 (t, J = 8.2, 2.4 Hz, 1H), 3.41 (s, 3H), 3.38 (s, 3H), 3.16 (s, 3H). MS (ESI) m/z: 428 [M + H]$^+$. |
| IH-9 | (structure shown) | $^1$H NMR (600 MHz, DMSO-$d_6$) δ 10.24 (s, 1H), 8.52 (s, 1H), 8.00 (d, J = 8.9 Hz, 2H), 7.84 (d, J = 8.9 Hz, 2H), 7.66 (d, J = 2.7 Hz, 1H), 7.58 (dd, J = 8.9, 2.7 Hz, 1H), 7.31 (d, J = 8.9 Hz, 1H), 3.43 (s, 3H), 3.39 (s, 3H), 3.16 (s, 3H). $^{13}$C NMR (151 MHz, DMSO-$d_6$) δ 166.2, 162.9, 155.7, 153.1, 148.5, 145.5, 132.9, 132.6, 131.3, 128.5, 128.1, 128.1, 121.7, 120.5, 118.4, 44.5, 38.0, 36.3. MS (ESI) m/z: 444 [M + H]$^+$. |

TABLE 1-continued

Structure and characterization of compound IA-IH

| No. | Structure | Data of NMR and/or Mass Spectro. |
|---|---|---|
| IH-10 | (structure shown; HCl salt) | $^1$H NMR (600 MHz, DMSO-$d_6$) δ 10.12 (s, 1H), 8.50 (s, 1H), 7.90 (d, J = 8.9 Hz, 2H), 7.75 (d, J = 8.9 Hz, 2H), 7.65 (d, J = 2.7 Hz, 1H), 7.57 (dd, J = 8.9, 2.7 Hz, 1H), 7.32 (d, J = 9.0 Hz, 1H), 3.42 (s, 3H), 3.38 (s, 3H). $^{13}$C NMR (151 MHz, DMSO-$d_6$) δ 166.2, 163.0, 155.8, 153.0, 148.5, 143.8, 136.8, 132.6, 131.3, 128.1, 128.1, 127.0, 121.4, 120.6, 118.3, 38.0, 36.3. MS (ESI) m/s: 445 [M + H]$^+$. |
| IH-11 | (structure shown; HCl salt) | $^1$H NMR (600 MHz, DMSO-$d_6$) δ 10.14 (s, 1H), 8.50 (s, 1H), 7.91 (d, J = 8.9 Hz, 2H), 7.75 (d, J = 8.9 Hz, 2H), 7.48 (dd, J = 7.7, 1.5 Hz, 1H), 7.41 (ddd, J = 13.2, 8.1, 1.6 Hz, 1H), 7.25 (td, J = 8.0, 4.6 Hz, 1H), 3.52 (d, J = 7.2 Hz, 3H), 3.43 (s, 3H). $^{13}$C NMR (151 MHz, DMSO-$d_6$) δ 166.6 (d, J = 3.3 Hz), 163.4, 155.7, 154.5, 152.8, 143.8, 136.8, 135.8, 131.0, 127.4, 127.0, 126.2 (d, J = 8.7 Hz), 122.1, 120.5 (d, J = 21.5 Hz), 118.2, 38.3, 38.0 (d, J = 12.3 Hz). MS (ESI) m/z: 429 [M + H]$^+$. |
| IH-12 | (structure shown; HCl salt) | $^1$H NMR (600 MHz, DMSO-$d_6$) δ 10.27 (s, 1H), 8.52 (s, 1H), 8.01 (d, J = 8.9 Hz, 2H), 7.84 (d, J = 8.9 Hz, 2H), 7.49 (dd, J = 7.7, 1.5 Hz, 1H), 7.42 (ddd, J = 13.2, 8.1, 1.6 Hz, 1H), 7.28-7.22 (m, 1H), 3.53 (d, J = 7.2 Hz, 3H), 3.43 (s, 3H), 3.16 (s, 3H). $^{13}$C NMR (151 MHz, DMSO-$d_6$) δ 166.6 (d, J = 3.4 Hz), 163.3, 155.6, 152.9, 145.5, 132.9, 131.0, 128.5, 127.4, 126.2 (d, J = 8.5 Hz), 122.4, 120.6, 120.5, 118.3, 44.5, 38.3, 38.0 (d, J = 12.3 Hz). MS (ESI) m/z: 428 [M + H]$^+$. |
| IH-13 | (structure shown; HCl salt) | $^1$H NMR (600 MHz, DMSO-$d_6$) δ 10.12 (s, 1H), 8.50 (s, 1H), 7.91 (d, J = 8.9 Hz, 2H), 7.75 (d, J = 8.9 Hz, 2H), 7.71 (d, J = 8.4 Hz, 1H), 7.35 (d, J = 1.9 Hz, 1H), 7.25 (dd, J = 8.4, 1.9 Hz, 1H), 3.41 (s, 3H), 3.40 (s, 3H). $^{13}$C NMR (151 MHz, DMSO-$d_6$) δ 166.6, 162.7, 155.8, 152.9, 150.7, 143.8, 137.8, 136.7, 133.9, 127.0, 125.3, 124.1, 121.5, 118.5, 118.3, 37.9, 36.3. MS (ESI) m/z. 445 [M + H]$^+$. |

TABLE 1-continued
Structure and characterization of compound IA-IH
| No. | Structure | Data of NMR and/or Mass Spectro. |
|---|---|---|
| IH-14 | 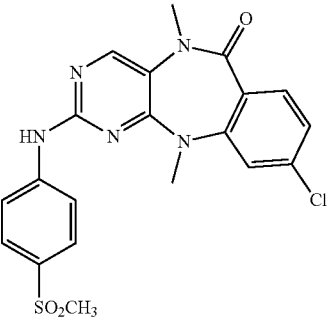 [SMILES: CN1C(=O)c2ccc(Cl)cc2N(C)c2nc(Nc3ccc(S(N)(=O)=O)cc3)ncc21]<br>HCl salt | $^1$H NMR (600 MHz, DMSO-$d_6$) δ 10.26 (s, 1H), 8.52 (s, 1H), 8.00 (d, J = 8.9 Hz, 2H), 7.84 (d, J = 8.9 Hz, 2H), 7.71 (d, J = 8.4 Hz, 1H), 7.53 (d, J = 8.8 Hz, 1H), 7.34 (d, J = 2.0 Hz, 1H), 3.42 (s, 3H), 3.16 (s, 3H), 3.04 (s, 3H). $^{13}$C NMR (151 MHz, DMSO-$d_6$) δ 162.7, 155.7, 153.0, 150.7, 145.5, 137.8, 133.9, 132.9, 129.3, 128.5, 125.3, 124.1, 121.9, 118.4, 113.8, 44.9, 37.9, 36.3. MS (ESI) m/z: 444 $[M + H]^+$. |
Compound II of the Formula
Synthesis of Compounds of General Formula II
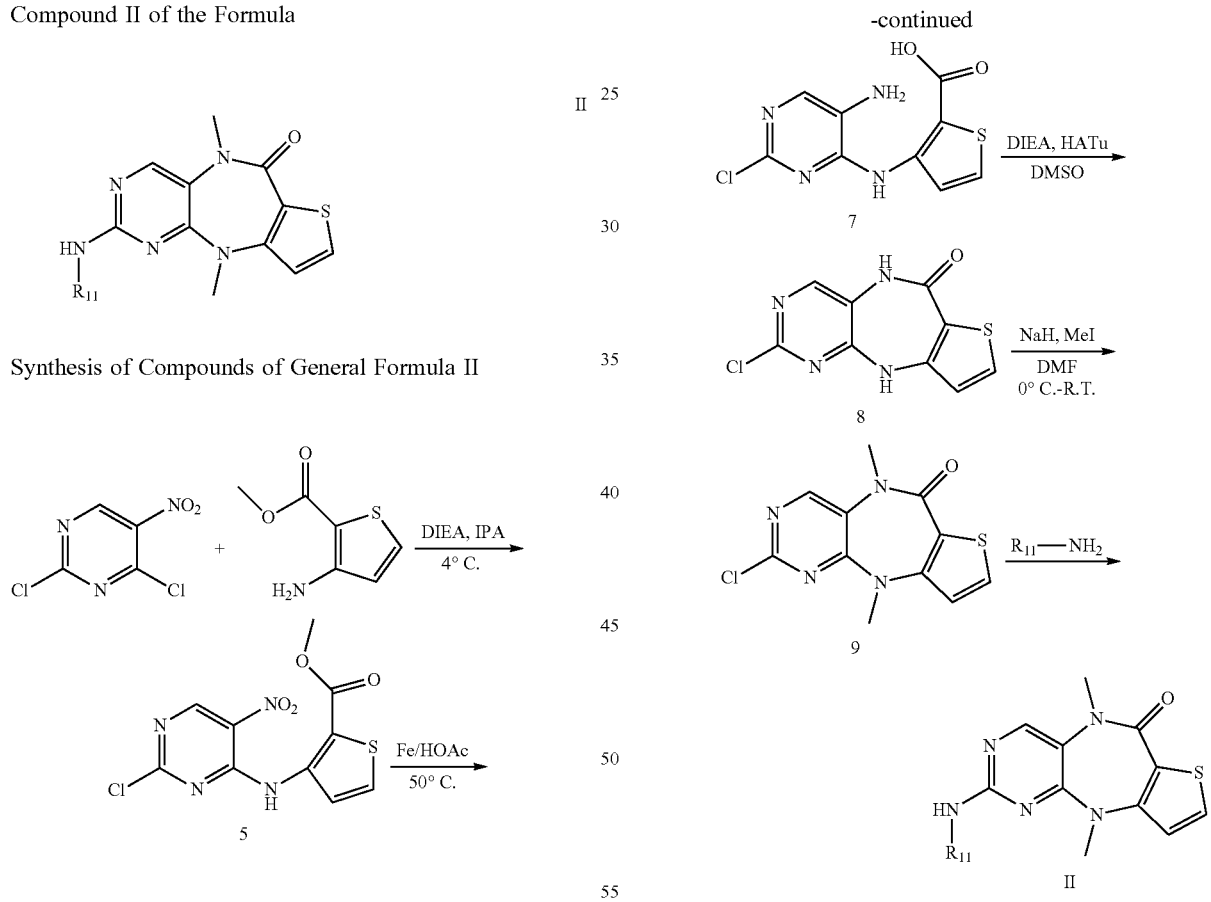
Preparation of Compound 5
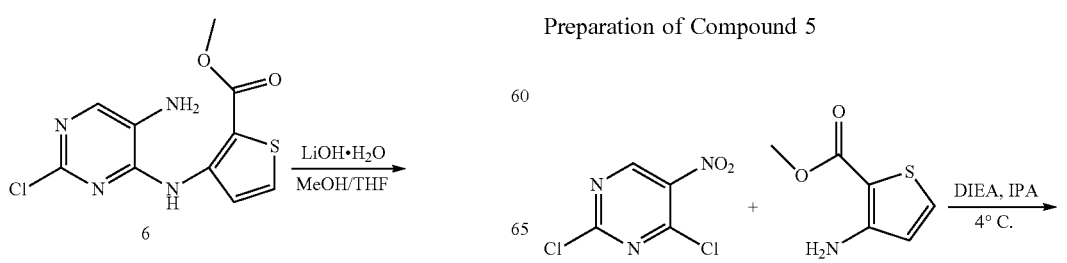

Preparation of Compound 7

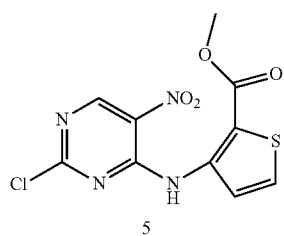

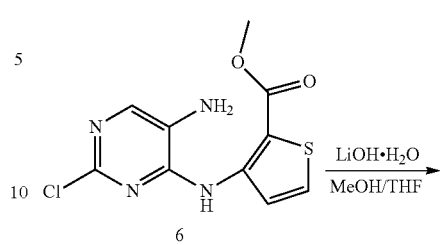

A solution of 3-amino-2-thiophene carboxylate (361 mg, 2.3 mmol), N, N-diisopropylethylamine (0.76 mL, 4.6 mmol) was dissolved in 15 mL of isopropanol and left under stirring for 4° C. 5 min, then to the system were dissolved in 5 mL of isopropanol was added dropwise 2,4-dichloro-5-nitro-pyrimidine (582 mg, 3 mmol), and finally stirring was continued for 1 h after the reaction was stopped. System concentrated silica gel column chromatography, eluted directly to give compound 5 (pale yellow solid, 673 mg, 93% yield) with dichloromethane.

1H NMR (600 MHz, CDCl3) δ9.24 (s, 1H), 8.56 (dd, J=8.5, 1.0 Hz, 1H), 8.14 (dd, J=8.0, 1.5 Hz, 1H), 7.68 (ddd, J=8.7, 7.5, 1.5 Hz, 1H), 4.02 (s, 3H). 13C NMR (150 MHz, CDCl3) δ167.4, 163.6, 157.6, 153.1, 137.9, 133.7, 131.4, 125.1, 123.5, 52.8. MS (ESI) m/z: 315 [m+H]+.

Preparation of Compound 6

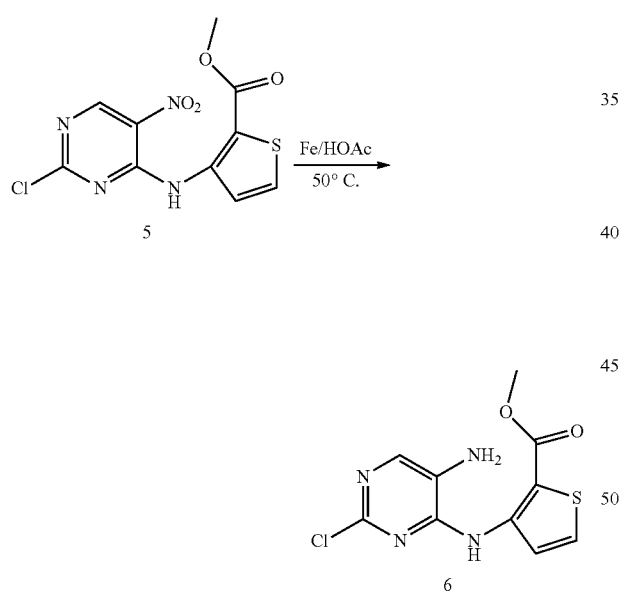

Compound 5 (673 mg, 2.14 mmol) and iron powder (1.2 g, 21.4 mmol) was dissolved in 30 mL of acetic acid and placed in a stirred reactor preheated to 50 deg. C. in an oil bath at 9 h, LC-MS and TLC indicated the reaction was complete. Remove most of the iron powder is then screwed off acetic acid, and then the system was poured into ice-water, and the precipitated solid was Buchner funnel and the filter cake was washed with ice-water multiple times, and finally the solid was collected to give Compound 6 (548 mg, 90% yield) directly for the next step.

MS (ESI) m/z: 285 [M+H]+.

Compound 6 (548 mg, 1.9 mmol) was dissolved in methanol/tetrahydrofuran (5 mL/5 mL) mixture solution is added a lithium hydroxide monohydrate (798 mg, 19.0 mmol), stirred at room temperature for 2 h, LC-MS the reaction was complete after the reaction was stopped. To a solution of 6N system environment in an ice-water bath until a solution of hydrochloric acid system pH=5, a large amount of solid precipitated, was filtered using Buchner funnel, the filter cake was washed several times with ice water, the filter cake was collected to give compound 7 (488 mg, yield 95%), was used directly in the next step.

MS (ESI) m/z: 271 [M+H]+.

Preparation of Compound 8

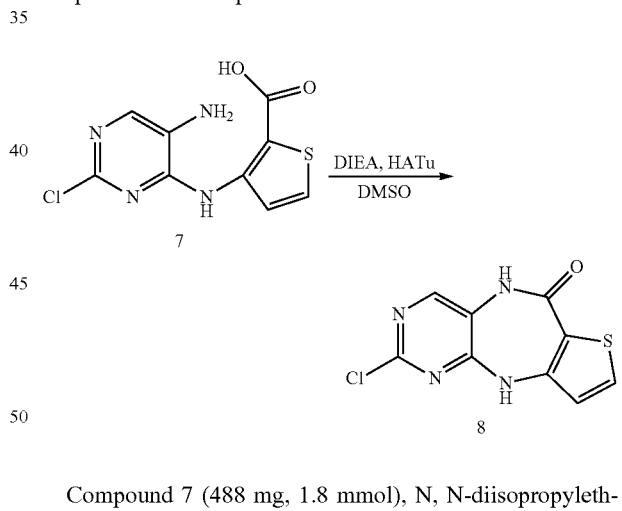

Compound 7 (488 mg, 1.8 mmol), N, N-diisopropylethylamine (0.89 mL, 5.4 mmol) and 2-(7-azo-benzotriazole)-N, N, N', N'-tetramethyluronium hexafluorophosphate (1030 mg, 2.7 mmol) was dissolved in 10 mL dimethylsulfoxide and stirred overnight. LC-MS the reaction was complete the reaction was stopped, the ice water was poured into the system, and the precipitated solid was filtered using Buchner funnel, the filter cake was washed several times with ice water, the filter cake was collected to give compound 8 (372 mg, 82% yield).

1H NMR (600 MHz, DMSO-d 6) δ0.25 (s, 1H), 9.50 (s, 1H), 7.77 (s, 1H), 7.69 (d, J=5.3 Hz, 1H), 6.65 (d, J=5.3 Hz, 1H) 13C NMR (151 MHz, DMSO-d 6) δ162.0, 155.3, 152.9, 148.0, 142.5, 135.0, 122.2, 122.1, 114.8. MS (ESI) m/z: 253 [m+H]$^+$.

Preparation of Compound 9

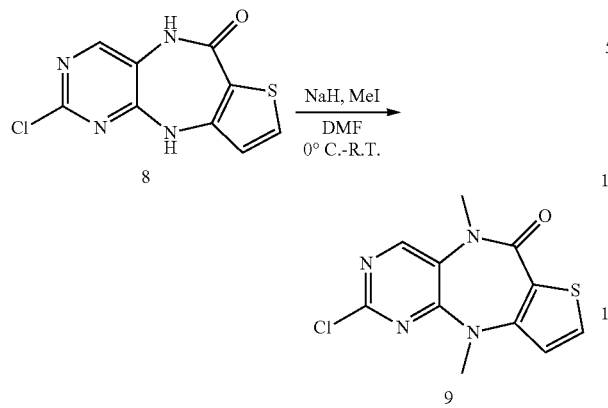

Compound 8 (372 mg, 1.5 mmol), iodomethane (0.28 mL, 4.5 mmol) was dissolved in 10 mL of dimethylformamide and left to stir at 0° C. 5 min, added to the system and then sodium hydride (180 mg of, 60 mass fraction %), the reaction was slowly raised to room temperature with stirring. LC-MS the reaction was complete the reaction was stopped, the ice water was poured into the system, and the precipitated solid was filtered using Buchner funnel and the filter cake washed several times with ice water, the filter cake was collected to give compound 9 (294 mg, 70% yield).

1H NMR (600 MHz, DMSO-d 6) δ8.47 (s, 1H), 7.94 (d, J=5.4 Hz, 1H), 7.04 (d, J=5.4 Hz, 1H), 3.38 (s, 3H), 3.31 (s, 3H) 13C NMR (151 MHz, DMSO-d 6) 6163.5, 153.8, 153.5, 149.3, 133.8, 128.2, 121.5, 119.2, 110.0, 37.4, 37.3. MS (ESI) m/z: 281 [M$^+$H]+.

Synthesis of Compounds of Formula II

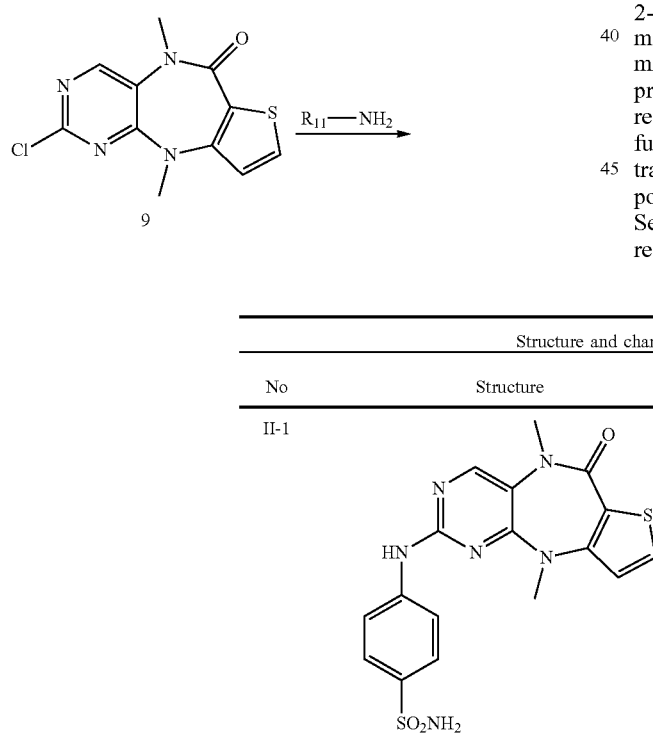

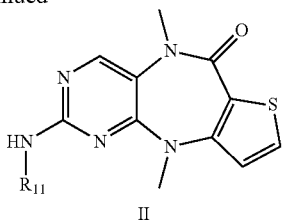

Method A:

Compound 9 (28 mg, 0.1 mmol) and aromatic amines (0.1 mmol) was dissolved in 1 mL sec-butanol, was added a 4N HCl solution (50 μL, 0.2 mmol), and finally placed in a closed system has been preheated to 110 deg.] C. oil bath heated with stirring until the reaction was complete (LC-MS and TLC monitoring). The reaction was stopped, the reaction solution was transferred to a centrifuge tube 2 mL of adding a certain amount of petroleum ether, shaking, centrifugation, supernatant liquid was discarded, a small amount of methanol was added, along with petroleum ether, the above operation is repeated until the supernatant liquid became clear until the solid was collected, rotary evaporation to dry and be weighted to get compound II.

Method B:

Compound 9 (28 mg, 0.1 mmol) and aromatic amines (0.1 mmol) was dissolved in 1 mL sec-butanol, was added a 4N HCl solution (50 μL, 0.2 mmol), and finally placed in a closed system has been preheated to 110 deg.] C. oil bath heated with stirring until the reaction was complete (LC-MS and TLC monitoring). The reaction was stopped, concentrated and purified by reverse phase preparative HPLC (containing 0.35% aqueous trifluoroacetic acid and methanol as mobile phase), dried and concentrated in vacuo to produce compound II.

Method C:

Compound 9 (28 mg, 0.1 mmol), aromatic amines (0.1 mmol) was dissolved in 1 ml tert-butanol, was added tris (dibenzylideneacetone) dipalladium (5.5 mg, 0.006 mmol), 2-dicyclohexyl phosphate 2,4,6-triisopropyl-biphenyl (4.3 mg, 0.009 mmol) and potassium carbonate (55.3 mg, 0.4 mmol), drainage systems nitrogen and placed in an oil bath preheated to 100° C. heated with stirring after 5 h the reaction was stopped. System filtered through a fritted funnel off the solid, the liquid was collected and concentrated by silica gel column chromatography to obtain compound II.

Series III derivatives compounds II may be synthesized with reference series.

TABLE 2

Structure and characterization of compounds II and III

| No | Structure | Data of NMR and Mass Spectro. |
|---|---|---|
| II-1 | 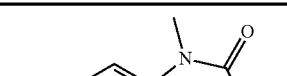 | $^1$H NMR (600 MHz, DMSO-d$_6$) δ 10.03 (s, 1H), 8.37 (s, 1H), 7.89 (dd, J = 9.1, 7.0 Hz, 3H), 7.74 (d, J = 8.6 Hz, 2H), 7.18 (s, 2H), 7.03 (d, J = 5.4 Hz, 1H), 3.42 (s, 3H), 3.30 (s, 3H). $^{13}$C NMR (151 MHz, DMSO-d$_6$) δ 164.0, 162.7, 155.1, 151.9, 150.0, 143.7, 136.8, 133.0, 127.0, 121.3, 121.2, 119.2, 118.4, 37.3, 37.2. MS (ESI) m/z: 417 [M + H]$^+$. |

TABLE 2-continued

Structure and characterization of compounds II and III

| No | Structure | Data of NMR and Mass Spectro. |
|---|---|---|

II-2 TFA salt 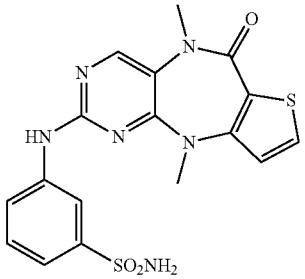 [SMILES: CN1C(=O)c2sccc2N(C)c2nc(Nc3cccc(S(N)(=O)=O)c3)ncc21]

$^1$H NMR (600 MHz, DMSO) δ 9.95 (s, 1H), 8.52 (s, 1H), 8.34 (s, 1H), 7.85 (d, J = 5.4 Hz, 1H), 7.73 (d, J = 8.3 Hz, 1H), 7.46 (t, J = 7.9 Hz, 1H), 7.40 (d, J = 7.8 Hz, 1H), 7.28 (s, 2H), 6.99 (d, J = 5.4 Hz, 1H), 3.42 (s, 3H), 3.29 (s, 3H). MS (ESI) m/z: 417 [M + H]$^+$.

II-3 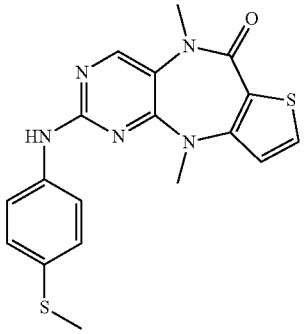 [SMILES: CSc1ccc(Nc2ncc3c(n2)N(C)c2ccsc2C(=O)N3C)cc1]

$^1$H NMR (600 MHz, DMSO-d$_6$) δ 9.62 (s, 1H), 8.30 (s, 1H), 7.85 (d, J = 5.4 Hz, 1H), 7.71 (d, J = 8.7 Hz, 2H), 7.24 (d, J = 8.8 Hz, 2H), 7.01 (d, J = 5.4 Hz, 1H), 3.39 (s, 3H), 3.29 (s, 3H), 2.45 (s, 3H). $^{13}$C NMR (151 MHz, DMSO-d$_6$) δ 164.1, 162.5, 156.1, 152.9, 150.5, 138.7, 132.9, 129.8, 128.1, 121.0, 120.5, 119.8, 119.0, 37.2, 37.1, 16.6. MS (ESI) m/z: 384 [M + H]$^+$.

II-4 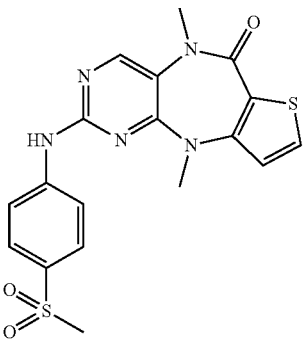 [SMILES: CN1C(=O)c2sccc2N(C)c2nc(Nc3ccc(S(C)(=O)=O)cc3)ncc21]

$^1$H NMR (600 MHz, DMSO) δ 10.19 (s, 1H), 8.38 (s, 1H), 7.98 (d, J = 8.9 Hz, 2H), 7.87 (d, J = 5.4 Hz, 1H), 7.82 (d, J = 8.9 Hz, 2H), 7.02 (d, J = 5.4 Hz, 1H), 3.42 (s, 3H), 3.29 (s, 3H), 3.15 (s, 3H). MS (ESI) m/z: 418 [M + H]$^+$.

II-5 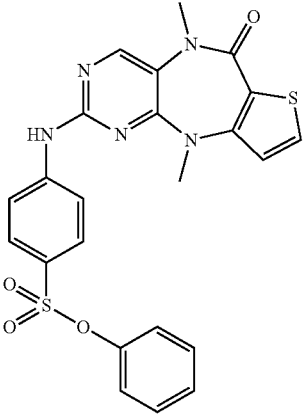 [SMILES: CN1C(=O)c2sccc2N(C)c2nc(Nc3ccc(S(=O)(=O)Oc4ccccc4)cc3)ncc21]

$^1$H NMR (600 MHz, CDCl$_3$) δ 8.10 (s, 1H), 7.75 (s, 4H), 7.49 (d, J = 5.4 Hz, 1H), 7.28 (t, J = 7.6 Hz, 2H), 7.23 (t, J = 7.3 Hz, 1H), 7.00 (d, J = 7.8 Hz, 2H), 6.77 (d, J = 5.4 Hz, 1H), 3.43 (s, 3H), 3.39 (s, 3H). MS (ESI) m/z: 494 [M + H]$^+$.

TABLE 2-continued

Structure and characterization of compounds II and III

| No | Structure | Data of NMR and Mass Spectro. |
|---|---|---|
| II-6 | 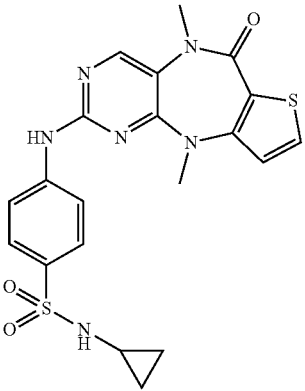 [SMILES: CN1C(=O)c2sccc2N(C)c2nc(Nc3ccc(S(=O)(=O)NC4CC4)cc3)ncc21] | $^1$H NMR (600 MHz, DMSO-d$_6$) δ 10.14 (s, 1H), 8.37 (s, 1H), 7.94 (dd, 8.9, 2.2 Hz, 2H), 7.87 (d, J = 5.4 Hz, 1H), 7.72 (d, J = 8.8 Hz, 2H), 7.02 (d, J = 5.4 Hz, 1H), 3.42 (s, 3H), 3.29 (s, 3H), 2.08 (s, 1H), 0.49-0.44 (m, 2H), 0.41-0.33 (m, 2H). MS (ESI) 457 [M + H]$^+$. |
| II-7 | 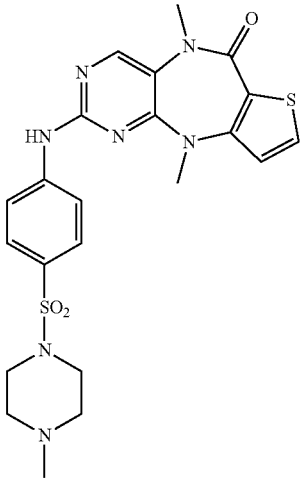 | $^1$H NMR (600 MHz, DMSO-d$_6$) δ 10.15 (s, 1H), 8.37 (s, 1H), 8.00 (d, J = 8.9 Hz, 2H), 7.86 (d, J = 5.4 Hz, 1H), 7.64 (d, J = 8.9 Hz, 2H), 7.01 (d, J = 5.4 Hz, 1H), 3.43 (s, 3H), 3.30 (s, 3H), 2.87 (s, 4H), 2.36 (t, J = 5.0 Hz, 4H), 2.14 (s, 3H). $^{13}$C NMR (151 MHz, DMSO-d$_6$) δ 164.0, 162.5, 155.5, 152.8, 150.3, 145.4, 133.0, 129.2, 126.4, 121.6, 121.1, 119.0, 118.2, 54.0, 46.2, 45.7, 37.3, 37.2. MS (ESI) m/z: 500 [M + H]$^+$. |
| II-8 | 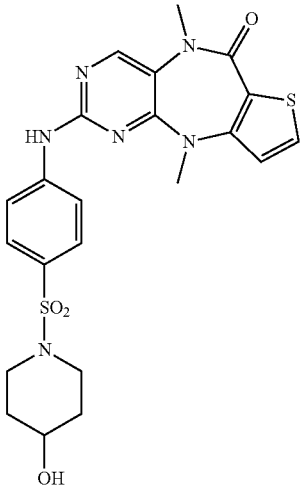 [SMILES: CN1C(=O)c2sccc2N(C)c2nc(Nc3ccc(S(=O)(=O)N4CCC(O)CC4)cc3)ncc21] | $^1$H NMR (600 MHz, DMSO-d$_6$) δ 10.14 (s, 1H), 8.38 (s, 1H), 7.99 (d, J = 2.0 Hz, 1H), 7.98 (d, J = 2.0 Hz, 1H), 7.87 (s, 1H), 7.86 (s, 1H), 7.65 (d, J = 2.0 Hz, 1H), 7.64 (d, J = 1.9 Hz, 1H), 7.02 (d, J = 5.4 Hz, 1H), 3.52 (tt, J = 7.6, 3.7 Hz, 1H), 3.43 (s, 3H), 3.30 (s, 3H), 3.17-3.11 (m, 2H), 2.74-2.66 (m, 2H), 1.78-1.71 (m, 2H), 1.48-1.39 (m, 2H). $^{13}$C NMR (151 MHz, DMSO-d$_6$) δ 164.0, 162.5, 155.5, 152.7, 150.3, 145.1, 133.0, 129.0, 127.3, 121.6, 121.1, 119.0, 118.2, 56.5, 43.7, 37.3, 37.2, 33.4. MS (ESI) m/z: 501 [M + H]$^+$. |

TFA salt

TABLE 2-continued

Structure and characterization of compounds II and III

| No | Structure | Data of NMR and Mass Spectro. |
|---|---|---|
| II-9 | (structure with NHSO₂CH₃ group) | $^1$H NMR (600 MHz, DMSO-$d_6$) δ 9.58 (s, 1H), 9.43 (s, 1H), 8.29 (s, 1H), 7.84 (d, J = 5.3 Hz, 1H), 7.69 (s, 1H), 7.68 (s, 1H), 7.15 (d, J = 2.3 Hz, 1H), 7.14 (d, J = 2.2 Hz, 1H), 7.01 (d, J = 5.4 Hz, 1H), 3.38 (s, 3H), 3.28 (s, 3H), 2.92 (s, 3H). $^{13}$C NMR (151 MHz, DMSO-$d_6$) δ 164.3, 162.6, 156.1, 152.8, 150.6, 137.8, 132.9, 132.0, 122.5, 121.0, 120.5, 120.0, 118.8, 37.2, 37.1, 25.8. MS (ESI) m/z: 431 [M + H]$^+$. |
| II-10 | (structure with COOH group) HCl salt | $^1$H NMR (600 MHz, DMSO-$d_6$) δ 10.04 (s, 1H), 8.36 (s, 1H), 7.89-7.83 (m, 5H), 7.03 (d, J = 5.3 Hz, 1H), 3.42 (s, 3H), 3.29 (s, 3H). $^{13}$C NMR (151 MHz, DMSO-$d_6$) δ 167.6, 164.0, 162.5, 155.5, 152.4, 150.2, 145.0, 133.0, 130.8, 123.5, 121.3, 121.1, 119.0, 118.1, 39.5, 37.2 (d, J = 3.6 Hz). MS (ESI) m/z: 382 [M + H]$^+$. |
| II-11 | (structure with NO₂ group) HCl salt | $^1$H NMR (600 MHz, DMSO-$d_6$) δ 10.41 (s, 1H), 8.41 (s, 1H), 8.21 (d, J = 8.4 Hz, 2H), 7.99 (d, J = 8.5 Hz, 2H), 7.88 (d, J = 5.3 Hz, 1H), 7.03 (d, J = 5.4 Hz, 1H), 3.44 (s, 3H), 3.30 (s, 3H). $^{13}$C NMR (151 MHz, DMSO-$d_6$) δ 164.0, 162.4, 155.2, 152.8, 150.2, 147.5, 140.8, 133.1, 125.5, 122.2, 121.1, 119.1, 118.0, 37.3, 37.2. MS (ESI) m/z: 383 [M + H]$^+$. |
| II-12 | (structure with OH group) HCl salt | $^1$H NMR (600 MHz, DMSO-$d_6$) δ 9.89 (s, 1H), 8.21 (s, 1H), 7.89 (d, J = 5.4 Hz, 1H), 7.39 (d, J = 8.9 Hz, 2H), 7.05 (d, J = 5.4 Hz, 1H), 6.79-6.74 (m, 2H), 3.38 (s, 3H), 3.27 (s, 3H). $^{13}$C NMR (151 MHz, DMSO-$d_6$) δ 163.9, 163.6 (d, J = 3.8 Hz), 154.2, 148.5, 133.1, 130.3, 122.9, 121.6, 121.5, 119.7, 119.6, 119.5, 115.7, 37.6 (d, J = 2.9 Hz), 37.5 (d, J = 3.9 Hz). MS (ESI) m/z: 354 [M + H]$^+$. |

TABLE 2-continued

Structure and characterization of compounds II and III

| No | Structure | Data of NMR and Mass Spectro. |
|---|---|---|
| II-13 | HCl salt | $^1$H NMR (600 MHz, DMSO-d$_6$) δ 10.03 (s, 1H), 8.36 (s, 1H), 7.89-7.82 (m, 4H), 7.79 (d, J = 8.8 Hz, 2H), 7.17 (s, 1H), 7.04 (d, J = 5.4 Hz, 1H), 3.42 (s, 3H), 3.29 (s, 3H). $^{13}$C NMR (151 MHz, DMSO-d$_6$) δ 168.0, 163.9, 162.7, 155.2, 151.6, 150.0, 143.3, 133.0, 128.8, 127.5, 121.2, 121.0, 119.2, 118.1, 37.3, 37.3. MS (ESI) m/z: 381 [M + H]$^+$. |
| II-14 | TFA salt | $^1$H NMR (600 MHz, DMSO-d$_6$) δ 9.81 (s, 1H), 8.33 (s, 1H), 7.87 (d, J = 5.1 Hz, 1H), 7.83 (d, J = 9.0 Hz, 2H), 7.28 (d, J = 8.9 Hz, 2H), 7.02 (d, J = 5.4 Hz, 1H), 3.40 (s, 3H), 3.29 (s, 3H). $^{13}$C NMR (151 MHz, DMSO-d$_6$) δ 164.1, 162.5, 155.9, 152.8, 150.4, 133.0, 123.6, 121.0, 120.9, 119.9, 119.0, 40.5, 37.2 (d, J = 7.0 Hz). MS (ESI) m/z: 381 [M + H]$^+$. |
| II-15 | 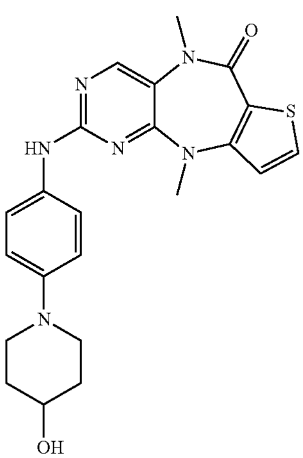 [SMILES: CN1C(=O)c2sccc2N(C)c2nc(Nc3ccc(N4CCC(O)CC4)cc3)ncc21] | $^1$H NMR (600 MHz, DMSO-d$_6$) δ 9.31 (s, 1H), 8.24 (s, 1H), 7.84 (d, J = 5.4 Hz, 1H), 7.53 (d, J = 9.0 Hz, 2H), 7.00 (d, J = 5.4 Hz, 1H), 6.88 (d, J = 8.7 Hz, 2H), 3.63-3.56 (m, 1H), 3.45-3.41 (m, 2H), 3.35 (s, 3H), 3.27 (s, 3H), 2.79-2.73 (m, 2H), 1.82 (dd, J = 12.7, 4.1 Hz, 2H), 1.53-1.45 (m, 2H). $^{13}$C NMR (151 MHz, DMSO-d$_6$) δ 164.2, 162.6, 156.6, 152.9, 150.6, 132.7, 120.9, 120.6, 119.8, 119.0, 116.7, 66.5, 47.8, 41.0, 37.1 (d, J = 18.1 Hz), 34.5. MS (ESI) m/z: 437 [M + H]$^+$. |

TABLE 2-continued

Structure and characterization of compounds II and III

| No | Structure | Data of NMR and Mass Spectro. |
|---|---|---|
| II-16 | 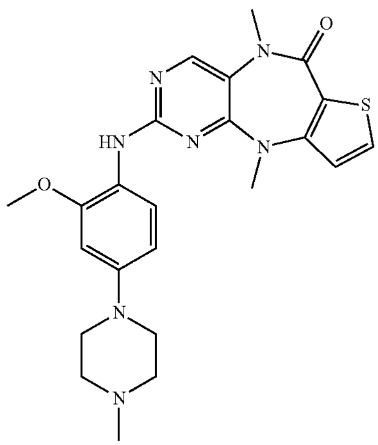 [SMILES: COc1cc(N2CCN(C)CC2)ccc1Nc1ncc2c(n1)N(C)c1ccsc1C(=O)N2C] | $^1$H NMR (600 MHz, DMSO-d$_6$) δ 8.21 (s, 1H), 7.90 (s, 1H), 7.84 (d, J = 5.4 Hz, 1H), 7.73 (d, J = 8.7 Hz, 1H), 6.99 (d, J = 5.4 Hz, 1H), 6.63 (d, J = 2.6 Hz, 1H), 6.49 (dd, J = 8.8, 2.6 Hz, 1H), 3.81 (s, 3H), 3.30 (s, 3H), 3.26 (s, 3H), 3.12 (t, J = 5.0 Hz, 4H), 2.47 (t, J = 5.0 Hz, 4H), 2.24 (s, 3H). $^{13}$C NMR (151 MHz, DMSO-d$_6$) δ 164.1, 162.7, 152.9, 151.2, 150.5, 148.4, 132.7, 122.6, 121.0, 120.9, 120.1, 119.0, 107.3, 100.6, 56.1, 55.2, 49.2, 46.2, 37.1, 36.9. MS (ESI) m/z: 466 [M + H]$^+$. |
| II-17 | TFA salt | $^1$H NMR (600 MHz, DMSO-d$_6$) δ 10.11 (s, 1H), 9.91 (s, 1H), 8.35 (s, 1H), 7.87 (d, J = 5.4 Hz, 1H), 7.85 (d, J = 8.7 Hz, 2H), 7.43 (d, J = 8.8 Hz, 2H), 7.03 (d, J = 5.4 Hz, 1H), 4.26 (s, 4H), 3.45 (q, J = 7.0, 6.5 Hz, 2H), 3.41 (s, 3H), 3.30 (s, 3H), 3.09 (s, 2H), 2.83 (s, 3H). $^{13}$C NMR (151 MHz, DMSO-d$_6$) δ 169.8, 164.0, 162.5, 155.9, 152.8, 150.4, 142.9, 132.9, 128.8, 127.2, 121.1, 121.0, 119.1, 118.3, 54.1, 52.8, 42.8, 40.6, 37.2 (d, J = 3.0 Hz). MS (ESI) m/z: 464 [M + H]$^+$. |
| II-18 | TFA salt | $^1$H NMR (600 MHz, DMSO-d$_6$) δ 10.19 (s, 1H), 9.58 (s, 1H), 8.29 (s, 1H), 7.85 (d, J = 5.4 Hz, 1H), 7.68 (d, J = 9.0 Hz, 2H), 7.51 (d, J = 9.1 Hz, 2H), 7.02 (d, J = 5.4 Hz, 1H), 4.23 (s, 2H), 3.39 (s, 3H), 3.28 (s, 3H). $^{13}$C NMR (151 MHz, DMSO-d$_6$) δ 164.6, 164.1, 162.6, 156.1, 152.6, 150.4, 136.9, 132.9, 132.8, 121.0, 120.4, 120.3, 119.7, 119.1, 44.0, 37.1, 37.1. MS (ESI) m/z: 429 [M + H]$^+$. |

TABLE 2-continued

Structure and characterization of compounds II and III

| No | Structure | Data of NMR and Mass Spectro. |
| --- | --- | --- |
| II-19 | 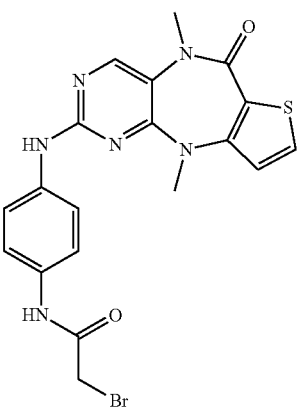<br>TFA salt | $^1$H NMR (600 MHz. DMSO-$d_6$) δ 10.29 (s, 1H), 9.61 (s, 1H), 8.29 (s, 1H), 7.86 (d, J = 5.4 Hz, 1H), 7.67 (d, J = 8.9 Hz, 2H), 7.51 (d, J = 9.0 Hz, 2H), 7.02 (d, J = 5.4 Hz, 1H), 4.02 (s, 2H), 3.38 (s, 3H), 3.28 (s, 3H). MS (ESI) m/z: 474 [M + H]$^+$. |
| II-20 | 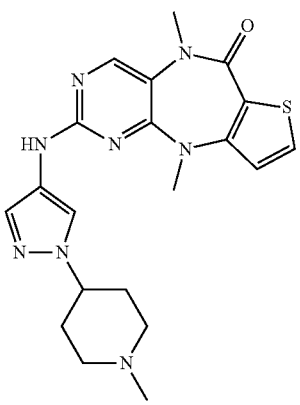 | $^1$H NMR (600 MHz, DMSO-$d_6$) δ 9.44 (s, 1H), 8.25 (s, 1H), 7.90 (s, 1H), 7.84 (d, J = 5.4 Hz, 1H), 7.51 (s, 1H), 7.03 (d, J = 5.4 Hz, 1H), 3.40 (s, 3H), 3.26 (s, 3H), 2.89-2.83 (m, 2H), 2.21 (s, 3H), 2.08-2.02 (m, 2H), 2.00-1.88 (m, 4H). $^{13}$C NMR (151 MHz, DMSO-$d_6$) δ 164.2, 162.9, 156.1, 150.7, 132.7, 130.0, 123.3, 121.0, 119.0, 58.5, 54.6, 46.2, 37.2, 32.5, 26.0. MS (ESI) m/z: 474 [M + H]$^+$. |
| II-21 | 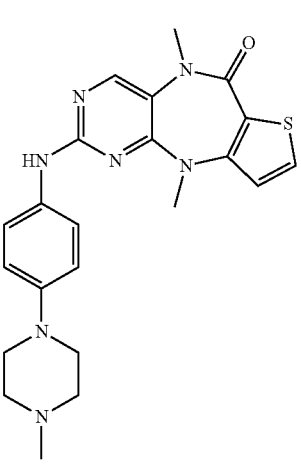 [SMILES: CN1CCN(c2ccc(Nc3ncc4c(n3)N(C)c3ccsc3C(=O)N4C)cc2)CC1] | $^1$H NMR (600 MHz, Methanol-$d_4$) δ 8.67 (s, 1H), 8.04 (s, 1H), 7.63 (d, J = 5.3 Hz, 1H), 7.53 (d, J = 8.6 Hz, 2H), 6.94 (d, J = 8.6 Hz, 2H), 6.86 (d, J = 5.3 Hz, 1H), 3.35 (s, 3H), 3.30 (s, 3H), 3.22 (t, J = 4.8 Hz, 4H), 2.89 (t, J = 5.0 Hz, 4H), 2.56 (s, 3H). $^{13}$C NMR (151 MHz, Methanol-$d_4$) δ 165.2, 162.9, 156.4, 151.6, 150.7, 146.0, 133.6, 131.9, 120.4, 119.9, 119.6, 118.4, 117.0, 54.2, 48.7, 43.8, 36.3, 35.9. MS (ESI) m/z: 436 [M + H]$^+$. |

TABLE 2-continued

Structure and characterization of compounds II and III

| No | Structure | Data of NMR and Mass Spectro. |
|---|---|---|
| II-22 | 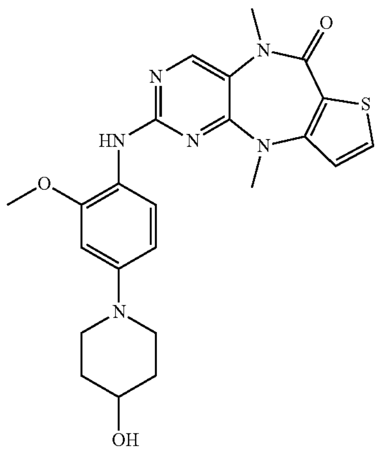 | $^1$H NMR (600 MHz, DMSO-d$_6$) δ 8.21 (s, 1H), 7.88 (s, 1H), 7.83 (d, J = 5.4 Hz, 1H), 7.72 (d, J = 8.7 Hz, 1H), 6.98 (d, J = 5.4 Hz, 1H), 6.62 (d, J = 2.5 Hz, 1H), 6.49 (dd, J = 8.8, 2.6 Hz, 1H), 4.67 (d, J = 4.2 Hz, 1H), 3.81 (s, 3H), 3.65-3.59 (m, 1H), 3.53-3.45 (m, 2H), 3.30 (s, 3H), 3.26 (s, 3H), 2.80 (ddd, J = 12.7, 10.2, 3.0 Hz, 2H), 1.87-1.80 (m, 2H), 1.55-1.46 (m, 2H). $^{13}$C NMR (151 MHz, DMSO-d$_6$) δ 164.1, 162.6, 166.8, 152.9, 151.3, 150.5, 148.6, 132.8, 122.7, 120.9, 120.6, 120.0, 118.9, 107.7, 100.9, 66.5, 56.0, 47.7, 37.2, 36.9, 34.5. MS (ESI) m/z: 436 [M + H]$^+$. |
| II-23 | TFA salt | $^1$H NMR (600 MHz, DMSO-d$_6$) δ 10.08 (s, 1H), 9.71 (s, 1H), 8.28 (s, 1H), 7.85 (d, J = 5.4 Hz, 1H), 7.66 (d, J = 8.7 Hz, 2H), 7.61 (d, J = 8.7 Hz, 2H), 7.02 (d, J = 5.4 Hz, 1H), 6.44 (dd, J = 16.9, 10.1 Hz, 1H), 6.24 (dd, J = 17.0, 2.0 Hz, 1H), 5.73 (dd, J = 10.2, 2.0 Hz, 1H), 3.39 (s, 3H), 3.28 (s, 3H). $^{13}$C NMR (151 MHz, DMSO-d$_6$) δ 164.0, 163.2, 162.8, 158.8, 155.5, 151.6, 150.1, 136.2, 133.8, 132.8, 132.5, 126.8, 121.1, 120.2, 119.9, 119.1, 37.2, 37.2. MS (ESI) m/z: 436 [M + H]$^+$. |
| II-24 | 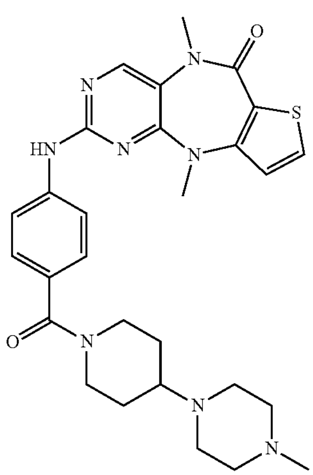 [SMILES: CN1CCN(C2CCN(C(=O)c3ccc(Nc4ncc5c(n4)N(C)c4ccsc4C(=O)N5C)cc3)CC2)CC1] | $^1$H NMR (600 MHz, DMSO-d$_6$) δ 9.82 (s, 1H), 8.34 (s, 1H), 7.86 (d, J = 5.4 Hz, 1H), 7.80 (d, J = 8.7 Hz, 2H), 7.34 (d, J = 8.7 Hz, 2H), 7.02 (d, J = 5.4 Hz, 1H), 3.81-3.76 (m, 1H), 3.41 (s, 8H), 3.29 (s, 3H), 3.18 (s, 3H), 2.48-2.31 (m, 4H), 2.19 (s, 3H), 1.77 (s, 2H), 1.43-1.30 (m, 2H). $^{13}$C NMR (151 MHz, DMSO-d$_6$) δ 169.4, 164.1, 162.5, 156.0, 152.8, 150.4, 142.1, 132.9, 129.0, 128.3, 121.0, 120.9, 119.0, 118.2, 62.5, 61.3, 55.4, 49.1, 48.7, 45.9, 37.2, 25.9. MS (ESI) m/z: 547 [M + H]$^+$. |

TABLE 2-continued

Structure and characterization of compounds II and III

| No | Structure | Data of NMR and Mass Spectro. |
|---|---|---|
| II-25 | 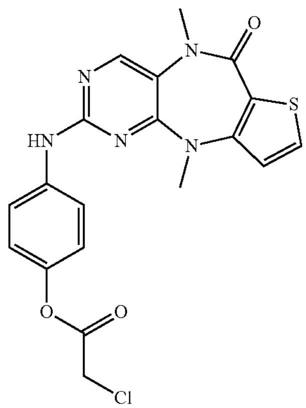 [SMILES: CN1C(=O)c2sccc2N(C)c2nc(Nc3ccc(OC(=O)CCl)cc3)ncc21] | $^1$H NMR (600 MHz, DMSO-d$_6$) δ 9.69 (s, 1H), 8.31 (s, 1H), 7.85 (d, J = 5.4 Hz, 1H), 7.77 (d, J = 9.0 Hz, 2H), 7.10 (d, J = 9.0 Hz, 2H), 7.01 (d, J = 5.4 Hz, 1H), 4.68 (s, 2H), 3.39 (s, 3H), 3.29 (s, 3H). $^{13}$C NMR (151 MHz, DMSO-d$_6$) δ 167.0, 164.1, 162.6, 156.1, 152.8, 150.4, 144.8, 138.9, 132.8, 121.8, 121.0, 120.7, 120.0, 119.1, 41.7, 37.1, 37.1. MS (ESI) m/z: 430 [M + H]$^+$. |
| II-26 | TFA salt | $^1$H NMR (600 MHz, DMSO-d$_6$) δ 9.72 (s, 1H), 9.62 (s, 1H), 8.28 (s, 1H), 7.84 (d, J = 5.4 Hz, 1H), 7.64 (d, J = 8.9 Hz, 2H), 7.10 (d, J = 8.9 Hz, 2H), 7.01 (d, J = 5.4 Hz, 1H), 6.74 (dd, J = 16.5, 10.0 Hz, 1H), 6.09-5.98 (m, 2H), 3.38 (s, 3H), 3.27 (s, 3H). $^{13}$C NMR (151 MHz, DMSO-d$_6$) δ 164.1, 162.7, 155.8, 152.3, 150.3, 137.5, 136.7, 132.9, 131.7, 127.7, 122.1, 121.1, 120.4, 120.0, 119.0, 37.2, 37.2. MS (ESI) m/z: 443 [M + H]$^+$. |
| II-27 | 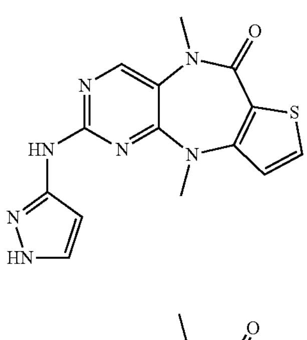 | $^1$H NMR (600 MHz, DMSO-d$_6$) δ 12.19 (s, 1H), 9.68 (s, 1H), 8.26 (s, 1H), 7.85 (d, J = 5.4 Hz, 1H), 7.60 (s, 1H), 7.01 (d, J = 5.4 Hz, 1H), 6.62 (s, 1H), 3.36 (s, 3H), 3.27 (s, 3H). $^{13}$C NMR (151 MHz, DMSO-d$_6$) δ 164.2, 162.7, 153.1, 150.6, 132.8, 121.0, 118.9, 110.0, 72.7, 60.7, 37.1, 37.1. MS (ESI) m/z: 328 [M + H]$^+$. |
| II-28 | 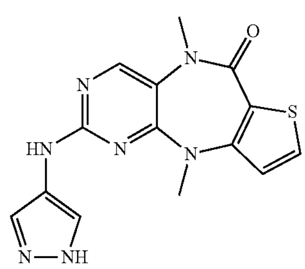 [SMILES: CN1C(=O)c2sccc2N(C)c2nc(Nc3cn[nH]c3)ncc21] | $^1$H NMR (600 MHz, DMSO-d$_6$) δ 12.48 (s, 1H), 9.44 (s, 1H), 8.25 (s, 1H), 7.84 (d, J = 5.5 Hz, 1H), 7.73 (s, 1H), 7.02 (d, J = 5.4 Hz, 1H), 3.39 (s, 3H), 3.27 (s, 3H). $^{13}$C NMR (151 MHz, DMSO-d$_6$) δ 164.2, 163.0, 156.2, 153.2, 150.7, 132.7, 123.2, 121.0, 119.0, 37.2, 37.1. MS (ESI) m/z: 328 [M + H]$^+$. |

TABLE 2-continued

Structure and characterization of compounds II and III

| No | Structure | Data of NMR and Mass Spectro. |
|---|---|---|
| II-29 | 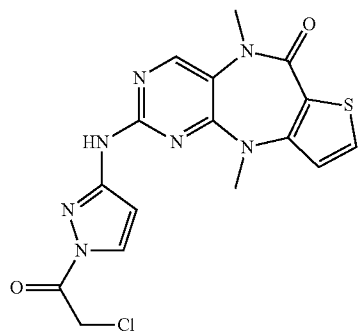 | $^1$H NMR (600 MHz, DMSO-d$_6$) δ 9.71 (s, 1H), 8.26 (s, 1H), 7.85 (d, 5.4 Hz, 1H), 7.59 (s, 1H), 7.01 (d, J = 5.4 Hz, 1H), 6.57 (s, 1H), 4.56 (t, J = 5.5 Hz, 2H), 3.37 (s, 3H), 3.27 (s, 3H). MS (ESI) m/z: 328 [M + H]$^+$. |
| II-30 | 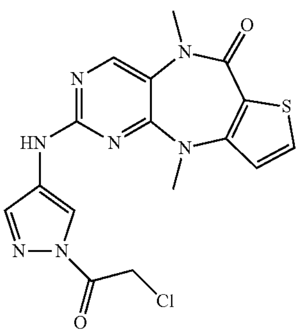 [SMILES: CN1C(=O)c2sccc2N(C)c2nc(Nc3cnn(C(=O)CCl)c3)ncc21] | MS (ESI) m/z: 404 [M + H]$^+$. |
| III-1 | TFA salt | MS (ESI) m/z: 417 [M + H]$^+$. |
| III-2 | 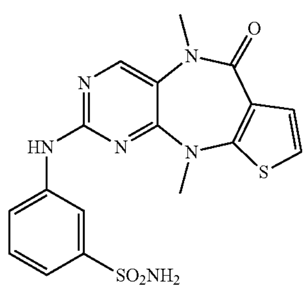 [SMILES: CN1C(=O)c2ccsc2N(C)c2nc(Nc3cccc(S(N)(=O)=O)c3)ncc21] | MS (ESI) m/z: 417 [M + H]$^+$. |

TABLE 2-continued
Structure and characterization of compounds II and III
| No | Structure | Data of NMR and Mass Spectro. |
|---|---|---|
| III-3 | 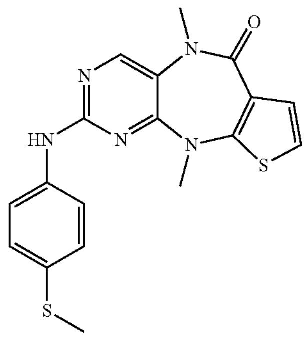 [SMILES: CSc1ccc(Nc2ncc3c(n2)N(C)c2sccc2C(=O)N3C)cc1] | MS (ESI) m/z: 384 [M + H]$^+$. |
| III-4 | 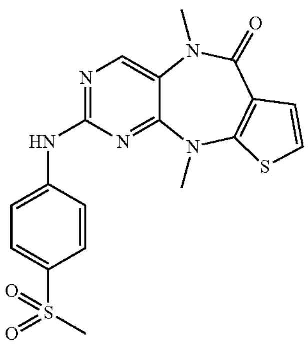 [SMILES: CN1C(=O)c2ccsc2N(C)c2nc(Nc3ccc(S(C)(=O)=O)cc3)ncc21] | MS (ESI) m/z: 416 [M + H]$^+$. |
The Compounds of Formula IV
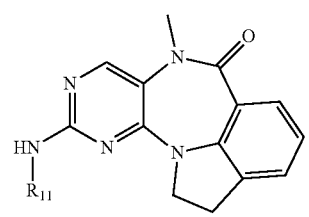
IV
Synthesis of Compounds of Formula IV
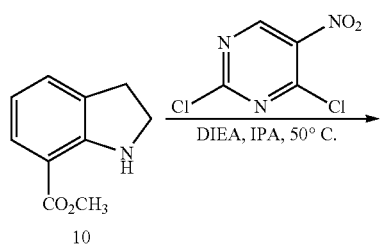
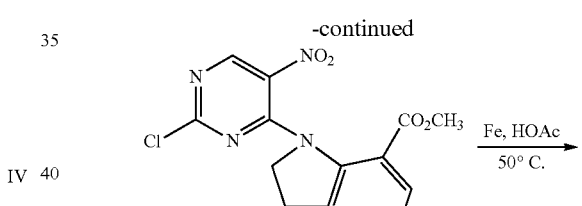
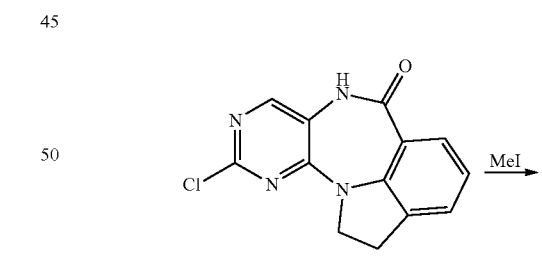
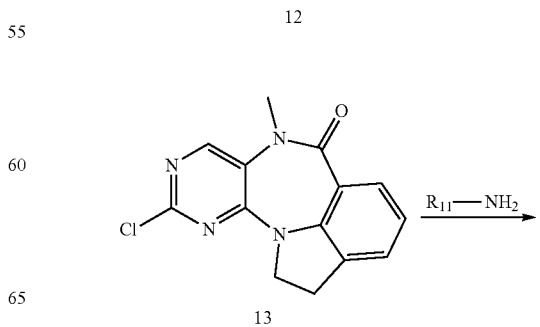

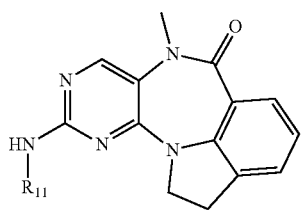

IV

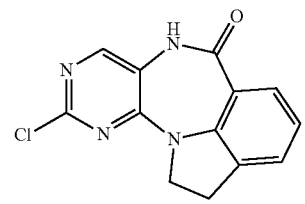

12

Preparation of Compound 11

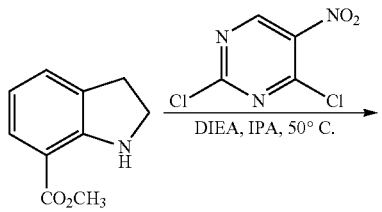

Compound 11 (1.71 g, 5.1 mmol) in acetic acid while stirring, was added iron powder (1.71 g, 30.6 mmol), and then placed in a preheated oil bath to 50 deg. C. The reaction was stirred until LC-MS and after the reaction was complete by TLC the reaction was stopped. Removal of iron, spin off part of acetic acid, poured into ice water to precipitate a solid, filtered using a Buchner funnel and the filter cake washed several times with ice water, and finally collected and dried to give a compound 12 (1.24 g, 89% yield), used for the next step.

MS (ESI) m/z: 273 [M+H]+.

Preparation of Compound 13

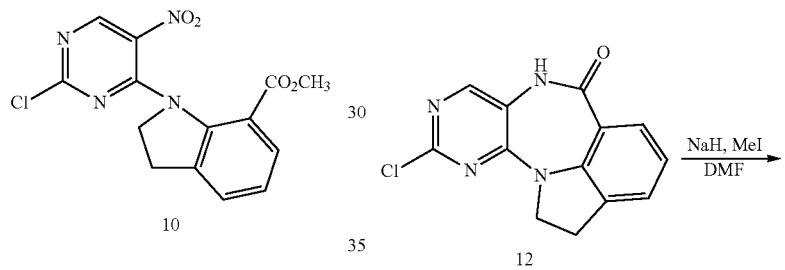

The starting material 10 (1.17 g, 6.6 mmol), N, N-diisopropylethylamine (3.37 mL, 19.8 mmol) was dissolved in 30 mL of isopropanol, after stirring at room temperature was added uniformly dissolved in 5 mL 2 isopropanol, 4-dichloro-5-nitropyrimidine (1.94 g, 10.0 mmol), and finally transferred to a stirred reaction system was preheated oil bath to 50 deg. C., LC-MS and TLC until the reaction was complete after the reaction was stopped.

Concentrated by silica gel column chromatography to give compound 11 (1.71 g, yield 77.4%).

1H NMR (600 MHz, Chloroform-d) δ8.98 (s, 1H), 7.73 (dd, J=7.8, 1.1 Hz, 1H), 7.47 (dd, J=7.4, 1.2 Hz, 1H), 7.24 (t, J=7.6 Hz, 1H), 3.96 (s, 2H), 3.76 (s, 3H), 3.23 (t, J=7.7 Hz, 2H). 13C NMR (151 MHz, Chloroform-d) δ71.1, 166.5, 160.7, 157.1, 154.2, 140.1, 134.8, 128.6, 128.4, 125.5, 122.4, 54.7, 52.1, 29.5. MS (ESI) m/z: 335 [m+H]+.

Preparation of Compound 12

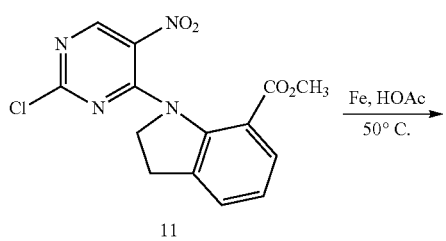

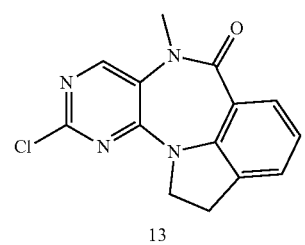

13

Compound 12 (273 mg, 1.0 mmol), iodomethane (0.093 mL, 1.5 mmol) was dissolved in dimethyl formamide, with stirring under ice 5 min, then the system was added to sodium hydride (60 mg, 60% mass fraction), and finally the reaction was stirred raised slowly to room temperature to allow reaction. The reaction was stopped once the LC-MS and TLC measurement were completed. The reaction product was sepatated by silica gel column chromatography (petroleum ether/ethyl acetate=20/1) to give Compound 13 (137 mg, 48% yield).

1H NMR (600 MHz, DMSO-d 6) δ9.50 (s, 1H), 7.85 (d, J=8.0 Hz, 1H), 7.76 (d, J=7.0 Hz, 1H), 7.35 (t, J=7.7 Hz, 1H), 4.44 (t, J=8.0 Hz, 2H), 3.48 (t, J=8.1 Hz, 2H), 3.34 (s, 3H). MS (ESI) m/z: 287 [m+H]+.

Preparation of Compound IV

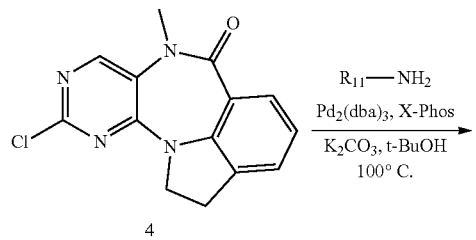 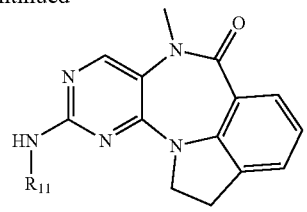

Compound 13 (28.7 mg, 0.1 mmol), aromatic amines (0.1 mmol) was dissolved in 1 ml tert-butanol, was added tris (dibenzylideneacetone) dipalladium (5.5 mg, 0.006 mmol), 2-dicyclohexyl phosphorus-2,4,6-triisopropyl-biphenyl (4.3 mg, 0.009 mmol) and potassium carbonate (55.3 mg, 0.4 mmol), nitrogen was drained out, and placed in a preheated oil bath heated to 100° C. stirring, the reaction was stopped after 5 h. Product was filtered through a fritted funnel to get rid of solids, the liquid was collected and concentrated, purified by silica gel column chromatography to give product IV.

TABLE 3

Structure and Characterization of Compound IV

| No | Structure | Data of NMR and/or Mass Spectro |
|---|---|---|
| IV-1 | (structure with NHSO₂CH₃ para-substituted aniline); TFA salt | $^1$H NMR (600 MHz, DMSO-$d_6$) δ 9.82 (s, 1H), 9.50 (s, 1H), 8.19 (s, 1H), 7.70 (d, J = 7.9 Hz, 1H), 7.66 (d, J = 8.3 Hz, 2H), 7.38 (d, J = 7.2 Hz, 1H), 7.19 (d, J = 8.3 Hz, 2H), 7.01 (t, J = 7.6 Hz, 1H), 4.29 (t, J = 8.5 Hz, 2H), 3.32 (s, 3H), 3.15 (t, J = 8.7 Hz, 2H), 2.95 (s, 3H). $^{13}$C NMR (151 MHz, DMSO-$d_6$) δ 166.6, 159.3, 154.6, 149.3, 147.1, 137.1, 133.4, 132.7, 130.5, 129.6, 123.1, 122.2, 120.4, 119.2, 118.4, 48.0, 39.0, 34.8, 26.8. MS (ESI) m/z: 437 [M + H]$^+$. |
| IV-2 | (structure with SO₂NH₂ meta-substituted aniline); TFA salt | $^1$H NMR (600 MHz, DMSO-$d_6$) δ 9.82 (s, 1H), 8,45 (s, 1H), 8.15 (s, 2H), 7.65 (t, J = 6.9 Hz, 2H), 7.46 (t, J = 7.9 Hz, 1H), 7.41 (d, J = 7.7 Hz, 1H), 7.36 (d, J = 7.2 Hz, 2H), 6.99 (t, J = 7.6 Hz, 1H), 4.27 (t, J = 8.6 Hz, 2H), 3.29 (s, 3H), 3.11 (t, J = 8.6 Hz, 2H). MS (ESI) m/z: 423 [M + H]$^+$. |

TABLE 3-continued

Structure and Characterization of Compound IV

| No | Structure | Data of NMR and/or Mass Spectro |
|---|---|---|
| IV-3 | (structure shown; TFA salt) | $^1$H NMR (600 MHz, DMSO-d$_6$) δ 9.98 (s, 1H), 8.27 (s, 1H), 7.88 (d, J = 8.6 Hz, 2H), 7.75 (d, J = 8.6 Hz, 2H), 7.70 (d, J = 7.8 Hz, 1H), 7.38 (d, J = 7.1 Hz, 1H), 7.19 (s, 2H), 7.01 (t, J = 7.5 Hz, 1H), 4.31 (t, J = 8.6 Hz, 2H), 3.34 (s, 3H), 3.17 (t, J = 8.1 Hz, 2H). $^{13}$C NMR (151 MHz, DMSO-d$_6$) δ 166.7, 159.0, 155.2, 151.4, 147.7, 144.0, 136.5, 133.3, 130.4, 129.5, 127.1, 122.9, 119.4, 119.1, 118.2, 47.9, 38.9, 26.8. MS (ESI) m/z: 423 [M + H]$^+$. |

Test Example

Bioassay:
Inhibition of Mst1/2 Kinase Activity by Compounds
Inhibition of Mst1/2 kinase activity is evaluated by inhibition of phosphorylation level of Mob1 substrate protein by the Mst1/2 kinase as described previously (Cancer Cell, 2009, 16, p 425-438). We adopt a specific ELISA (Enzyme-linked immunosorbent assay) assay for measuring the biochemical activity (FIG. 1).
Specific methods are as follows:
1. The substrate was diluted with purified recombinant GST-Mob1a 200 nM in coating buffer, added to 96-well plates (Nalge Nunc International, Denmark), coated for overnight at 4° C., washed nextday three times with rinsing solution;
2. Add 60 4, of kinase reaction system, 30° C. shaking for 15 min;
Kinase Reaction System:
a. A kinase reaction buffer;
b. ATP (6.7 gIVI for Mst1 kinase reaction, 11.2 gIVI for Mst2 kinase reaction);
c. compound (dissolved in DMSO, containing not more than 1% of the total volume of the reaction);
d. kinase (recombinant Mst1 11 nM or 3.7 nM recombinant MST2);
Control Group Containing No ATP or Kinase;
3. The reaction solution was poured to terminate the kinase reaction, and washed 4 times with rinse solution, 5 minutes each wash;
4. Add 200 μL, per well of the blocking solution, shaking for 1 hour at room temperature, washed 4 times with rinsing solution;
5. Add anti Mob1 35th threonine phosphorylation primary antibody (Cell Signalling, #8699) at 1:1000 dilution in blocking solution, added to 96-well plates for 3 hours at room temperature, rinsed four times;
6. Add 1:1000 dilution of rabbit HRP conjugated secondary antibody (Jackson ImmunoResearch Laboratories #7074), for 30 minutes at room temperature, rinsed four times;
7. Add TMB chromogenic solution (Biolegend, Cat.B200119, B200120). After the color reaction to a certain extent, add to each well 100 μL, of 2M H$_2$SO$_4$ to terminate the reaction;
8. Using a plate reader (VARIOSKAN FLASH, Thermo) to measure absorbance of each well at 450 nM. Each set of three parallel experiments, the negative control is a solution with a final concentration of 1% DMSO, the control is the reaction system containing no ATP. The concentration gradient is 10, 3.33, 1.11, 0.37, 0.123, 0.04, 0.014, 0.004, 0 μM. Kinase activity inhibition rate calculated as follows:

Kinase activity inhibition rate %=1−(OD$_{testgroup}$−OD$_{blank\ group}$)/(OD$_{group}$−OD$_{negative\ control\ group}$)*100%

9) IC$_{50}$ value calculation: IC50 was calculated using Grad-Pad Prism 5 software based on the measurements of kinase activity inhibition rates.
The reagents are as follows:
Coating Buffer: 0.1M NaHCO 3, 0.033M Na2CO$_3$, pH 9.5
Rinse solution: 0.05% Tween-20 in PBS
Reaction buffer: 40 mM of Hepes-NaOH (pH 7.4), 10 mM of MgCl$_2$, 1 mM of dithiothreitol (DTT), 1 mM of NaF, 1 mM of Na$_3$VO$_4$, 1 mM of β-glycerophosphate Blocking solution: 1% BSA dissolved in PBS
Compound Inhibition of Kinase Activity

| No | MST1 IC$_{50}$ (μM) | MST2 IC$_{50}$ (μM) |
|---|---|---|
| IA-2 | 2.38 | 14.80 |
| IA-4 | 2.51 | 2.74 |
| IA-5 | 24.43 | 23.30 |
| IA-6 | >30.00 | >30.00 |
| IB-1 | >30.00 | >30.00 |
| IB-2 | >30.00 | >30.00 |
| IB-3 | >30.00 | >30.00 |
| IC-1 | 0.07 | 0.11 |
| IC-2 | 2.32 | 7.80 |
| IC-3 | 0.67 | 0.52 |
| IC-4 | >30.00 | >30.00 |
| IC-6 | 1.91 | 1.80 |
| IC-7 | 0.50 | 0.09 |
| IC-8 | 13.50 | 0.20 |
| IC-9 | 0.18 | 2.33 |
| IC-10 | 0.24 | 0.08 |
| ID-1 | 0.04 | 0.11 |
| ID-2 | 0.08 | 0.39 |
| ID-3 | 8.65 | >30.00 |
| IE-1 | 0.83 | 2.45 |
| IE-2 | 15.76 | >30.00 |
| IE-3 | 2.72 | 8.21 |
| IF-2 | 0.63 | 3.86 |
| IF-3 | 2.44 | 15.69 |
| IF-4 | 6.46 | >30.00 |

-continued

| No | MST1 IC$_{50}$ (μM) | MST2 IC$_{50}$ (μM) |
|---|---|---|
| IF-5 | >30.00 | >30.00 |
| IF-6 | 9.76 | >30.00 |
| IG-1 | 1.55 | 2.70 |
| IG-2 | 5.80 | 14.64 |
| IG-3 | >30.00 | >30.00 |
| IH-1 | 5.01 | 4.81 |
| IH-2 | 0.89 | 1.68 |
| IH-4 | 0.15 | 0.19 |
| IH-5 | 2.40 | 2.73 |
| IH-6 | >30.00 | >30.00 |
| IH-3 | >30.00 | >30.00 |
| IH-7 | 3.12 | 2.49 |
| IH-8 | 2.17 | 3.36 |
| IH-9 | 5.67 | 11.63 |
| IH-10 | 5.93 | >30.00 |
| IH-11 | 0.23 | 0.44 |
| IH-12 | 1.66 | 1.94 |
| IH-13 | 7.82 | 9.47 |
| IH-14 | >30.00 | 22.53 |
| II-1 | 0.14 | 0.04 |
| II-2 | 2.71 | >30.00 |
| II-3 | 0.85 | 1.72 |
| II-4 | 0.17 | 0.22 |
| II-5 | 4.64 | 8.89 |
| II-6 | 0.26 | 0.02 |
| II-7 | 1.10 | 0.15 |
| II-8 | 0.08 | 1.03 |
| II-10 | 1.02 | 1.97 |
| II-11 | >30.00 | >30.00 |
| II-12 | 0.57 | 0.22 |
| II-13 | 0.33 | 0.26 |
| II-14 | 2.16 | 2.75 |
| II-15 | 0.65 | 1.99 |
| II-16 | >30.00 | >30.00 |
| II-17 | 0.61 | 2.51 |
| II-18 | 3.34 | 13.00 |
| II-19 | 3.03 | 12.59 |
| II-20 | 0.11 | 2.32 |
| II-21 | 0.25 | 3.10 |
| II-22 | >30.00 | >30.00 |
| II-23 | 0.77 | 4.76 |
| II-24 | 0.22 | 2.25 |
| II-25 | 0.58 | 2.24 |
| II-27 | 3.44 | >30.00 |
| II-26 | 0.82 | 0.41 |
| II-28 | 0.54 | 0.36 |
| II-30 | 0.81 | 0.44 |
| IV-1 | 6.07 | 3.97 |
| IV-2 | >30.00 | >30.00 |
| IV-3 | 0.43 | 1.61 |

Figure 2A:
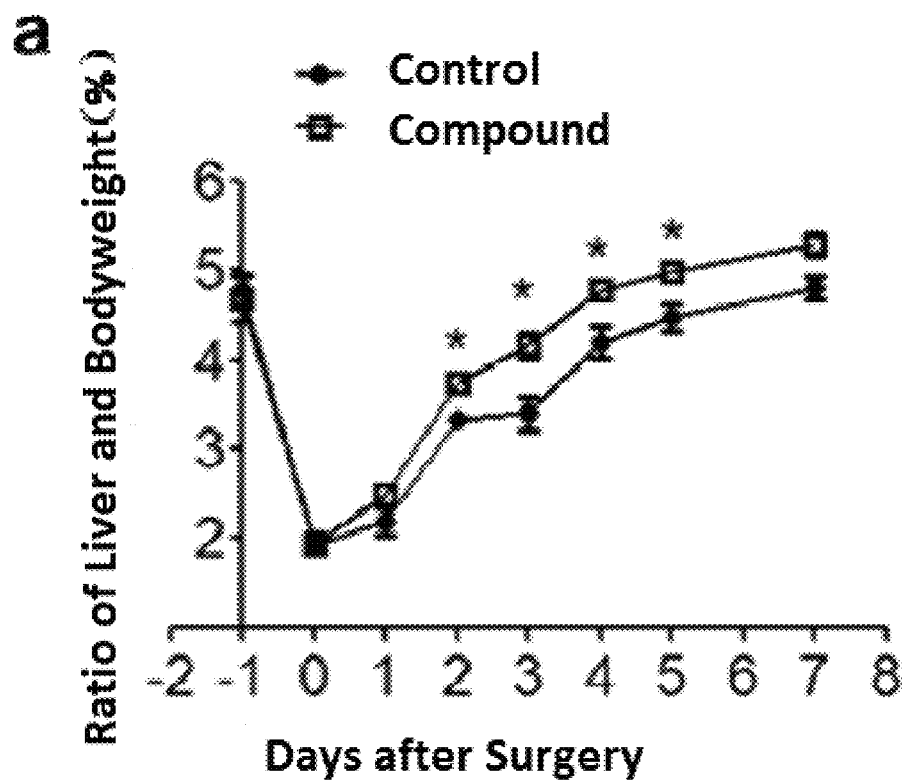
FIG. 2 illustrates that the compound II-1 is effective in promoting regeneration of liver after partial liver lobe resection. After liver lobe resection, mice were injected with compound II-1 (1 mg/kg body weight) or control solvent twice daily, a) shows the ratio of liver and body weight; b) the percentage of Ki67 positive regenerated liver cells in liver tissue slices. Student's t-test in comparing drug-treated group and control group, *P<0.05, ***P<0.001.
Figure 2B:
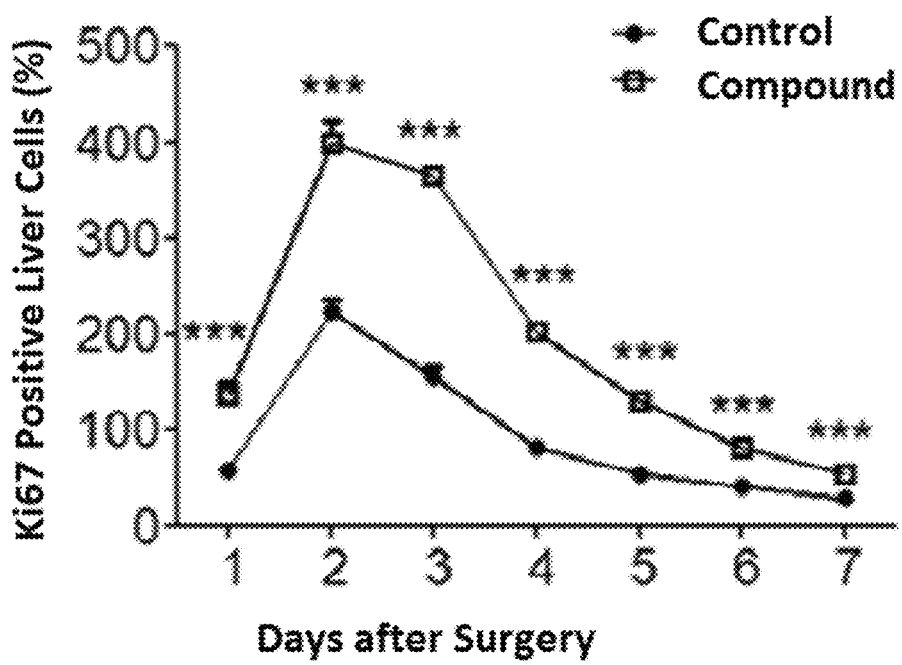
Figure 3A:
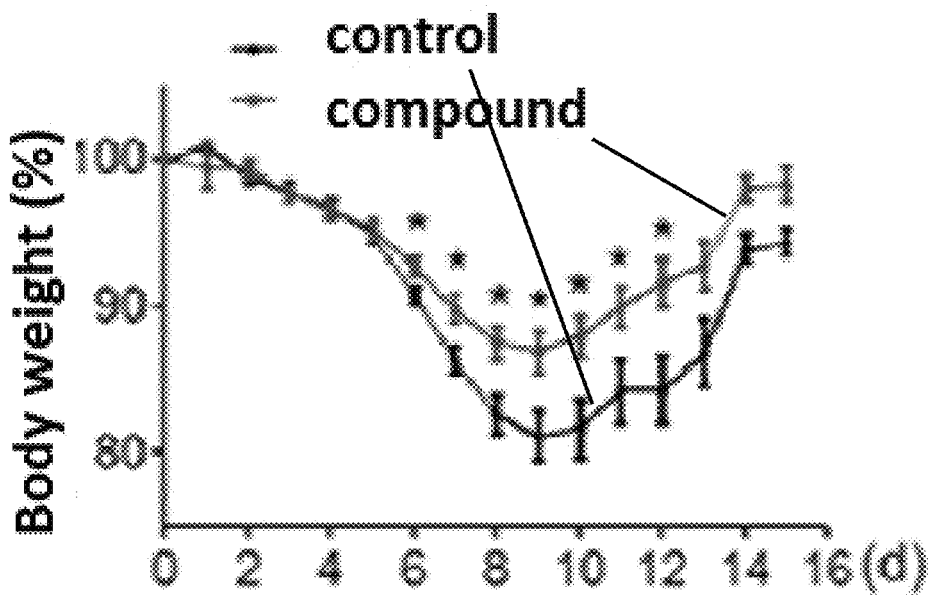
FIG. 3 illustrates that compound II-1 can effectively promote intestinal repair in DSS-induced intestinal injury animal model. Mice fed with DSS for 1-7 days were injected with a compound II-1 (1 mg/kg body weight) or control solvent once daily, a) shows body weight percentage change; b) shows daily DAI values; c) shows intestinal tissue of treatment group and control group after Yap, BrdU and Ki67 immunohistochemical staining; d) and e) show percentage of BrdU positive cells and Ki67 positive cells in the intestinal tissue of the treatment group and control group. Student's t-test in comparing drug-treated group and the control group, *P<0.05, ***P<0.001.
Figure 3B:
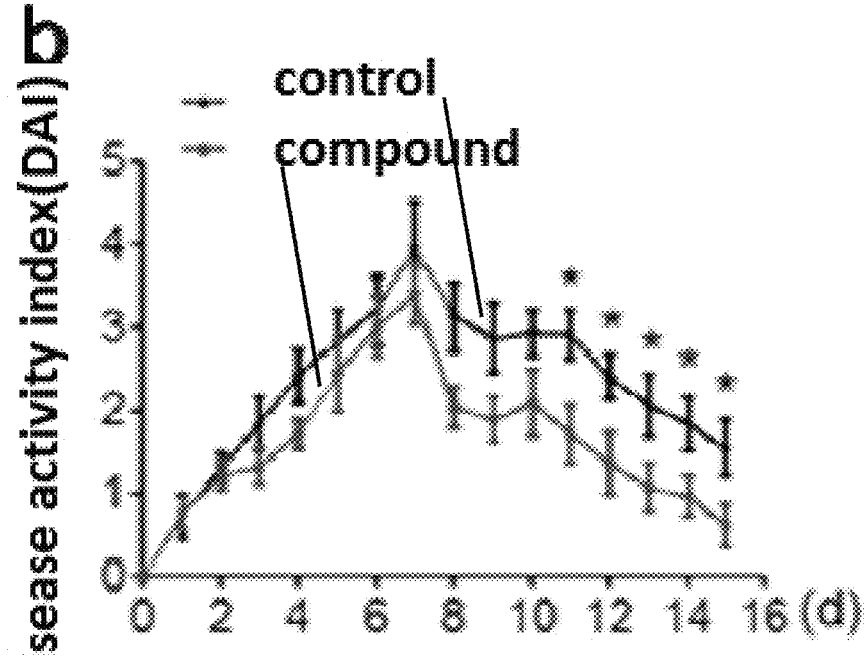
Figure 3C:
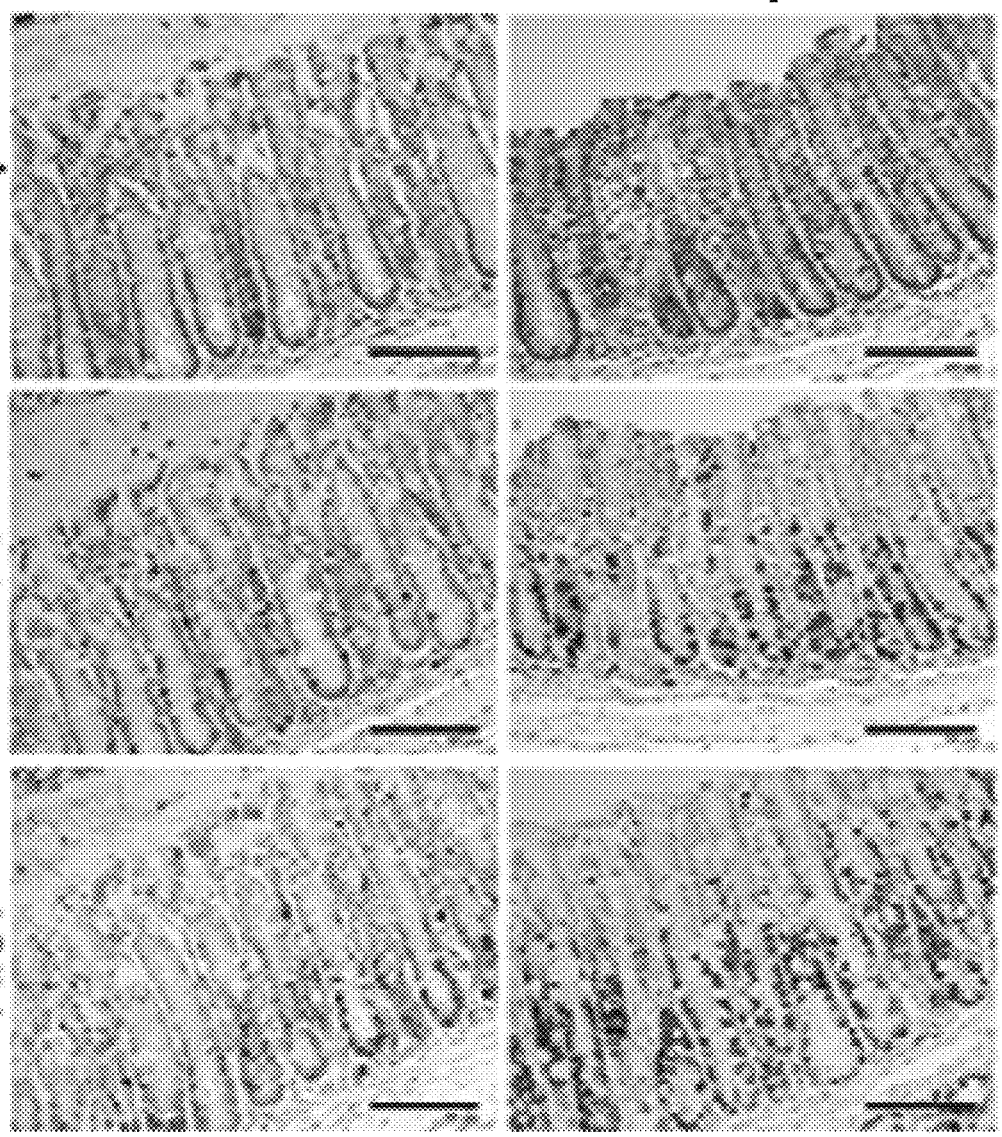
Figure 3D:
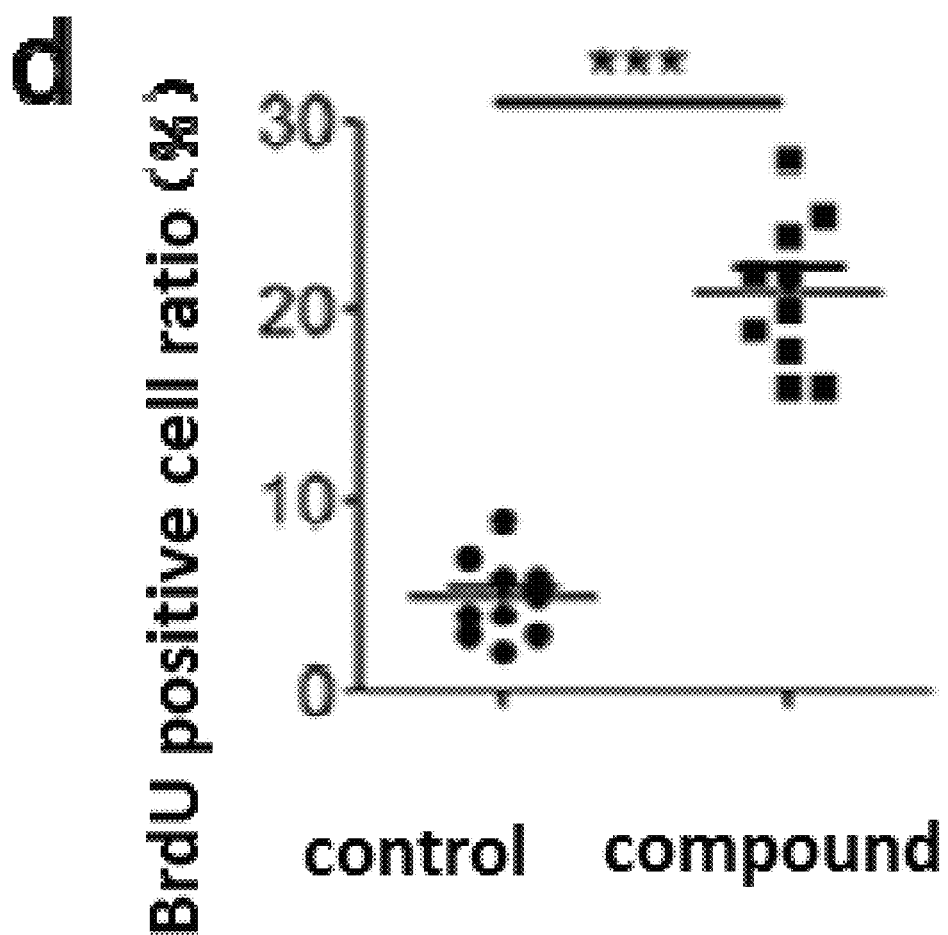
Figure 3E:
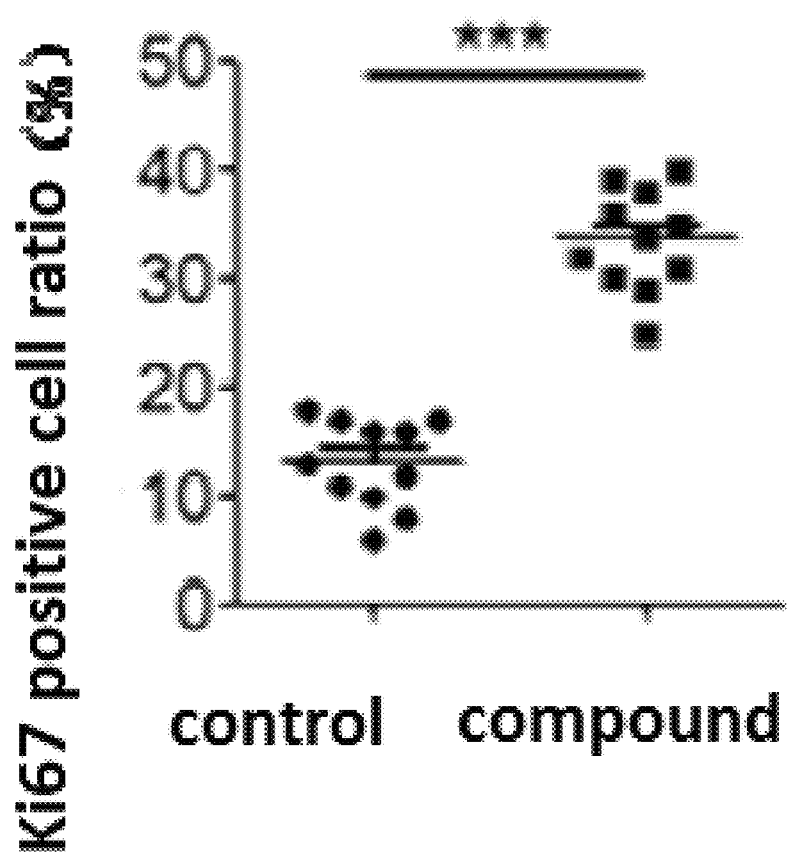

Compound II-1 is Effective in Promoting Liver Regeneration after Partial Liver Resection 8-10 week old wild type mice were anesthetized with intraperitoneal pentobarbital (80 mg/kg body weight). Hepatectomy was performed to remove left rear and intermediate liver lobes, about ⅔ of the entire liver. Mice were injected intraperitoneally the day of surgery Compound II-1 (1 mg/kg body weight) or solvent control group (20% Kolliphor® HS-15 0.1% aqueous citric acid solution). The mice received the compound II-1 or control twice daily until the end of the experiment. Mice after hepatectomy of 1, 2, 3, 4, 5, 6, or 7 days were sacrificed. Mouse body weight and liver weight are recorded and used to calculate the weight ratio of the liver (FIG. 2a). Liver tissue section used in immunohistochemistry to detect proliferating hepatocytes (of Ki67-positive) percentage.

Compound II-1 is Effective in Promoting Intestinal Repair in Intestinal Injury Model Induced by Dextran Sulfate Sodium (Dextran Sulfate Sodium, DSS)

Compound II-1 promotes intestinal repair in intestinal injury mouse model induced by DSS. 8-10 week old wild type mice were fed with water containing 2.5% DSS (MW 36-50 kDa, Cat. #160110, MP Biochemical) for 7 days, then switch to conventional drinking water. The mice were divided into two groups, one group were injected with a compound II-1 (1 mg/kg body weight) once per day, the other group were injected with the above-described control solvent once per day. Throughout the experiment, the body weight of mice was weighed every day at a fixed time and calculate the ratio of the weight and the weight before DSS feeding. Enteritis and other clinical symptoms were observed in mice, including the integrity of feces and intestinal bleeding, which were sued for calculating disease activity index (Disease activity index, DAI). The DAI values were calculated as follows: the integrity of the stool (value 0-3, where 0: full dried fecal pellets; 1: soft particles; 2: loose, wet stool; 3: diarrhea); detection of intestinal bleeding with tolidine (o-tolidine) (value 0-3, where 0: detection reagent was added for 2 minutes, sample no color; 1: detection reagent was added, the sample within 10 seconds from light blue to blue; 2: after adding detection reagents, samples gradually changed from light brown to brown clear blue and a visible color in the feces; 3: after adding detection reagents, samples rapidly becoming brownish blue, significant blood and bleeding in a anus and feces. The body weight change in mice and DAI values were recorded for indicating the degree of intestinal injury repair. Compound II-1 can significantly increase the DSS-treated mice body weight, slow the intestinal injury clinical symptoms (FIG. 3, a, and b). At day 8 after DSS water feeding, some of the mice were sacrificed (intraperitoneal injection of BrdU for detection of cell proliferation two hours before sacrifice), isolated intestinal tissue, for Yap, BrdU and Ki67 immunohistochemical staining, the compound II-1 increases Yap activity in intestinal epithelial cells, promote epithelial repair and cell proliferation (FIG. 3, c, d, e).

The invention claimed is:
1. Compounds of general formula (II), which is the following:

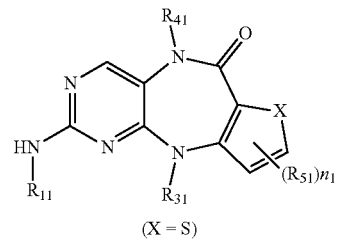

(X = S)

where $n_1$ is selected from 0, 1, 2, 3 or 4;
$R_{11}$ is selected from:
a) C1-C6 alkyl, optionally substituted with halogen, amino, nitro, cyano; C1-C6 alkyl containing oxygen; C3-C7 cycloalkyl, which is optionally substituted with halogen, amino, nitro, cyano; C6-C10 aryl, optionally substituted by halogen, nitro, amino, hydroxy, cyano; C3-C6 alkenyl;
b) 2-N, N-dimethylaminoethyl, 2-hydroxyethyl, 2-N, N-diethylaminoethyl, 2-N, N-diisopropylamino ethyl, 2-morpholinyl ethyl, 2-thiomorpholinyl ethyl, 2-(4-N-piperazinyl-methyl) ethyl, 3-N, N-dimethylaminopropyl, 3-N, N-diethylaminopropyl, 3-N, N-diisopropyl-aminopropyl, 3-morpholinyl propyl, 3-thiomorpholinyl propyl, 3-(4-N-methylpiperidine 1) propyl, 4-N, N-dimethylamino-cyclohexyl, 4-N, N-diethylamino cyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-tert-butoxyl formyl-4-piperidinyl)-4-pyrazolyl;

c)

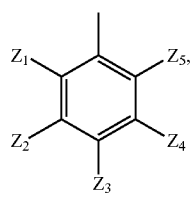

wherein $Z_1$, $Z_2$, $Z_3$, $Z_4$, $Z_5$ are each independently selected from:
(1) hydrogen, halogen, nitro, amino, hydroxy, cyano,
(2) C1-C6 alkyl, C1-C6 alkoxy, C1-C6 alkyl containing oxygen, C1-C6 fluorinated alkyl, C1-C6 fluoroalkoxyl, 4-piperidinyl, N-methyl-4-piperidinyl,
(3) N, N-dimethylamino, N, N-diethylamino, N, N-diisopropylamino, 2-N, N-dimethylaminoethylamino, 2-morpholinyl ethylamino, 2-thiomorpholinyl ethylamino, 2-(4-N-methylpiperazinyl) ethylamino, 3-N, N-dimethyl-amino propylamino, 3-N, N-diethyl-amino propylamino, 3-N, N-diisopropylamino propylamino, 3-morpholinyl propylamino, 3-thiomorpholinyl propylamino, 3-(4 N-methylpiperazinyl) propylamino, N-methylpiperidinyl-4-amino, N-ethylpiperidinyl-4-amino, N-isopropylpiperidinyl-4-amino,
(4) 2-N, N-dimethylaminoethoxyl, 2-N, N-diethyl-aminoethoxyl, 2-N, N-diisopropyl-aminoethoxyl, 2-(N-methylpiperazinyl) ethoxyl, 2-(N-acetyl-piperazinyl) ethoxyl, 2-morpholinyl ethoxyl, 2-thiomorpholinyl ethoxyl, 2-piperidinyl ethoxyl, 3-N, N-dimethylamino propoxyl, 3-N, N-diethyl-amino propoxyl, 3-N, N-diisopropylamino propoxyl, 3-(N-methylpiperazinyl) propoxyl, 3-(N-acetylpiperazinyl) propoxyl, 3-morpholinyl propoxyl, 3-thiomorpholinyl propoxyl, 3-piperidinyl propoxyl, 2-pyridyl methoxyl, 3-pyridyl methoxyl, 4-pyridyl methoxyl, phenylmethoxyl, monohalogen-substituted phenylmethoxyl, homodihalogen-substituted phenylmethoxyl, heterodihalogen-substituted phenylmethoxyl,
(5) piperidinyl, 4-N, N-dimethylamino piperidinyl, 4-N, N-diethylamino piperidinyl, 4-N, N-diisopropylamino piperidinyl, morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydropyrrolyl, N-ethyl-piperazinyl, N-isopropyl-piperazinyl, N-acetyl-piperazinyl, N-tert butoxyl formyl piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethylethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazinyl, 2-oxo-piperazin-4-yl, imidazolyl, 4-imidazolyl,
(6) 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl-formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl, N—(N-methyl-4-piperidinyl) piperazinyl, N—(N-ethyl-4-piperidinyl) piperazinyl,
(7) hydroxy sulfonyl, aminosulfonyl, methylamino sulfonyl, ethylamino sulfonyl, propylamino sulfonyl, isopropylamino sulfonyl, cyclopropylamino sulfonyl, cyclobutylamino sulfonyl, cyclopentylamino sulfonyl, piperidinyl sulfonyl, 4-hydroxy-piperidinyl-1-sulfonyl, 4-N, N-dimethyl-piperidinyl-1-sulfonyl, 4-N, N-diethyl-piperidinyl-1-sulfonyl, tetrahydropyrrolyl-1-sulfonyl, 3-N, N-dimethyl-tetrahydropyrrolyl-1-sulfonyl, 3-N, N-diethyl-tetrahydropyrrolyl-1-sulfonyl, N-methyl-piperazinyl-1-sulfonyl, N-ethylpiperazinyl-1-sulfonyl, N-acetyl-piperazinyl-1-sulfonyl, N-tert-butoxyl formyl-piperazinyl-1-sulfonyl, N-(2-hydroxylethyl) piperazinyl-1-sulfonyl, N-(2-cyanoethyl) piperazinyl-1-sulfonyl, N-(2-N, N-dimethyl ethyl) piperazinyl-1-sulfonyl, N-(2-N, N-diethyl-ethyl) piperazinyl-1-sulfonyl, N-(3-hydroxylpropyl) piperazinyl-1-sulfonyl, N-(3-N, N-dimethyl-aminopropyl) piperazinyl-1-sulfonyl, N-(3-N, N-diethylamino-propyl) piperazinyl-1-sulfonyl, morpholinyl-1-sulfonyl, 3,5-dimethyl-morpholinyl-1-sulfonyl, 4-(N-methyl-1-piperazinyl) piperidinyl-1-sulfonyl, 4-(N-ethyl-1-piperazinyl) piperidinyl-1-sulfonyl, 4-(N-acetyl-1-piperazinyl) piperidinyl-sulfonyl, N—(N-methyl-4-piperidinyl) piperazinyl-1-sulfonyl,
(8) amino formyl, methylamino formyl, ethylamino formyl, propylamino formyl, isopropylamino formyl, cyclopropylamino formyl, cyclobutylamino formyl, cyclopentylamino formyl, piperidinyl-1-formyl, 4-hydroxylpiperidinyl-1-formyl, 4-N, N-dimethyl-piperidinyl-1-formyl, 4-N, N-diethylpiperidinyl-1-formyl, tetrahydropyrrolyl-1-formyl, 3-N, N-dimethyl-tetrahydropyrrolyl-1-formyl, 3-N, N-diethyl-tetrahydropyrrolyl-1-formyl, N-methyl-piperazinyl-1-formyl, N-ethyl-piperazinyl-1-formyl, N-acetyl-piperazinyl-1-formyl, N-tert-butoxyl-formyl-piperazinyl-1-formyl, N-(2-hydroxylethyl) piperazinyl-1-formyl, N-(2-cyanoethyl) piperazinyl-1-formyl, N-(2-N, N-dimethyl-ethyl) piperazinyl-1-formyl, N-(2-N, N-diethyl-ethyl) piperazinyl-1-formyl, N-(3-hydroxylpropyl) piperazinyl-1-formyl, N-(3-N, N-dimethyl-propyl) piperazinyl-1-formyl, N-(3-N, N-diethyl propyl) piperazinyl-1-formyl, morpholinyl-1-formyl, 3,5-dimethyl-morpholinyl-1-formyl, 4-(N-ethyl-1-piperazinyl) piperidinyl-1-formyl, 4-(N-acetyl-1-piperazinyl)-1-piperidinyl-1-formyl, N—(N-methyl-4-piperidinyl) piperazinyl-1-formyl, (9) hydroxyl formyl, methoxyl formyl, ethoxyl formyl, propoxyl formyl, isopropoxyl formyl, n-butoxyl, formyl, isobutoxyl formyl, t-butoxyl formyl,
(10) amino formamido, methylamino formamido, ethylamino formamido, propylamino formamido, isopropylamino formamido, cyclopropylamino formamido, cyclobutylamino formamido, cyclopentylamino formamido, piperidinyl-1-formamido, 4-hydroxy-piperidinyl-1-formamido, 4-N, N-dimethyl-piperidinyl-1-formamido, 4-N, N-diethyl-piperidinyl-1-formamido, tetrahydropyrrolyl-1-formamido, 3-N, N-dimethyl-tetrahydropyrrolyl-1-formamido, 3-N, N-diethyl-tetrahydropyrrolyl-1-formamido, N-methyl-piperazinyl-1-formamido, N-ethyl-piperazinyl-1-formamido, N-acetyl-piperazinyl-1-formamido, N-tert-butoxyl formyl-piperazinyl-1-formamido, N-(2-hydroxylethyl) piperazinyl-1-formamido, N-(2-cyanoethyl) piperazinyl-1-formamido, N-(2-N, N-dimethyl-ethyl) piperazinyl-1-formamido, N-(2-N, N-diethyl-ethyl) piperazinyl-1-formamido, N-(3-hydroxylpropyl) piperazinyl-1-formamido, N-(3-N, N-dimethyl-propyl) piperazinyl-1-formamido, N-(3-N, N-diethyl-amino-propyl) piperazinyl-1-formamido, morpholinyl-1-formamido, 3,5-dimethyl-morpholinyl-1-formamido, 4-(N-methyl-1-piperazinyl) piperidinyl-1-formamido, 4-(N-ethyl-1-piperazinyl) piperidinyl-1-formamido, 4-(N-acetyl-1-piperazinyl) piperidinyl-1-formamido, N—(N-methyl-4-piperidinyl) piperazinyl-1-formamido; or
(11) amino acetamido, N-tert-butoxyl formyl acetamido, N-acetylamino acetamido, acrylamido, cyclopropylamido, chloroacetamido, bromoacetamido, piperidinyl acetamido, 4-hydroxy piperidinyl acetamido, 4-N, N-dimethyl-piperidinyl-acetamido, 4-N, N-diethyl-piperidinyl acetamido, tetrahydropyrrolyl acetamido, 3-N, N-dimethyl-tetrahydropyrrolyl acetamido, 3-N, N-diethyl-tetrahydropyrrolyl-acetamido, N-methyl-piperazinyl acetamido, N-ethyl piperazinyl acetamido, N-acetyl-piperazinyl acetamido, N-tert-butoxyl formyl-piperazinyl acetamido, N-(2-hydroxylethyl) piperazinyl acetamido, N-(2-cyanoethyl) piperazinyl acetamido, N-(2-N, N-dimethylethyl) piperazinyl acetamido, N-(2-N, N-diethyl-ethyl) piperazinyl acetamido, N-(3-hydroxylpropyl) piperazinyl acetamido, N-(3-N, N-dimethyl-propyl) piperazinyl acetamido, N-(3-N, N-diethyl propyl) piperazinyl acetamido, morpholinyl acetamido, 3,5-dimethyl-morpholinyl acetamido, 4-(N-methyl-1-piperazinyl) piperidinyl acetamido, 4-(N-ethyl-1-piperazinyl) piperidinyl acetamido, 4-(N-acetyl-1-piperazinyl) piperidinyl acetamido, N—(N-methyl-4-piperidinyl) piperazinyl acetamido, 4-(tetrahydropyrrolyl-1-yl)piperidinyl acetamido; 2-methylamino-acetamino, 2-(1-methylethyl) amino acetamido; N-benzyloxyl-formyl-2-methylamino-acetamido;
(12) $Z_2$ and $Z_3$ may form a substituted or unsubstituted oxygen-containing five-or six-membered ring; substituents may be selected from the same substituents of $Z_1$,
(13) $Z_2$ and $Z_3$ may form a substituted or unsubstituted nitrogen-containing five-or six-membered ring; substituents may be selected from the same substituents of $Z_1$,

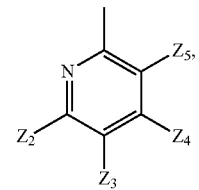

d)

wherein $Z_2$, $Z_3$, $Z_4$, $Z_5$ is the same as defined in 3) above;

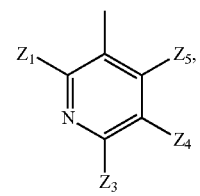

e)

wherein $Z_1$, $Z_3$, $Z_4$, $Z_5$ is the same as defined in 3) above;

$R_{31}$ is selected from:

hydrogen; C1-C6 alkyl, optionally substituted by halogen, nitro, amino, cyano; C3-C7 cycloalkyl, which is optionally substituted by halogen, nitro, amino, cyano;

$R_{41}$ is selected from:

hydrogen; C1-C6 alkyl, optionally substituted by halogen, nitro, amino, cyano; C3-C7 cycloalkyl, optionally substituted by halogen, nitro, amino, cyano;

$R_{51}$ is selected from:

a) a hydrogen, halo, nitro, amino, cyano;

b) C1-C6 alkyl, optionally substituted by halogen, nitro, amino, cyano; —O—C1-C6 alkyl, optionally substituted by halogen, nitro, amino, cyano; C1-C6 oxygen-containing alkyl;

c) methylthio, ethylthio, isopropylthio, methylsulfinyl, ethylsulfinyl, propylsulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sufonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonyl, ethylsulfonyl, propylsulfonyl, isopropylsulfonyl, dimethyl phosphinyl, diethyl phosphinyl, diisopropyl phosphinyl;

or a stereoisomer of the above compounds, a prodrug thereof, a pharmaceutically acceptable salt thereof, or a pharmaceutically acceptable solvate thereof.

2. The compound according to claim 1, which is the following:

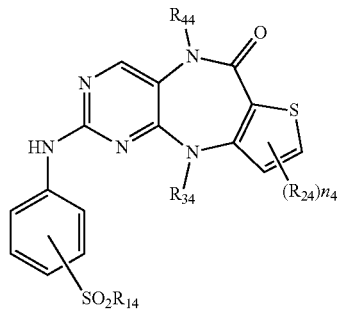

II-1 5

$n_4$ is selected from 0, 1 or 2;
$R_{14}$ is selected from:
  a) five-membered heterocyclic or six-membered heterocyclic rings comprising one or more heteroatoms selected from N, O and S, the five-membered heterocyclic or six-membered heterocyclic rings optionally are substituted with C1-C6 alkyl, C1-C6 alkoxy, hydroxy, amino, alkylamino, dialkylamino, C1-C6 acyl, cyano, and heterocyclic rings substituted by any one or C1-C6 alkyl, —O—C1-C6 alkyl, hydroxy, hydroxy C1-C6 alkyl, C1-C6 acyl, alkylamino, and dialkylamino, including but not limited to: 4-N, N-dimethylamino-piperidinyl, 4-N, N-diethylamino-piperidinyl, 4-N, N-diisopropylamino-piperidinyl, 4-hydroxyl-piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxyl-ethyl) piperazinyl) piperidinyl, 4-(N-(2-cyanoethyl) piperazinyl) piperidinyl, 4-(N-(3-hydroxyl propyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;
  b) amino, cyclopropylamino, cyclobutylamino, cyclopentylamino, cyclohexylamino, N, N-dimethylamino, N, N-diethylamino, N, N-diisopropylamino, 2-N, N-dimethylaminoethyl amino, 2-hydroxyethylamino, 2-morpholinyl-ethylamino, 2-(4-N-methylpiperazinyl) ethylamino, 3-N, N-dimethyl-aminopropyl amino, 3-N, N-diethylamino propylamino, 3-N, N-diisopropylamino-propylamino, 3-hydroxy-propylamino, 3-morpholinyl-propylamino, 3-(4-N-methylpiperazinyl) propylamino, N-methylpiperidinyl-4-amino, N-ethylpiperidinyl-4-amino, N-isopropyl piperidinyl-4-amino, N-acetylpiperidinyl-4-amino; N-methyl-piperazinyl, N-ethyl-piperazinyl, N-isopropyl-piperazinyl, N-acetyl piperazinyl, N-tert-butoxyl formyl-piperazinyl, N-methylsulfonyl-piperazinyl, N-(2-hydroxylethyl) piperazinyl, N-(2-cyanoethyl) piperazinyl, N-(3-hydroxylpropyl) piperazinyl, N-(2-N, N-dimethyl-ethyl) piperazinyl, N-(2-N, N-diethyl-ethyl) piperazinyl, N-(3-N, N-dimethyl-propyl) piperazinyl, N-(3-N, N-diethyl-propyl) piperazinyl, 2-oxo-piperazin-4-yl, N—(N-methyl-4-piperidinyl) piperazinyl, N—(N-ethyl-4-piperidinyl) piperazinyl, N—(N-acetyl-4-piperidinyl) piperazinyl; morpholinyl, 3,5-dimethyl morpholinyl, thiomorpholinyl, tetrahydropyrrolyl, 3-N, N-dimethyl-tetrahydropyrrolyl, 3-N, N-diethyl-tetrahydro-pyrrolyl;
  c) C1-C6 alkyl, optionally substituted by halogen, nitro, cyano;
  d) C3-C7 cycloalkyl, optionally substituted by halogen, nitro, cyano;
  e) —O—C1-C6 alkyl, optionally substituted by halogen, nitro, amino, cyano;
  f) —O—C3-C7 cycloalkyl, optionally substituted by halogen, nitro, amino, cyano;
  g) C6-C10 aryl, optionally substituted by halogen, nitro, amino, cyano; —O—C6-C10 aryl group, optionally substituted by halogen, nitro, amino, cyano;
  h) C2-C6 alkenyl;
  i) hydroxyl, 2-N, N-dimethylaminoethoxyl, 2-N, N-diethyl-aminoethoxyl, 2-N, N-diisopropyl-aminoethoxyl, 2-(N-methylpiperazinyl) ethoxyl, 2-(N-acetyl-piperazinyl) ethoxyl, 2-morpholinyl-ethoxyl, 2-thiomorpholinyl ethoxyl, 2-piperidinyl-ethoxyl, 3-N, N-dimethylamino-propoxyl, 3-N, N-diethyl-amino-propoxyl, 3-N, N-diisopropylamino propoxyl, 3-(N-methylpiperazinyl) propoxyl, 3-(N-acetyl-piperazinyl) propoxyl, 3-morpholinyl-propoxyl, 3-thiomorpholinyl propoxyl, 3-piperidinyl-propoxyl, 2-pyridyl-methoxyl, 3-pyridyl-methoxyl, 4-pyridyl methoxyl, phenylmethoxyl, monohalogen-substituted phenylmethoxyl, homodihalogen-substituted phenylmethoxyl, heterodihalogen-substituted phenylmethoxy;
$R_{24}$ is selected from:
  a) a hydrogen, halo, nitro, amino, cyano;
  b) C1-C6 alkyl, optionally substituted by halogen, nitro, amino, cyano; —O—C1-C6 alkyl, optionally substituted by halogen, nitro, amino, cyano; C1-C6 oxygen-containing alkyl;
  c) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonyl, ethylsulfonyl, propylsulfonyl, isopropylsulfonyl, dimethyl phosphinyl, diethyl phosphinyl, diisopropyl phosphinyl;
$R_{34}$ is selected from:
hydrogen; C1-C6 alkyl, optionally substituted by halogen, nitro, amino, cyano; C3-C7 cycloalkyl, optionally substituted by halogen, nitro, amino, cyano;
$R_{44}$ is selected from:
hydrogen; C1-C6 alkyl, optionally substituted by halogen, nitro, amino, cyano; C3-C7 cycloalkyl, optionally substituted by halogen, nitro, amino, cyano;

Or a stereoisomer of the above compounds, a prodrug thereof, a pharmaceutically acceptable salt thereof, or a pharmaceutically acceptable solvate thereof.

3. The compound according to claim 1, which is the following:

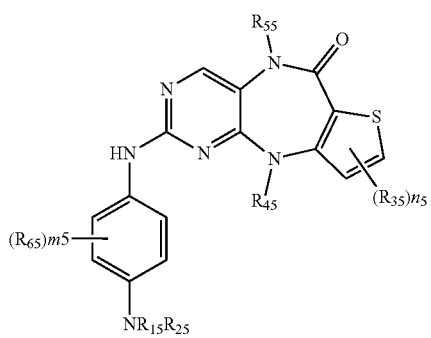

II-2 m5 is selected from 0, 1, 2, 3 or 4;
n5 is selected from 0, 1 or 2;
$R_{15}$, $R_{25}$ independently selected from:
  a) hydrogen; C1-C6 alkyl, optionally substituted by halogen, nitro, amino, cyano; C3-C7 cycloalkyl, optionally substituted by halogen, nitro, amino, cyano; C1-C6 oxygen-containing alkyl;
  b) —$SO_2$ C1-C6 alkyl, optionally substituted by halogen, nitro, amino, cyano; —$SO_2$ C2-C6 alkenyl, optionally substituted with halogen, nitro, amino, cyano substituted; —COC1-C6 alkyl, optionally substituted by halogen, nitro, amino, cyano; —COC2-C6 alkenyl, optionally substituted by halogen, nitro, amino, cyano;
or, $R_{15}$ and $R_{25}$ together with the N atom to which they are attached form a hexaheterocyclic ring containing one or more heteroatoms selected from N, O and S, said hexaheterocyclic ring is optionally substituted with a C1-C6 alkyl, hydroxyl, or amino group;
$R_{35}$ is selected from:
  a) a hydrogen, halo, nitro, amino, cyano;
  b) C1-C6 alkyl, optionally substituted by halogen, nitro, amino, cyano; —O—C1-C6 alkyl, optionally substituted by halogen, nitro, amino, cyano; C1-C6 oxygen-containing alkyl;
  3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;
C1C6C3C7C1C6$R_{45}$ is selected from:
hydrogen; C1-C6 alkyl, optionally substituted by halogen, nitro, amino, cyano; C3-C7 cycloalkyl, optionally substituted by halogen, nitro, amino, cyano;
$R_{55}$ is selected from:
hydrogen; C1-C6 alkyl, optionally substituted by halogen, nitro, amino, cyano; C3-C7 cycloalkyl, optionally substituted by halogen, nitro, amino, cyano;
$R_{65}$ is selected from:
  a) a hydrogen, halo, nitro, amino, cyano;
  b) C1-C6 alkyl, optionally substituted by halogen, nitro, amino, cyano; —O—C1-C6 alkyl, optionally substituted by halogen, nitro, amino, cyano; C1-C6 oxygen-containing alkyl;
  c) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;
or a stereoisomer of the above compounds, a prodrug thereof, a pharmaceutically acceptable salt thereof, or a pharmaceutically acceptable solvate thereof.

4. The compound according to claim 1, which is the following:

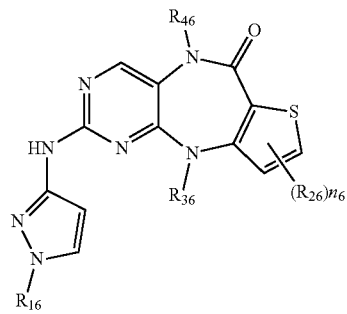

II-3

$n_6$ is selected from 0, 1 or 2;
$R_{16}$ is selected from:
  a) hydrogen; C1-C6 alkyl, optionally substituted by halogen, nitro, amino, cyano; C3-C7 cycloalkyl, optionally substituted by halogen, nitro, amino, cyano; C1-C6 oxygen-containing alkyl;
  b) —$SO_2$ C1-C6 alkyl, optionally substituted by halogen, nitro, amino, cyano; —$SO_2$ C2-C6 alkenyl, optionally substituted with halogen, nitro, amino, cyano substituted; —COC1-C6 alkyl, optionally substituted by halogen, nitro, amino, cyano; —COC2-C6 alkenyl, optionally substituted by halogen, nitro, amino, cyano;
  c) piperidinyl, 4-N, N-dimethylamino-piperidinyl, 4-N, N-diethylamino-piperidinyl, 4-N, N-diisopropylamino-piperidinyl, 4-hydroxyl piperidinyl, 4-(N-methylpiperazinyl) piperidinyl, 4-(N-ethyl-piperazinyl) piperidinyl, 4-(N-isopropyl-piperazinyl)

piperidinyl, 4-(N-acetyl-piperazinyl) piperidinyl, 4-(N-tert-botuxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxypropyl) piperazinyl) piperidinyl, 4-(N-(2-N, N-dimethyl-ethyl) piperazinyl) piperidinyl, 4-(N-(2-N, N-diethyl ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

$R_{26}$ is selected from:
  a) a hydrogen, halo, nitro, amino, cyano;
  b) C1-C6 alkyl, optionally substituted by halogen, nitro, amino, cyano; —O—C1-C6 alkyl, optionally substituted by halogen, nitro, amino, cyano; C1-C6 oxygen-containing alkyl;

3) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{36}$ is selected from: hydrogen; C1-C6 alkyl, optionally substituted by halogen, nitro, amino, cyano; C3-C7 cycloalkyl, optionally substituted with halogen, nitro, amino, cyano replace;

or a stereoisomer of the above compounds, a prodrug thereof, a pharmaceutically acceptable salt thereof, or a pharmaceutically acceptable solvate thereof.

5. The compound according to claim 1, which is the following:

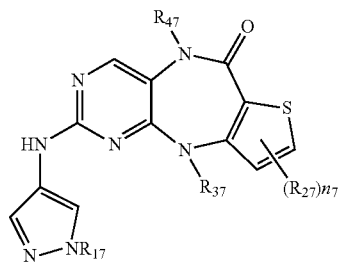

II-4

$n_7$ is selected from 0, 1 or 2;
$R_{17}$ is selected from:
  a) hydrogen; C1-C6 alkyl, optionally substituted by halogen, nitro, amino, cyano; C3-C7 cycloalkyl, optionally substituted by halogen, nitro, amino, cyano; C1-C6 oxygen-containing alkyl;
  b) —SO$_2$ C1-C6 alkyl, optionally substituted by halogen, nitro, amino, cyano; —SO$_2$ C2-C6 alkenyl, optionally substituted with halogen, nitro, amino, cyano substituted; —COC1-C6 alkyl, optionally substituted by halogen, nitro, amino, cyano; —COC2-C6 alkenyl, optionally substituted by halogen, nitro, amino, cyano;
  c) piperidinyl, 4-N, N-dimethylamino-piperidinyl, 4-N, N-diethylamino-piperidinyl, 4-N, N-diisopropylamino-piperidinyl, 4-hydroxyl piperidinyl, 4-(N-methylpiperazinyl) piperidinyl, 4-(N-ethyl-piperazinyl) piperidinyl, 4-(N-isopropyl-piperazinyl) piperidinyl, 4-(N-acetyl-piperazinyl) piperidinyl, 4-(N-tert-butoxyl formyl-piperazinyl) piperidinyl, 4-(N-methylsulfonyl-piperazinyl) piperidinyl, 4-(N-(2-hydroxylethyl) piperazinyl) piperidinyl, 4-(N-(2-cyanoethyl) piperazinyl) piperidinyl, 4-(N-(3-hydroxylpropyl) piperazinyl) piperidinyl, 4-(N-(2-N, N-dimethyl-ethyl) piperazinyl) piperidinyl, 4-(N-(2-N, N-diethyl-ethyl) piperazinyl) piperidinyl, 4-(N-(3-N, N-dimethyl-propyl) piperazinyl) piperidinyl, 4-(N-(3-N, N-diethyl-propyl) piperazinyl) piperidinyl, 4-(tetrahydropyrrolyl) piperidinyl, 4-(3-N, N-dimethyl-tetrahydropyrrolyl) piperidinyl;

$R_{27}$ is selected from:
  a) a hydrogen, halo, nitro, amino, cyano;
  b) C1-C6 alkyl, optionally substituted by halogen, nitro, amino, cyano; —O—C1-C6 alkyl, optionally substituted by halogen, nitro, amino, cyano; a C1 oxygen-containing-C6 alkyl;
  c) methylthio, ethylthio, isopropylthio, methylsulfinyl, ethyl sulfinyl, propyl sulfinyl, methylsulfonyl, ethylsulfonyl, isopropylsulfonyl, amino sulfonyl, ethylamino sulfonyl, propylamino sulfonyl, isopropylamino sulfonyl, cyclopropylamino sulfonyl, hydroxyl formyl, methoxyl formyl, ethoxyl formyl, propoxyl formyl, isopropoxyl formyl, n-butoxyl formyl, isobutoxyl formyl, t-butoxyl formyl, amino formyl, methylamino formyl, ethylamino formyl, propylamino formyl, isopropylamino formyl, cyclopropylamino formyl, cyclobutylamino formyl, cyclopentylamino formyl, acetamido, propionamido, n-butyl amido, isobutyl amido, cyclopropyl formamido, cyclobutyl formamido, cyclopentyl formamido, methylsulfonamido, ethylsulfonamido, propylsulfonamido, isopropylsulfonamido, dimethyl phosphinyl, diethyl phosphinyl, diisopropyl phosphinyl;

$R_{37}$ is selected from:
Hydrogen; C1-C6 alkyl, optionally substituted by halogen, nitro, amino, cyano; C3-C7 cycloalkyl, optionally substituted by halogen, nitro, amino, cyano;
$R_{47}$ is selected from:
hydrogen; C1-C6 alkyl, optionally substituted by halogen, nitro, amino, cyano; C3-C7 cycloalkyl, optionally substituted by halogen, nitro, amino, cyano;
or a stereoisomer of the above compounds, a prodrug thereof, a pharmaceutically acceptable salt thereof, or a pharmaceutically acceptable solvate thereof.

6. Compound selected from the following compounds:
II-1
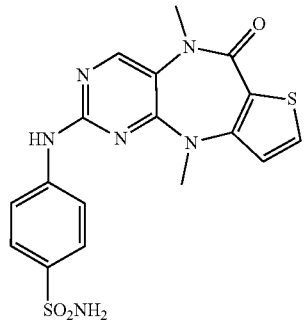
II-2
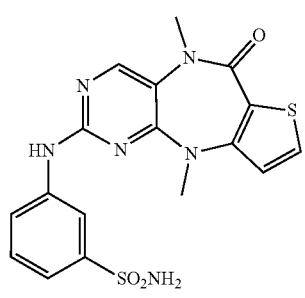
II-3
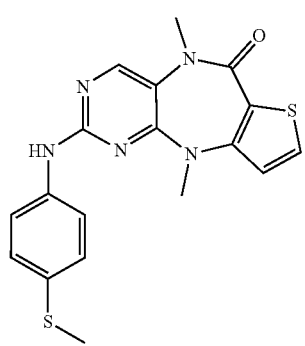
II-4
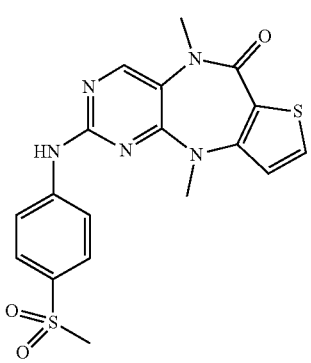
II-5
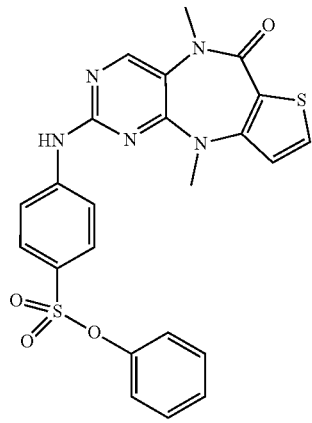
II-6
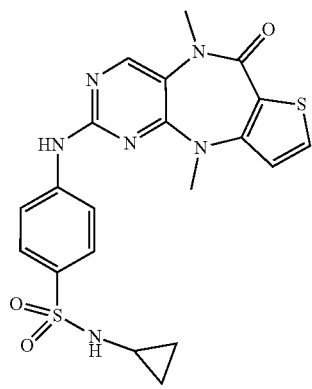
II-7
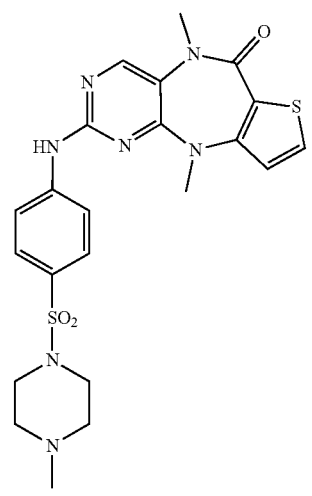

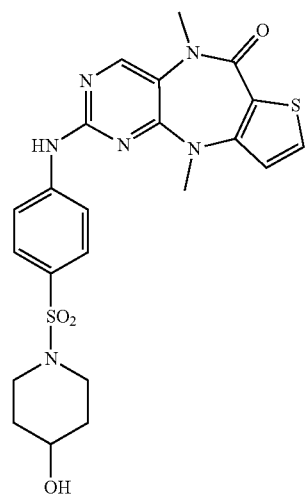
II-8
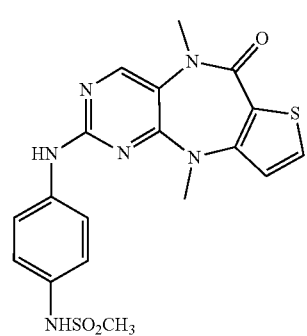
II-9
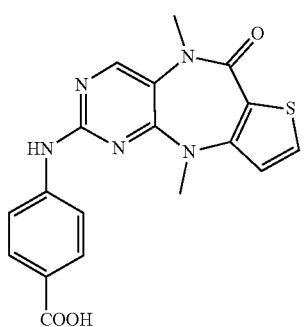
II-10
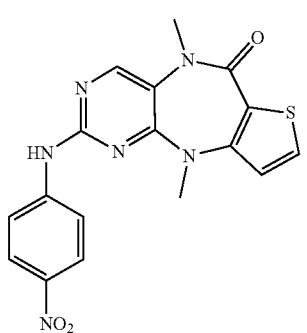
II-11
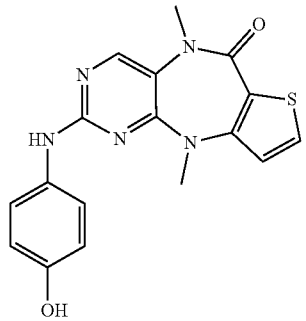
II-12
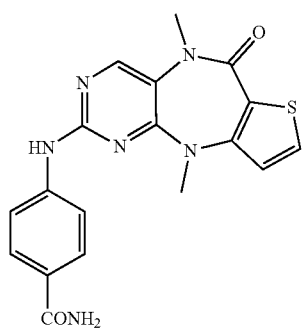
II-13
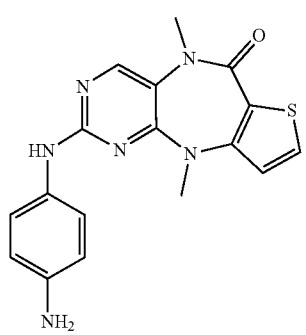
II-14
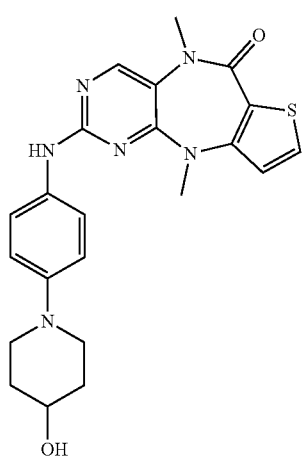
II-15

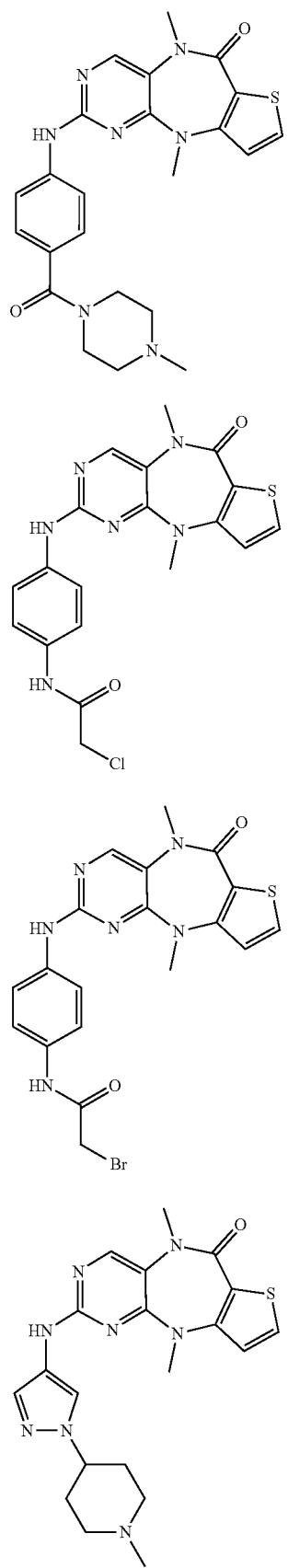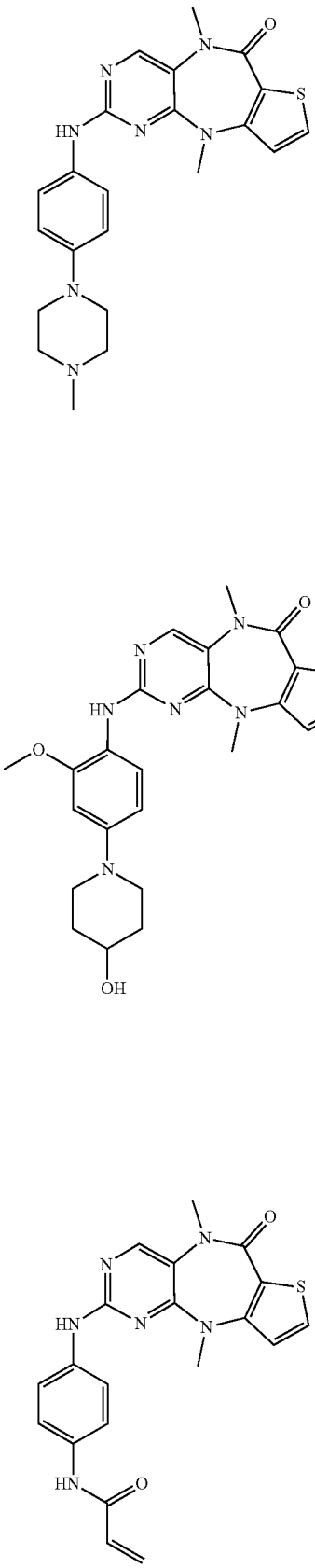

II-24

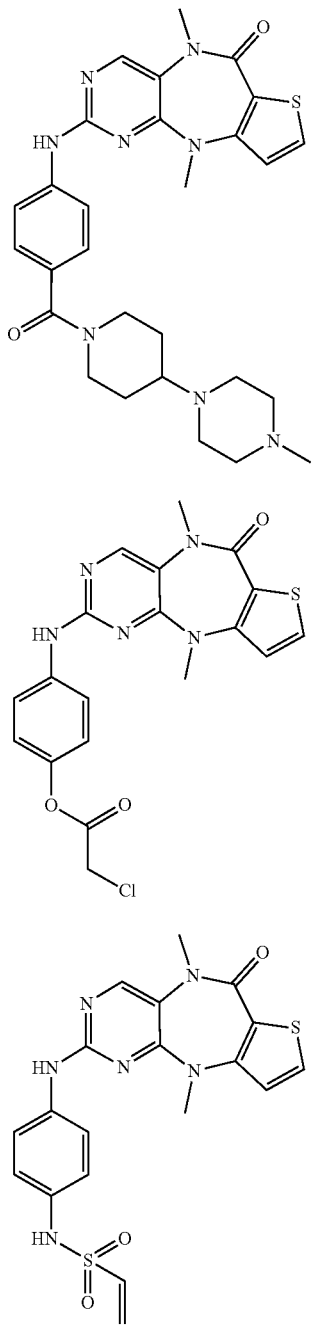

II-25

II-26

II-27

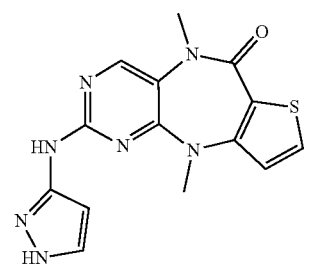

II-28

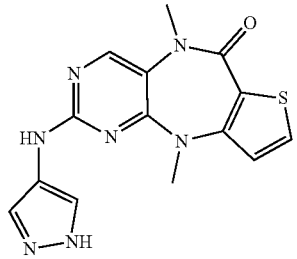

II-29

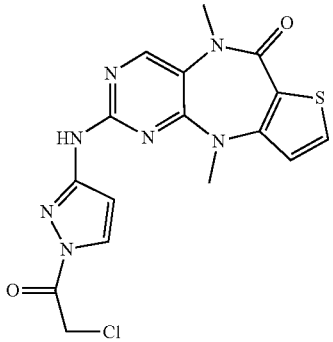

II-30

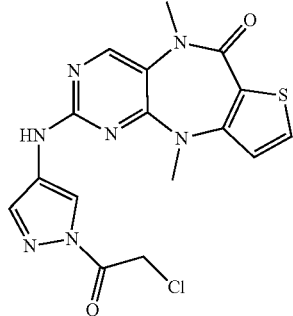

or a stereoisomer of the above compounds, a prodrug of the above compounds, a pharmaceutically acceptable salt of the above compounds, or a pharmaceutically acceptable solvate of the above compounds.

7. The compound of claim 1 prepared by the following synthesis method, wherein symbol Z in formula $R_{41}Z$ and $R_{31}Z$ represents a leaving group such as halo, methylsulfonate, and trifluoromethylsulfonate,

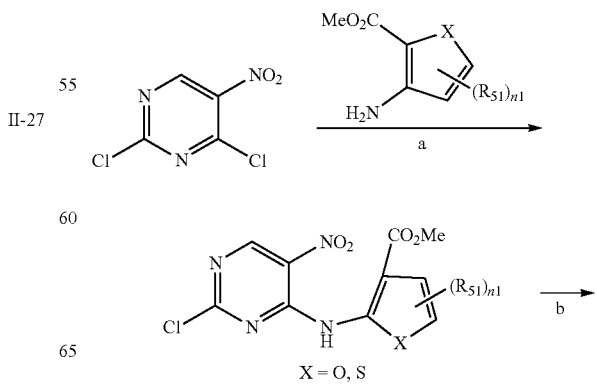

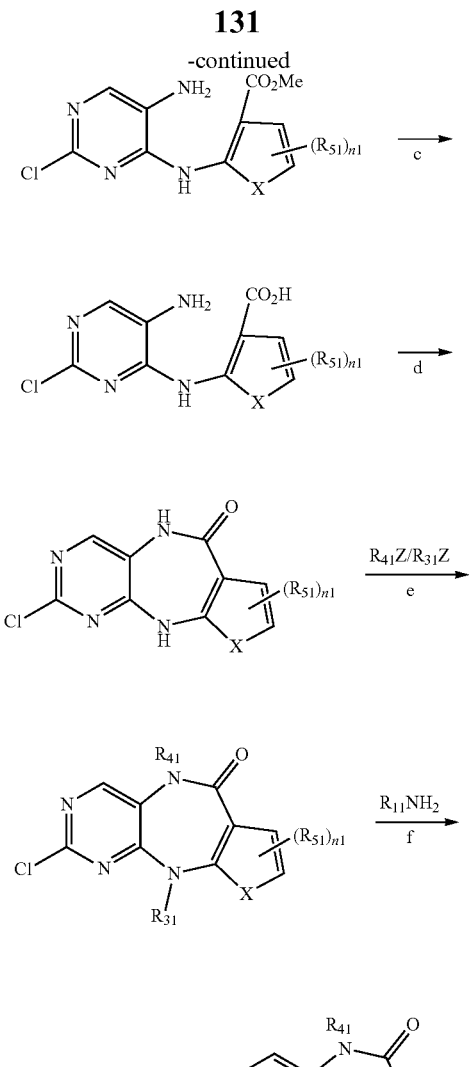

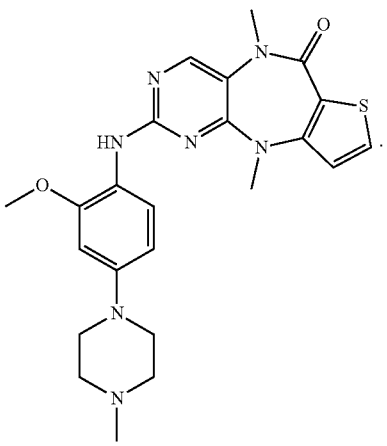

II-16 reaction conditions: (a) basic conditions in the substitution reaction; (b) nitro reduction; (c) ester hydrolysis basic conditions; (d) cyclizing the amide condensation; (e) a basic condition; (f) acidic conditions or palladium catalyzed amination reactions.

8. A pharmaceutical composition comprises the compound of claim 1 or a stereoisomer thereof, a prodrug thereof, a pharmaceutically acceptable salt thereof, or a pharmaceutically acceptable solvate thereof, and optionally a pharmaceutically acceptable excipient.

9. A method comprising a step of administering to a subject in need thereof a compound selected from the compounds according to claim 2 and the following specific compounds as well as their stereoisomers, prodrugs, pharmaceutically acceptable salts, or a pharmaceutically acceptable solvates, for promoting tissue or organ regeneration and repair, promoting stem cell proliferation and somatic cell dedifferentiation, immunosuppressive, treating or preventing neurological disorders associated diseases and local ischemia associated vascular diseases:

10. A method of promoting tissue and organ repair and regeneration, promoting stem cell proliferation and somatic cell dedifferentiation, immunosuppression, and preventing or treating neurological disorder associated diseases and local ischemic associated diseases, comprises administering to a subject in need thereof the compound of claim 1 and one of the following additional specific compounds, as wells as a stereoisomer thereof, a prodrug thereof, a pharmaceutically acceptable salt thereof, or a pharmaceutically acceptable solvate thereof:

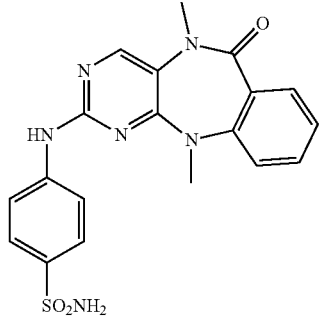

IC-1

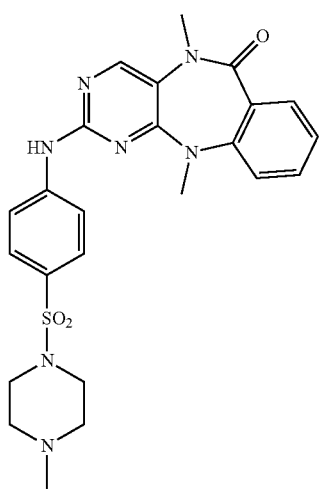

IC-2

IC-3
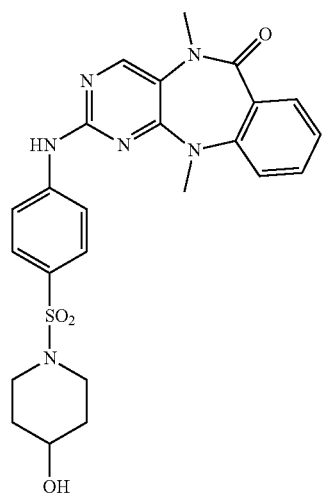
IC-4
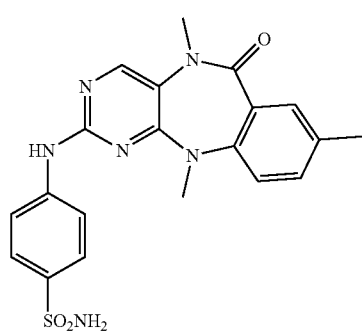
IH-6
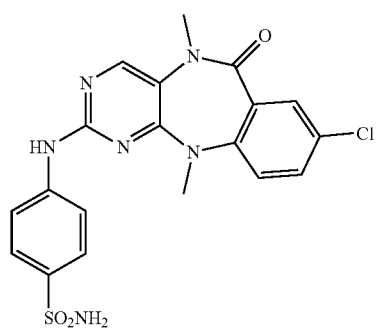
IH-10
IA-1
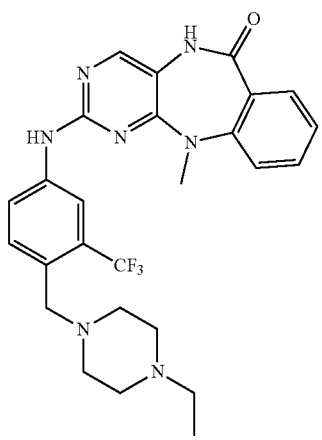
IA-3
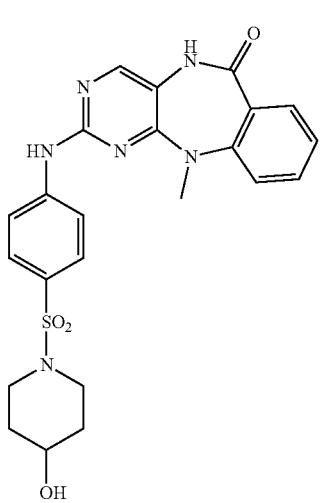
IC-5
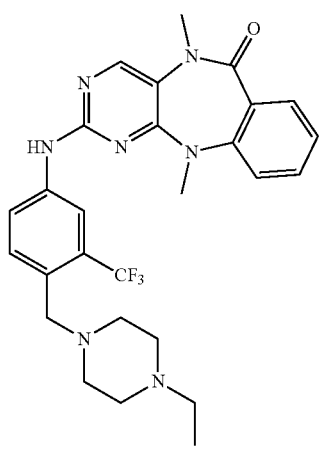

-continued

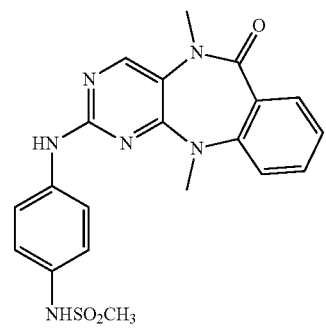
IC-10

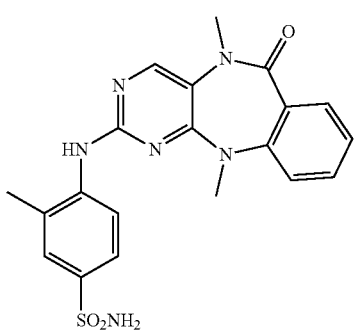
IC-11

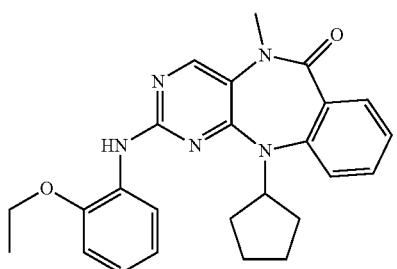
IF-1

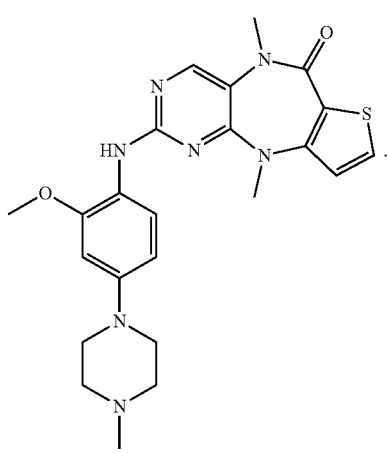
II-16

11. A pharmaceutical composition comprises the compound of claim 6 or a stereoisomer thereof, a prodrug thereof, a pharmaceutically acceptable salt thereof, or a pharmaceutically acceptable solvate thereof, and optionally a pharmaceutically acceptable excipient.

12. Use of the compound according to claim 6 and the following specific compounds as well as their stereoisomers, prodrugs, pharmaceutically acceptable salts, or a pharmaceutically acceptable solvates, in manufacture of medicament for promoting tissue or organ regeneration and repair, promoting stem cell proliferation and somatic cell dedifferentiation, immunosuppressive, treating or preventing neurological disorders associated diseases and local ischemia associated vascular diseases:

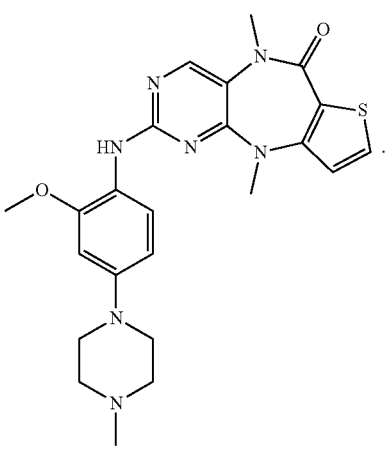
II-16

13. A method of promoting tissue and organ repair and regeneration, promoting stem cell proliferation and somatic cell dedifferentiation, immunosuppression, and preventing or treating neurological disorder associated diseases and local ischemic associated diseases, comprises administering to a subject in need thereof the compound of claim 6 and one of the following additional specific compounds, as wells as a stereoisomer thereof, a prodrug thereof, a pharmaceutically acceptable salt thereof, or a pharmaceutically acceptable solvate thereof:

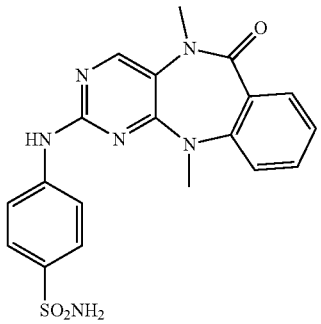
IC-1

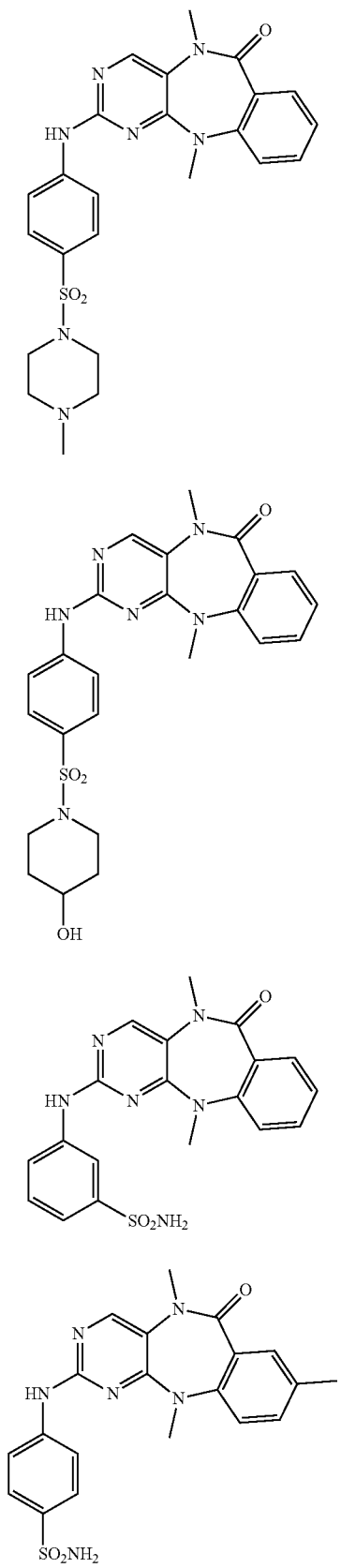
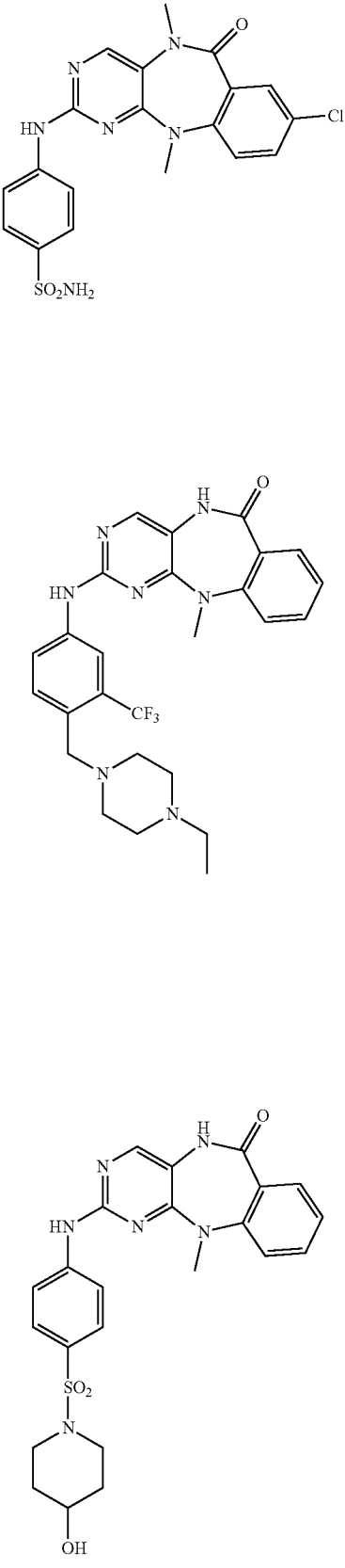

-continued

IC-5
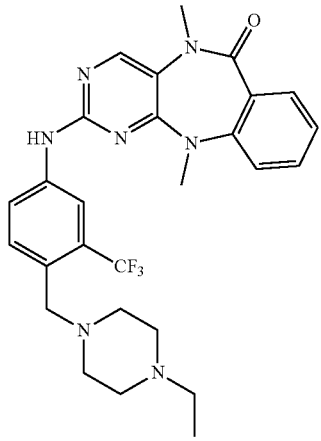

IC-10
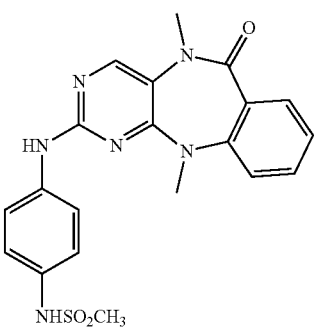

IC-11
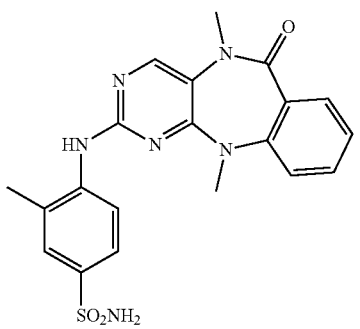

IF-1
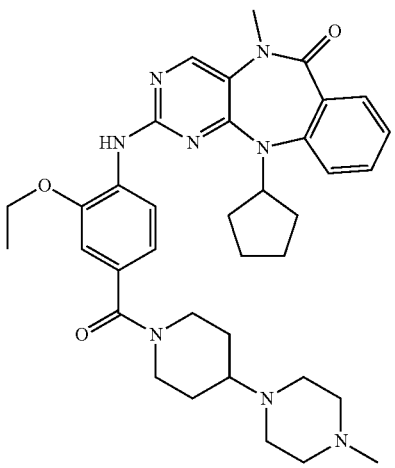

-continued

II-16
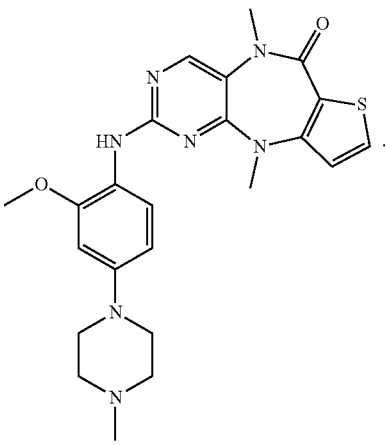

14. The method of claim 9, wherein the tissue and organ regeneration and repair is selected from the group consisting of liver repair and regeneration, intestinal regeneration and repair, cardiac repair and regeneration, skin regeneration and repair.

15. The method of claim 9, wherein the neurological disorder associated disease is selected from the group consisting of Alzheimer's disease, multiple sclerosis, Parkinson's disease, stroke.

16. The method of claim 10, wherein the tissue and organ regeneration and repair is selected from the group consisting of liver repair and regeneration, intestinal regeneration and repair, cardiac repair and regeneration, skin regeneration and repair.

17. The method of claim 10, wherein the neurological disorder associated disease is selected from the group consisting of Alzheimer's disease, multiple sclerosis, Parkinson's disease, stroke.

18. The compound of claim 1, wherein the pharmaceutically acceptable salt is selected from the group consisting of a hydrochloride, a hydrobromide, a hydroiodide, a nitrate, a bicarbonate, a carbonate, a sulfate, a phosphate, a formate, an acetate, a propionate, a benzoate, a maleate, a fumarate, a succinate, a tartrate, a citrate, an ascorbates, an alpha-ketoglutarate, an alpha-glycerophosphate, an alkyl sulfonate and an aryl sulfonate.

19. The compound of claim 1, wherein $n_1$ is selected from 0, 1, 2, 3; $R_{11}$ is selected from:
a) C1-C6 alkyl, optionally substituted by halogen, nitro, cyano; C1-C6 alkyl containing oxygen; C3-C7 cycloalkyl, which is optionally substituted by halogen, nitro, cyano; a C6-10 aryl, optionally substituted by halogen, nitro, amino, hydroxy, cyano;
b) 2-N, N-dimethylaminoethyl, 2-hydroxylethyl, 2-N, N-diethylaminoethyl, 2-N, N-diisopropylamino ethyl, 2-morpholinyl ethyl, 2-thiomorpholinyl ethyl, 2-(4-N-methyl piperazinyl) ethyl, 3-N, N-dimethylamino propyl, 3-N, N-diethylamino propyl, 3-N, N-diisopropylamino propyl, 3-morpholinyl propyl, 3-thiomorpholinyl propyl, 3-(4-N-piperazinyl-methyl) propyl, 4-N, N-dimethylamino-cyclohexyl, 4-N, N-diethylamino cyclohexyl, N-methyl-4-piperidinyl, N-ethyl-4-piperidinyl, N-isopropyl-4-piperidinyl, 1,3-dimethyl-5-pyrazolyl, 1-methyl-4-pyrazolyl, 3-methyl-5-isoxazolinyl, 1-(N-methyl-4-piperidinyl)-4-pyrazolyl, 1-(N-tert-butoxyl formyl-4-piperidinyl)-4-pyrazolyl;

$Z_3$ of $R_{11}$ is selected from amino, aminosulfonyl, methylamino sulfonyl, cyclopropylamino sulfonyl, piperidinyl sulfonyl, 4-hydroxyl piperidinyl-1-sulfonyl, 4-N, N-dimethyl-piperidinyl-1-sulfonyl, tetrahydropyrrolyl-1-sulfonyl, 3-N, N-dimethyl-tetrahydropyrrolyl-1-sulfonyl, N-methyl piperazinyl-sulfonyl, N-ethyl-piperazinyl-1-sulfonyl, morpholinyl-1-sulfonyl, methylsulfonamido, ethylsulfonamido, isopropylsulfonamido, vinylsulfonamido, carboxylic acid group, amino formyl, methylamino formyl, ethylamino formyl, isopropylamino formyl, cyclopropylamino formyl, piperidinyl-1-formyl, 4-hydroxylpiperidinyl-1-formy, 4-N, N-dimethyl-piperidinyl-1-formyl, tetrapyrrolyl-1-formyl, 3-N, N—dimethyl-tetrahydropyrrolyl-1-formyl, N-methyl-piperazinyl-1-formyl, N-ethyl-piperazinyl-1-formyl, N-acetyl-piperazinyl-1-formyl, morpholinyl-1-formyl, 4-(N-methyl-1-piperazinyl) piperidinyl-1-formyl, 4-(N-ethyl-1-piperazinyl) piperidinyl-1-formyl, 4-(N-acetyl-1-piperazinyl) piperidinyl-1-formyl, N—(N-methyl-4-piperidinyl) piperazinyl-1-formyl, chloroacetamido, bromoacetamido, acrylamido;

$R_{31}$ is selected from hydrogen; C1-C6 alkyl; C3-C7 cycloalkyl;

$R_{41}$ is selected from hydrogen; C1-C6 alkyl; C3-C7 cycloalkyl;

$R_{51}$ is selected from hydrogen, halo, nitro, amino, cyano; C1-C6 alkyl, optionally substituted by halogen, nitro, amino, cyano; —O—C1-C6 alkyl, optionally substituted with halogen, nitro, amino, cyano; C1-C6 alkyl containing oxygen.

\* \* \* \* \*